(12) United States Patent
Markel

(10) Patent No.: US 8,815,248 B2
(45) Date of Patent: Aug. 26, 2014

(54) MODULATION OF IMMUNITY AND CEACAM1 ACTIVITY

(76) Inventor: Gal Markel, Haifa (IL)

( * ) Notice: Subject to any disclaimer, the term of this patent is extended or adjusted under 35 U.S.C. 154(b) by 0 days.

(21) Appl. No.: 11/423,366

(22) Filed: Jun. 9, 2006

(65) Prior Publication Data

US 2007/0110668 A1 May 17, 2007

Related U.S. Application Data

(60) Provisional application No. 60/689,316, filed on Jun. 9, 2005.

(51) Int. Cl.
*A61K 39/00* (2006.01)

(52) U.S. Cl.
USPC .................................................. 424/184.1

(58) Field of Classification Search
None
See application file for complete search history.

(56) References Cited

U.S. PATENT DOCUMENTS

| | | | | |
|---|---|---|---|---|
| 6,843,989 | B1 * | 1/2005 | Siegall et al. | 424/130.1 |
| 6,852,320 | B2 | 2/2005 | Blumberg | |
| 2003/0022292 | A1 * | 1/2003 | Gray-Owen et al. | 435/69.1 |
| 2004/0005321 | A1 | 1/2004 | Singer et al. | |
| 2004/0047858 | A1 | 3/2004 | Blumberg et al. | |
| 2004/0214184 | A1 * | 10/2004 | Skubitz et al. | 435/6 |
| 2005/0107324 | A1 | 5/2005 | Bennett et al. | |

FOREIGN PATENT DOCUMENTS

WO 99/52552 10/1999

OTHER PUBLICATIONS

Markel et al (Journal of Immunology, Mar. 2002, 168(6): 2803-2810).*
Flaherty et al (Cancer, 1993, 71(11): Abstract).*
Markel et al (J Immunol, Mar. 2002, 168(6):2803-10).*
Flaherty et al (Cancer, 1993, 71(11): 3520-3525).*
International Search Report corresponding to International Application No. PCT/IB2006/003981, mailed Jul. 29, 2008, 2 pages.
Written Opinion of the International Searching Authority corresponding to International Application No. PCT/IB2006/003981, mailed Jul. 29, 2008, 5 pages.
Kammerer et al., "The tumour suppressor gene CEACAM1 is completely but reversibly downregulated in renal cell carcinoma." Journal of Pathology, 2004, vol. 204, pp. 258-267.
Gal Markel et al., "The mechanisms controlling NK cell autoreactivity in TAP2-deficient patients." Blood, Mar. 1, 2004, vol. 103, No. 5, pp. 1770-1778.
Gal Markel et al., "Biological function of the soluble CEACAM1 protein and implications in TAP2-deficient patients." Eur. J. Immunol, 2004, vol. 34, pp. 2138-2148.
Gal Markel et al., "Pivotal role of CEACAM1 protein in the inhibition of activated decidual lymphocyte functions." The Journal of Clinical Investigation, Oct. 2002, vol. 110, No. 7, pp. 943-953.
Gal Markel et al., "The Critical Role of Residues 43R and 44Q of Carcinoembryonic Antigen Cell Adhesion Molecules-1 in the Protection from Killing by Human NK Cells." The American Association of Immunologists, Inc., 2004, pp. 3732-3739.
International Preliminary Report on Patentability for International Patent Application Serial No. PCT/IB2006/003981, mailed Mar. 19, 2009.
European Search Report corresponding to European Patent Application No. 06847252.1-2406, mailed Feb. 4, 2010.
Stern et al., "Carcinoembryonic antigen (CEA) inhibits NK killing via interaction with CEA-related cell adhesion molecule 1." Journal of Immunology, vol. 174, No. 11, Jun. 1, 2005, pp. 6692-6701, XP002560495.

* cited by examiner

*Primary Examiner* — Sean Aeder

(74) *Attorney, Agent, or Firm* — McAndrews, Held & Malloy, Ltd.

(57) ABSTRACT

The present technology comprises methods for regulating an the immune system, and in particular methods for the regulation of a specific immune response, including the regulation of lymphocyte activity. Methods of the present technology comprise both the negative and positive modulation of CEACAM1 protein function.

3 Claims, 32 Drawing Sheets

FIGURE 1
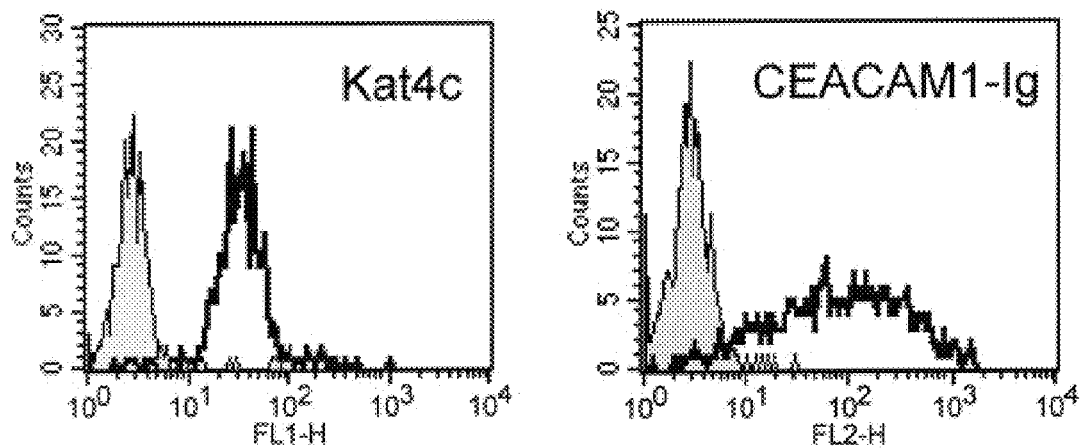
.221/CEACAM6
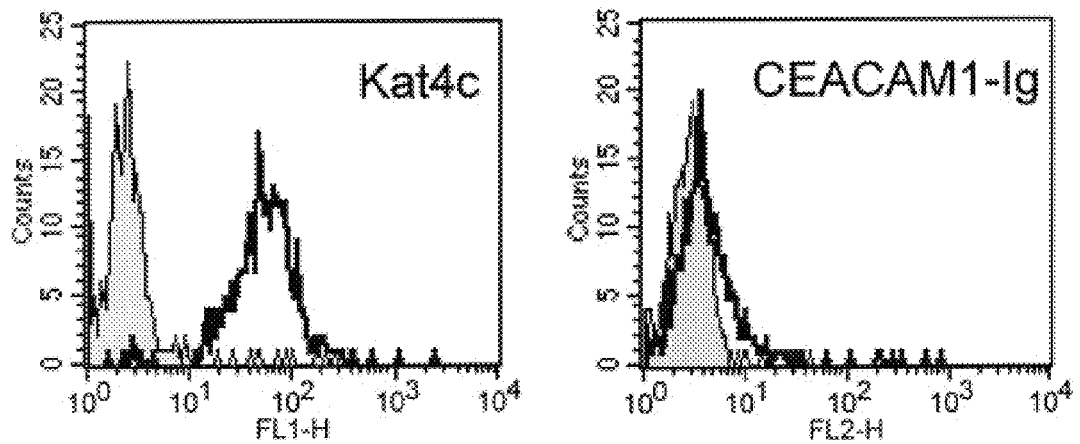

FIGURE 4

```
         1
CEACAM1    QLTTIES MPFNVAEGKE VLLLVHNLPQ QLFGYSWYKG ERVDGNRQIV GYAIGTQQAT
CEACAM3    KLTIES  MPLSVAEGKE VLLLVHNLPQ HLFGYSWYKG ERVDGNSLIV GYVIGTQQAT
CEACAM5    KLTIES  TPFNVAEGKE VLLLVHNLPQ HLFGYSWYKG ERVDGNRQII GYVIGTQQAT
CEACAM6    KLTIES  TPFNVAEGKE VLLLAHNLPQ NRIGYSWYKG ERVDGNSLIV GYVIGTQQAT

CEACAM1    PGPANSGRET IYPNASLLIQ NVTQNDTGFY TLQVIKSDLV NEEATGQFHV YP
CEACAM3    PGAAYSGRET IYTNASLLIQ NVTQNDIGFY TLQVIKSDLV NEEATGQFHV YQ
CEACAM5    PGPAYSGRET IYPNASLLIQ NIIQNDTGFY TLHVIKSDLV NEEATGQFRV YP
CEACAM6    PGPAYSGRET IYPNASLLIQ NVTQNDTGFY TLQVIKSDLV NEEATGQFHV YP
```

FIGURE 18
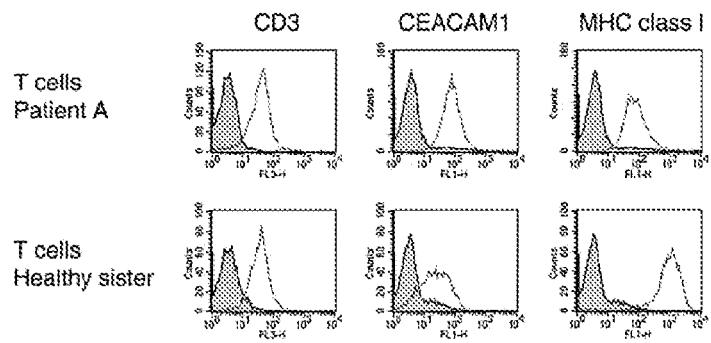
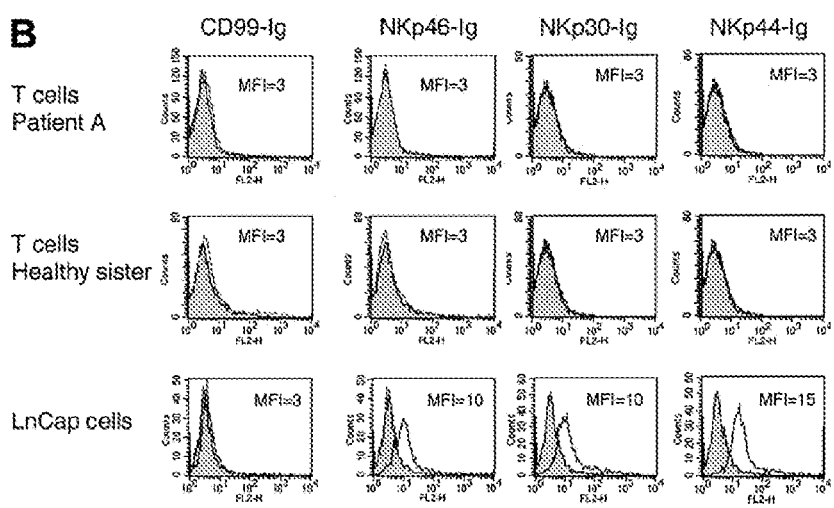
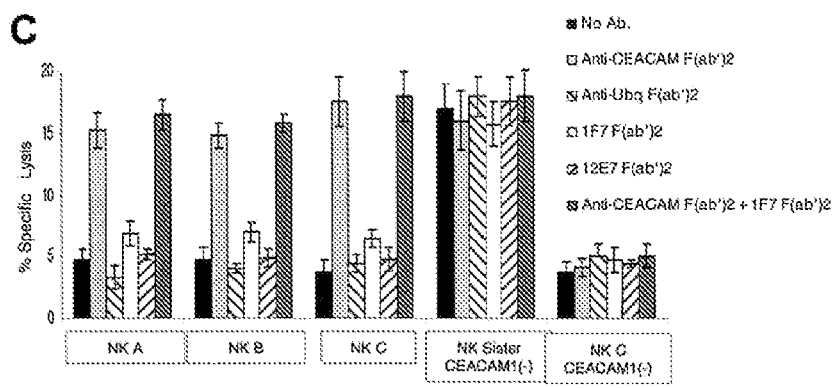
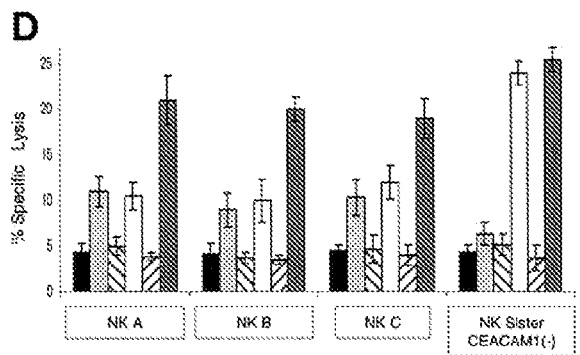

MODULATION OF IMMUNITY AND CEACAM1 ACTIVITY

CROSS-REFERENCE TO RELATED APPLICATIONS/INCORPORATION BY REFERENCE

The present application is related to and claims priority from U.S. Provisional Patent Application Ser. No. 60/689,316, filed Jun. 9, 2005, and titled "THE MODULATION OF IMMUNITY AND CEACAM1 ACTIVITY," the contents of which are hereby incorporated herein by reference in their entirety.

FIELD OF THE INVENTION

The invention relates to the modulation of the immune system in general. More specifically, certain embodiments of the invention relate to the modulation of specific immune responses in the treatment of disease.

BACKGROUND OF THE INVENTION

The human carcinoembryonic Ag (CEA)3 protein family encompasses several forms of proteins with different biochemical features. These proteins are encoded by 29 genes tandemly arranged on chromosome 19q13.2. CEA family genes have been classified into two major subfamilies, the CEA cell adhesion molecule (CEACAM) and the pregnancy-specific glycoprotein subgroups. The CEACAM proteins, which are part of the larger Ig superfamily, include CEACAM1, -3, -4, -5, -6, -7, and -8. They share a common basic structure of sequentially ordered different Ig-like domain(s) and are able to interact with each other. For example, it has been reported that various CEACAM proteins, such as CEACAM1 or CEACAM5, exhibit both homophilic and heterophilic interactions.

CEACAM1 (CD66a), a transmembrane protein and member of the carcinoembryonic Ags family, contains two ITIM sequences located within its cytosolic tail. CEACAM1 interacts with other known CD66 proteins, including CD66a, CD66c, and CD66e proteins. It is expressed on a wide spectrum of cells, ranging from epithelial to hemopoietic origin. Among CD66 proteins tested, only the CD66a protein is expressed on the surface of activated CD16-negative NK cells.

The various CEACAM proteins have different biochemical features, including but not limited to anchorage to cell surface (GPI-linked, transmembrane or secreted forms), length of cytoplasmic tail (long or short), and the presence or absence of various signal transduction motifs. These proteins are actively involved in numerous physiological and pathological processes.

CEACAM1 is a transmembrane protein that can be detected on some immune cells as well as on epithelial cells. Many different functions have been attributed to the CEACAM1 protein. It was shown that the CEACAM1 protein exhibits antiproliferative properties in carcinomas of colon, prostate, as well as other types of cancer. Additional data support the central involvement of CEACAM1 in angiogenesis and metastasis. CEACAM1 also has a role in the modulation of innate and adaptive immune responses. The present inventor has shown that CEACAM1 homophilic interactions inhibit NK-mediated killing activity independently of MHC class I recognition. This novel mechanism plays a pivotal role in the inhibition of activated decidual lymphocytes in vitro and most likely also in vivo after infection, including for example CMV infections. The CEACAM1 homophilic interactions are possibly important in some cases of metastatic melanoma, as increased CEACAM1 expression was observed on NK cells derived from some patients compared with healthy donors. There is an association of CEACAM1 expression on primary cutaneous melanoma lesions with the development of metastatic disease and poor survival. The present inventor has demonstrated the role of CEACAM1-mediated inhibition in maintaining NK self-tolerance in TAP2-deficient patients. Additional reports have indicated that CEACAM1 engagement either by TCR cross-linking with mAb or by *Neisseria gonorrhoeae* Opa proteins inhibits T cell activation and proliferation.

The CEACAM1 protein interacts with other CEACAM protein family members, such as CEACAM1 itself and CEACAM5. At least part or the entire binding site of human CEACAM1 is located at the N-terminal Ig-V-type domain of the CEACAM1 protein. In particular, amino acids 39V and 40D and the salt bridge between 64R and 82D may play an important role in this binding. Most amino acid sequences of the N-terminal domain of CEACAM1, -3, -5, and -6 are identical, and predicted binding residues are conserved among the four proteins. These proteins might interact with each other. This is of particular importance, because in certain tumors the CEACAM1 protein is down-regulated, followed by upregulation of CEACAM6 protein expression.

The present inventor has demonstrated the inability of CEACAM1 to bind CEACAM6. The present inventor has also directly shown that the presence of both residues 43R and 44Q in the CEACAM1 is crucial for the homophilic CEACAM1 interaction and that substitution of these residues with the 43S and 44L residues that are present in CEACAM6 abolishes the inhibitory effect. The reciprocal substitution of 43S and 44L of CEACAM6 to the 43R and 44Q residues, respectively, results in the gain of inhibitory heterophilic interactions with the CEACAM1 protein. The dichotomy of CEACAM family members by recognition of CEACAM1 is determined by the presence of R and Q at positions 43 and 44.

Natural killer (NK) cells belong to the innate immune system and efficiently kill virus-infected and tumor cells. NK killing is generally restricted mainly to cells that have lost class I MHC expression, a phenomenon known as the missing self. NK cell cytotoxicity is tightly regulated by various inhibitory class I MHC-recognizing receptors. The inhibitory signal is delivered via the immuno-receptor tyrosine-based inhibitory motif (ITIM) sequences found within the cytosolic tail of these receptors. Families of class I MHC binding inhibitory receptors include members of the Ig superfamily, namely killer Ig-related two-domain long-tail (p58) and three-domain long-tail (p70) receptors, the C-type lectin complex CD94/NKG2A, and the leukocyte Ig-like receptor (Ig-like transcript) family.

There are also other NK-specific receptors, termed natural cytotoxicity receptors (NCRs), which are directly involved in triggering NK cell cytotoxicity. The NCR group consists of several proteins, including NKp30, NKp44, NKp46, NKp80, and CD16. The cellular lysis ligands for all the NCRs have yet to be identified. A viral ligand (hemagglutinin) was shown to interact with the NKp46 receptor, and this interaction resulted in the enhancement of lysis of certain virus-infected cells. Indeed, the killing activity of target cells by human natural killer (NK) cells is mediated via a panel of lysis receptors of which is included CD16, NKp30, NKp44, NKp46, and NKG2D. These receptors recognize viral ligands such as hemagglutinin, stress-induced ligands such as MHC class I chain-related antigen A (MICA) and MICB, or other as-yet-undefined, cellular ligands. As mentioned, cells are protected from lysis by NK cells mainly owing to the interactions between class I MHC proteins and the appropriate inhibitory NK receptors.

The present inventor has identified a novel class I MHC-independent inhibitory mechanism of human NK cytotoxicity, mediated via the carcinoembryonic antigen-related cell adhesion molecule 1 (CEACAM1) homophilic interactions. Furthermore, the present inventor has found that the CEACAM1 protein plays a pivotal role in the inhibition of killing, proliferation, and cytokine secretion of interleukin 2 (IL-2)-activated decidual NK, T, and NKT cells, respectively.

Once class I MHC proteins are removed from the cell surface, these cells become susceptible to NK cell attack. It was surprising to learn that patients with transporter associated with antigen processing (TAP2) deficiency do not frequently suffer from autoimmune manifestations at early stages of their life. Activated NK cells derived from such patients may either be expressing an unknown inhibitory mechanism or are missing an unidentified lysis receptor. NK tolerance toward self-cells might be controlled by similar mechanisms.

The present inventor has demonstrated that the expression of the NKp46 receptor is severely impaired in a newly identified TAP2-deficient family and that the vast majority of activated NK cells derived from these patients use the CEACAM1 protein interactions to avoid tumor and autologous cell killing.

The present inventor has also found that CD16-negative NK clones inefficiently kill 1106mel cells because of the CD66a homotypic interactions The inhibition of NK cell cytotoxicity by CD66a was dependent on the level of CD66a expression on both effector and target cells. 721.221 cells expressing CD66a protein were protected from lysis by CD66a-expressing NK and YTS cells. Redirected lysis experiments performed by the present inventors showed that the strength of the inhibition is dependent on the level of CD66a expression on NK cells. A dramatic increase in CD66a expression was observed among NK cells isolated from melanoma patients. As stated above, a novel class I MHC-independent inhibitory mechanism of human NK cell cytotoxicity has been demonstrated by the present inventors. Some melanoma tumors may use this mechanism to avoid attack by NK cells.

Human natural killer (NK) cells are able to eliminate a broad spectrum of tumors and virus-infected cells by using several receptors, such as CD16, NKp30, NKp44, NKp46 and NKG2D. These receptors recognize either viral ligands, such as hemagglutinin, stress induced ligands, such as MICA and MICB, or other yet-undefined cellular ligands. Other NK receptors mediate inhibition of the killing activity following interaction with MHC class I proteins present on normal cells. Removal of MHC class I proteins from the cell surface renders it susceptible to NK cell attack through the phenomenon known as the "missing self".

Additional receptors are also able to manipulate NK cell cytotoxicity and the present inventors have shown a novel MHC class I independent inhibitory mechanism of human NK cytotoxicity that is mediated by the CEACAM1 homophilic interactions. This CEACAM1-mediated inhibition might play an important role in the in vivo development of melanoma in human patients. A 10-year follow-up study correlated the presence of CEACAM1 on primary melanoma lesions with poor survival. In addition, the present inventors have demonstrated the pivotal role of the CEACAM1 in the inhibition of killing, cytokine secretion and proliferation of activated decidual NK, NKT and T cells, respectively. The present inventors have also provided substantial evidence for a major role of the inhibitory CEACAM1 interactions in controlling NK cell autoreactivity in TAP2-deficient patients.

The presence of human soluble CEACAM1 protein can be observed in the serum of healthy donors. Furthermore, variations in serum levels of the soluble CEACAM1 protein are observed in various pathologies. For example, increased CEACAM1 levels were observed in the sera of patients with various hepatic diseases such as obstructive jaundice, primary billiary cirrhosis, autoimmune hepatitis and cholangiocarcinoma. A decrease in the soluble CEACAM1 level has not been reported.

The present inventor has shown that the soluble CEACAM1 protein blocks the CEACAM1-mediated inhibition of NK cell killing activity in a dose-dependent manner. Moreover, the present inventors have demonstrated that serum CEACAM1 levels among the TAP2-deficient patients are decreased when compared to normal individuals. These findings concur with the dominant role of the CEACAM1-mediated inhibition in controlling NK autoreactivity in TAP2-deficient patients. Thus, the maximal compensatory effect of CEACAM1-mediated inhibition is attained.

At least one object of the present invention is the modulation of CEACAM1 activity to effect control over the immune system and in particular specific immune responses in the treatment of disease. For example, at least one object of the present invention is the modulation of CEACAM1 activity in a population of tumor-infiltrating lymphocytes (TILs) to enhance the efficacy of TIL therapy in the treatment of cancer.

TIL cells can be removed from tumor samples taken from a patient and forced to reproduce by treating them with IL-2. When expanded and injected back into the patient, these cells may be active cancer fighters. [Rosenberg S A, Speiss P, Lafreniere R. *A new approach to the adoptive immunotherapy of cancer with tumor-infiltrating lymphocytes.* Science. 1986; 233:1318-1321. This reference is herein incorporated by reference.], [Rosenberg S A., et al., Use of tumor-infiltrating lymphocytes and interleukin-2 in the immunotherapy of patients with metastatic melanoma. A preliminary report. N Engl J Med. 1988 Dec. 22; 319 (25):1676-80. This reference is herein incorporated by reference.], [Rosenberg S A, Packard B S, Aebersold P M, et al. Use of tumor-infiltrating lymphocytes and interleukin-2 in the immunotherapy of patients with metastatic melanoma. A preliminary report. N Engl J Med 1988; 319:1676. This reference is herein incorporated by reference.], [Robert Dillman et al., Tumor-Infiltrating Lymphocytes and Interleukin-2: Dose and Schedules of Administration in the Treatment of Metastatic Cancer; Cancer Biotherapy & Radiopharmaceuticals. December 2004, Vol. 19, No. 6: 730-737. This reference is herein incorporated by reference.], and [Rosenberg S A, Speiss P, Lafreniere R. A new approach to the adoptive immuno-therapy of cancer with tumor-infiltrating lymphocytes. Science. 1986; 233:1318-1321. This reference is herein incorporated by reference.] The majority of the clinical data regarding TIL therapy comes from melanoma studies [Rosenberg S A, Packard B S, Arebersold P M, et al. Use of tumor infiltrating lymphocytes and interleukin-2 in the immunotherapy of patients with metastatic melanoma: a preliminary report. N Engl J Med. 1988; 319:1676-1680. This reference is herein incorporated by reference.] These studies show that TILs can circulate in patients for extended periods of time and that they selectively migrate to the tumor and sites of metastases.

Further limitations and disadvantages of conventional and traditional approaches will become apparent to one of skill in the art, though comparison of such systems with some aspects of the present invention as set forth in the remainder of the present application with reference to the drawings.

BRIEF SUMMARY OF THE INVENTION

One object of the present invention is to provide methods and compositions for the modulation of the immune system and/or one or more specific immune responses. Another object of the present invention is to provide methods and compositions for the regulation of lymphocyte activity. A still further object of the present invention is to provide methods and compositions for the regulation of the immune system and specific immune responses in the treatment of disease, including but not limited to cancer, autoimmune disease, and diseases requiring organ transplantation. Another object of the present invention is to provide methods and compositions for enhancing the efficacy of tumor-infiltrating lymphocyte (TIL) based therapy in the treatment of cancer. A further object of the present invention is to provide methods and/or compositions for inducing a tolerogenic state (immunologic tolerance) in a specified tissue, including but not limited to tissue affected by autoimmune disease or tissue being prepared for transplantation.

One or more of the preceding objects, or one or more other objects which will become plain upon consideration of the present specification, are satisfied by the invention described herein.

One aspect of the invention, which satisfies one or more of the above objects, is the functional modulation of at least one protein from the CEACAM protein family. Another aspect of the invention, which satisfies one or more of the above objects, is the functional modulation of the CEACAM1 (cd66a) protein. The functional modulation of CEACAM protein activity can be accomplished by any number of techniques know to those skilled in the art for the modulation of protein activity, including modulating protein concentration, stability and function. This can include but is not limited to the allosteric or non allosteric disruption of a homotypic or heterotypic protein-protein interaction, the modulation of gene expression, the modulation of processing and/or stability of mRNA, the modulation of mRNA translation (protein synthesis), the modulation of post translational protein modification, the modulation of protein stability, or the modulation of protein transport.

In another aspect of the present invention, the modulation of the immune system and/or one or more specific immune response comprises the disruption of a homotypic or heterotypic CEACAM family protein-protein interaction, including but not limited to the disruption of a homotypic or heterotypic CEACAM1 protein-protein interaction. This can be accomplished by any number of techniques know to those skilled in the art for disrupting protein-protein interactions, including but not limited to contacting at least one of the proteins involved in the CEACAM family protein-protein interaction, either at or away from the protein-protein interaction interface, with an inhibiting agent.

In yet another aspect of the present invention, the modulation of the immune system and/or one or more specific immune response comprises the modulation of CEACAM gene expression, including CEACAM1 gene expression. This can be accomplished by any number of techniques know to those skilled in the art for regulating gene expression, including but not limited to contacting a population of cells with a transcriptional activator or repressor, or other factor capable of inducing or inhibiting gene expression.

In another aspect of the present invention, the modulation of the immune system and/or one or more specific immune response comprises the modulation of CEACAM gene expression, including CEACAM1 gene expression. This can be accomplished by any number of techniques know to those skilled in the art for regulating gene expression, including but not limited to contacting a population of cells with a transcriptional activator or repressor, or other factor capable of inducing or inhibiting gene expression, including but not limited to a protein, peptide, nucleic acid, small molecule, or any combination thereof.

In still another aspect of the present invention, the modulation of the immune system and/or one or more specific immune response comprises the modulation of CEACAM protein synthesis or translation, including the modulation of CEACAM1 protein synthesis or translation. This can be accomplished by any number of techniques know to those skilled in the art for regulating protein synthesis or translation, including but not limited to contacting a population of cells with an antisense nucleic acid, or other factor capable of modulating protein synthesis, including but not limited to a protein, peptide, nucleic acid, small molecule, or any combination thereof.

BRIEF DESCRIPTION OF SEVERAL VIEWS OF THE DRAWINGS

FIG. 1. CEACAM1-Ig does not recognize the CEACAM6 protein. Stable 0.221/CEACAM1 and 0.221/CEACAM6 were generated as described. The expression level was monitored with the Kat4c mAb (empty histograms). Binding of CEACAM1 was assessed with the CEACAM1-Ig fusion protein (empty histograms). The reagents used are indicated in each histogram. The background (shaded histograms) is the corresponding staining of 0.221 parental cells. This figure shows one representative experiment of 20 performed.

FIG. 4. Sequence alignment of CEACAM family members, including: CEACAM1 (SEQ ID NO. 1); CEACAM3 (SEQ ID NO. 2); CEACAM5 (SEQ ID NO. 3); and CEACAM6 (SEQ ID NO. 4). Letters in bold indicate amino acid residue 1. Identical residues of the known motifs crucial for binding are underlined. Different residues in the binding motifs are highlighted with black (for RQ residues) or gray (for SL residues) backgrounds.

FIG. 18. Killing of PHA-induced T-cell blasts. (A) Staining of PHA-induced T-cell blasts with various mAbs. Staining of PHA-induced T-cell blasts derived from patient A and from the healthy sister was performed with the F(ab')$_2$ fragments of anti-CD3, anti-CEACAM1, and anti-MHC class I mAb HP-1F7. (B) Staining of PHA-induced T-cell blasts and of the LnCap cell line with various fusion proteins. Staining was performed with the NKp46-Ig, NKp30-Ig, NKp44-Ig, and the control CD99-Ig fusion proteins. (C) NK clones derived from patients A, B, and C were assayed for cytotoxic activity against autologous PHA-induced T-cell blasts. The NK clones obtained from the healthy sister were assayed against PHA-induced T-cell blasts derived from patient A. NK clones were preincubated with or without F(ab')$_2$ fragments of polyclonal anti-CEACAM or the control polyclonal antiubiquitin antibodies. The targets, autologous PHA-induced T-cell blasts, were incubated with or without the F(ab')$_2$ fragments of HP-1F7 or the control 12E7 mAb. Assays were performed at an E/T ratio of 2:1. Shown are the mean results of several NK clones that were obtained from 3 independent experiments. The data represent the mean percentage of killing±SD. (D) NK clones derived either from the healthy sister or from patients A, B, and C were assayed for killing of PHA-induced T-cell blasts derived from the healthy sister. NK clones and target PHA-induced T-cell blasts were pretreated as described for panel C. Assays were performed at an E/T ratio of 2:1. Shown are the mean results of several NK clones that were obtained from 3 independent experiments. All mAbs used were in the form of F(ab')$_2$. The data represent the mean percentage of killing±SD.

DETAILED DESCRIPTION OF THE INVENTION

Figure 2:
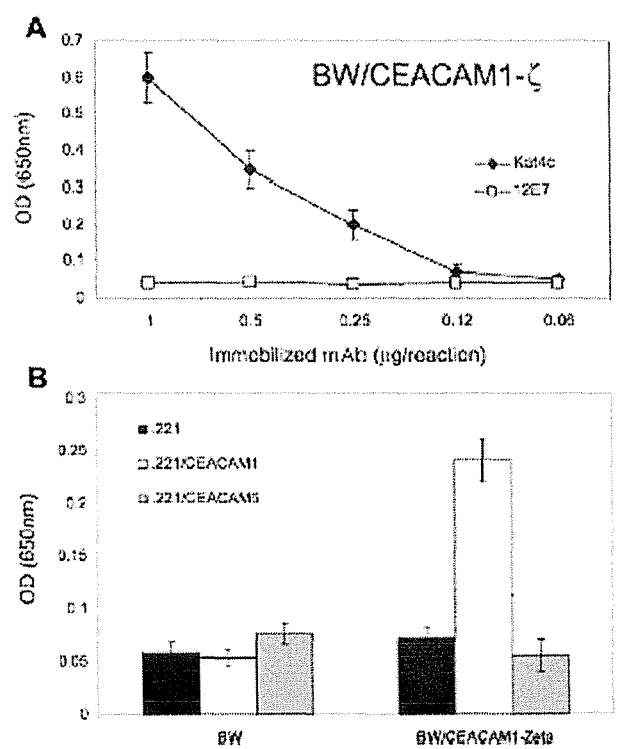
FIG. 2. CEACAM1 and the CEACAM6 proteins do not functionally interact. A, The amount of mIL-2 in culture supernatant of Kat4c treated and control 12E7 BW/CEACAM1-_ cells as measured by ELISA. The x-axis is the amount of immobilized mAb per reaction, and the y-axis is the optic density at a wavelength of 650 nm. This figure shows the mean of three independent experiments. B, mIL-2 secretion by BW parental cells or by BW/CEACAM1-_ cells co incubated for 48 h with irradiated 0.221, 0.221/CEACAM1, or with 0.221/CEACAM6 cells. The y-axis is the optic density at a wavelength of 650 nm. The average of four independent experiments is shown.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

The presently described technology relates to methods and compositions for the regulation of the immune system and specific immune responses, and in particular to methods and compositions for the regulation of lymphocyte activity. One aspect of the present invention is the functional modulation of at least one member of the CEACAM protein family, said CEACAM protein being either membrane bound or free. The CEACAM protein family, which are part of the larger Ig superfamily, include without limitation CEACAM 1, -3, -4, -5, -6, -7, and -8. The CEACAM protein family share a common basic structure of sequentially ordered different Ig-like domain(s) and are able to interact with each other.

In one embodiment of the presently described invention, regulation of the immune system and/or one or more specific immune responses is achieved by the functional modulation of a CEACAM protein family member, and in particular is achieved by modulating a CEACAM family protein-protein interaction function. The functional modulation of a member of the CEACAM protein family can comprise the disruption of a CEACAM family protein homotypic or heterotypic protein-protein interaction, and can comprise any member of techniques mow to those skilled in the art for the disruption of a protein-protein interaction. The negative modulation of a CEACAM family member protein function can include for example contacting the CEACAM family protein, or protein interacting with the CEACAM family protein, with a protein, peptide, peptidomimetic, nucleic acid, nucleic acid analog, small molecule, or any combination thereof having specificity for either the CEACAM family protein or a protein interacting with the CEACAM family protein, said specificity at or away from the interface of the protein-protein interaction.

In preferred embodiments of the present invention, regulation of the immune system and/or one or more specific immune responses is achieved by the negative modulation of CEACAM1 (cd66a) function. The negative modulation of CEACAM1 function can include but is not limited to the disruption of a CEACAM1 homotypic or heterotypic protein-protein interaction by contacting either CEACAM1 or a protein interacting with CEACAM1 with a protein, peptide, peptidomimetic, nucleic acid, nucleic acid analog, small molecule, or any combination thereof having specificity for either the CEACAM1 protein or a protein interacting with CEACAM1 in a protein-protein interaction of interest.

In one embodiment of the present invention, the agent employed to disrupt a CEACAM family protein-protein interaction in effecting control over a particular immune response has can be without limitation any reversible or non-reversible, competitive or non-competitive, inhibitor of the formation and/or maintenance of any homotypic and/or heterotypic protein-protein interaction that includes at least one CEACAM family protein. These agents include but are not limited to linear or cyclic nucleic acids, full-length proteins, protein structural or functional domains, smaller peptides, and peptidomimetic derivatives. The terms "amino acid sequence," "nucleic acid sequence," "protein," "polypeptide," "peptide" and "nucleic acid" include compositions of the invention that also include "analogs," or "conservative variants" and "mimetics" such as "peptidomimetics" with structures and activity that substantially correspond to the compound from which the variant was derived. These agents can be derived from any protein that participates in any CEACAM family homotypic and/or heterotypic protein-protein interaction, or any other protein including but not limited to immunoglobins having binding specificity to a CEACAM family protein.

In one embodiment of the present invention, the agent employed to disrupt a CEACAM family protein-protein interaction in effecting control over a particular immune response comprises a full length CEACAM family protein, or a fragment derived therefrom. CEACAM family proteins that can be used as include but are not limited to the CEACAM1 protein represented by SEQ ID No. 1; the CEACAM3 protein represented by SEQ ID No. 2; the CEACAM5 protein represented by SEQ ID No. 3; the CEACAM6 protein represented by SEQ ID No. 4; and the CEACAM8 protein. In another embodiment of the present invention, the agent employed to disrupt a CEACAM family protein-protein interaction to effect control over a particular immune response can comprise any immunoglobulin, or fragment thereof, specific for the CEACAM family protein or protein interacting with the CEACAM family protein.

In still another embodiment of the present invention, the agent employed to disrupt a CEACAM family protein-protein interaction in effecting control over a particular immune response comprises a small molecule compound. The term "small molecule" means any synthetic small molecule, such as an organic molecule, inorganic molecule, or synthetic molecule, such as those generated by combinatorial chemistry methodologies. These small molecules can be synthesized using a variety of procedures and methodologies, which are well described in the scientific and patent literature, e.g., Organic Syntheses Collective Volumes, Gilman et al. (Eds) John Wiley & Sons, Inc., NY; Venuti (1989) *Pharm Res.* 6:867-873. Synthesis of small molecules, as with all other procedures associated with this invention, can be practiced in conjunction with any method or protocol mown in the art. For example, preparation and screening of combinatorial chemical libraries are well known, see, e.g., U.S. Pat. Nos. 6,096, 496; 6,075,166; 6,054,047; 6,004,617; 5,985,356; 5,980,839; 5,917,185; 5,767,238.

In another embodiment of the present invention, the agent employed to disrupt a CEACAM family protein-protein interaction in effecting control over a particular immune response comprises a multimer agent comprising at least two or more agents according to the present invention, linked together. The agents, linked together to form the multimer agent, can be identical or different, and can include but are not limited to any combination protein, nucleic acid, small molecules, or derivatives thereof.

In another embodiment of the presently described invention, regulation of the immune system and/or one or more specific immune responses comprises the negative or positive modulation of CEACAM1 gene expression or translation of CEACAM1 mRNA. The modulation of CEACAM1 gene expression or CEACAM1 mRNA translation can comprise any number of techniques know to those skilled in the art for the modulation of gene expression, and can involve contacting any environment with a protein, peptide, peptidomimetic, nucleic acid, nucleic acid analog, small molecule, or some combination thereof.

In a further aspect of the presently described invention, there are provided methods and/or compositions for modulating the immune system and/or one or more specific immune responses in the course of treating a disease. Exemplar diseases include cancers, autoimmune conditions, and those diseases requiring tissue transplantation.

Certain aspects of the present invention can be performed in any environment including but not limited to in situ, in vivo, or in vitro environments. For example, the methods and/or compositions of the present invention can be employed in a cell culture or in the living body of an animal, such as a human.

One aspect of the present invention provides methods and/or compositions for enhancing the efficacy of tumor-infiltrating lymphocyte (TIL) therapy in the treatment of cancer. In one embodiment of this aspect of the present invention, the efficacy of TIL, therapy for the treatment of cancer is enhanced by the negative modulation of the functional activity of at least one member of the CEACAM protein family. In one preferred embodiment of this aspect of the present invention, the efficacy of TIL therapy for the treatment of cancer is enhanced by the negative modulation of CEACAM1 protein functional activity. The negative modulation of the at least one member from the CEACAM protein family, including but not limited to the CEACAM1 protein, can be accomplished by any number of techniques know to those skilled in the art for the negative modulation of protein function, including but not limited to the allosteric or non allosteric disruption of a homotypic or heterotypic protein-protein interaction.

In one preferred aspect of the present invention, the efficacy of TIL therapy for the treatment of cancer is enhanced by the negative modulation of CEACAM1 (cd66a) protein function in a population of tumor-infiltrating lymphocytes. In one embodiment of this aspect of the present invention, the efficacy of TIL therapy for the treatment of cancer is enhanced by the disruption of a homotypic and/or heterotypic CEACAM1 protein-protein interaction by contacting a population of tumor-infiltrating lymphocytes with CEACAM1 selective binding elements.

In a still further aspect of the presently described invention, methods and/or materials are provided for inducing a tolerogenic state (immunologic tolerance) in a specified tissue. As used herein, one exemplar definition for tissue includes any aggregate of cells. The specified tissue may include tissue affected by an autoimmune disease or tissue being prepared for transplantation. In one preferred embodiment thereof, the induction of the tolerogenic state includes the stimulation of CEACAM1 gene expression and protein production. This can be accomplished by any number of techniques know to those skilled in the art for the enhancement of gene expression and protein production.

An additional aspect of the present invention provides for immuno-conjugates selectively targeting the CEACAM1 protein and cells expressing CEACAM1 protein in the treatment of cancer. One exemplar definition of immuno-conjugate is a complex of an antibody (or any derivative of an antibody that retains binding specificity) and any agent capable of altering the state of a cell displaying the antigen recognized by the antibody. For example, the agent may be cytotoxic or cytostatic. A cytotoxic agent would kill or destroy a cell, and a cytostatic agent would inhibit or prevent cellular proliferation. For example, one embodiment of this aspect of the present invention comprises contacting a cancer cell membrane bound CEACAM1 with a CEACAM1 protein-binding element conjugated to a moderator of cellular metabolism.

The moderator of cellular metabolism may be a protein, peptide, peptidomimetic, nucleic acid, nucleic acid analog, small molecule drug, or some combination thereof. Modulation of cellular metabolism include, for example, the addition of moderators that directly regulate cellular metabolism, or elements that regulate the function of other factors involved in the control of cellular metabolism. Aspects of cellular metabolism that may be modulated can include, for example, nucleic acid metabolism, protein metabolism, cell proliferation, immunity, or any combination thereof. Examples of nucleic acid metabolism include DNA metabolism and RNA metabolism. DNA metabolism includes, for example, DNA synthesis, the initiation of DNA synthesis, or purine and/or pyrimidine biosynthesis. RNA metabolism includes, for example, RNA synthesis, aspects of transcriptional regulation (e.g.—activation or repression of gene expression), and/or RNA processing (e.g.—RNA splicing and transport). Protein metabolism includes, for example, protein synthesis (translation), protein folding, protein translocation, post-translational modification of proteins, protein export, and/or amino acid biosynthesis. Cell proliferation includes, for example, regulation of the cell cycle, and may also include regulation of programmed cell death (apoptosis).

Another embodiment of this aspect of the present invention comprises contacting cancer cell membrane bound CEACAM1 with a cancer therapeutic agent conjugated via a linker moiety to a CEACAM1 selective antibody. The linker moiety can be designed so that the cancer therapeutic agent remains stable or inactive while in circulation, but is rapidly released once the conjugate binds to a tumor-specific antigen (such as CEACAM1) expressed on the surface of a cancer cell and enters the cytosol. The therapeutic agent can be a toxin that will kill the cancer cell. For example, the toxin may disrupt an essential metabolic process. Toxins can be of plant or bacterial origin, (e.g., ricin and diphtheria toxin).

Another embodiment of the present invention comprises immuno-conjugates that consist of monoclonal antibodies specific to CEACAM1 that are conjugated to small highly cytotoxic drugs such as taxoids that inhibit microtubule depolymerization. Tumor-activated pro-drugs can be used in which the cytotoxic agent conjugated to the antibody is rendered non-cytotoxic to cells that lack the target antigen. Because the linker that connects the antibody to the drug is stable in the blood, the drug immuno-conjugate is nontoxic until it reaches the tumor site. Internalization of the immuno-conjugate triggers release of the drug and potent killing of the target cell.

A still further embodiment of the present invention comprises the use of radioimmunoconjugates selective to CEACAM1 that can be employed both as imaging agents and therapeutic agents. Radioisotopes that emit alpha or beta particles may be used. in particular, radioisotopes that emit alpha particles are effective because of a shorter path length (less bystander killing) and higher energy transfer (more cytotoxic).

The present invention also includes any moderator of cellular metabolism conjugated to an entity capable of selectively binding CEACAM1 or a binding partner of CEACAM1. For example, cellular metabolism may include nucleic acid metabolism, protein metabolism, or both. Nucleic acid metabolism, for example, will include aspects of DNA synthesis, transcription, RNA processing, or some combination thereof. Protein metabolism, for example, will include aspects of protein synthesis (translation), and/or protein modification (either post translational or concomitant with translation).

An additional embodiment of the present invention comprises contacting the CEACAM1 protein, either membrane bound or free from membrane, with a CEACAM1 binding element (e.g. an antibody specific for CEACAM1) conjugated to a detectable moiety, including for example, a fluorescent or radioactive moiety. The target CEACAM1 protein can exist either in the body of a living animal (e.g. a human), or outside the living body as a biological sample including but nor limited tom urine or blood serum samples.

A further aspect of the present invention provides for enhancing the efficacy of adaptive immunotherapy. One aspect of adaptive immunotherapy includes a treatment especially for cancer in which lymphocytes are removed from a patient, cultured with interleukin-2 to induce their transformation into lymphokine-activated killer cells, and returned to the patient's body along with interleukin-2.

The present invention provides for enhancing the efficacy of Tumor Infiltrating Lymphocyte based therapy in the treatment of cancer. This aspect of the present invention includes the modulation of CEACAM1 function in a population of Tumor Infiltrating Lymphocytes. The method comprises the disruption of a CEACAM1 protein-protein interaction, that can be either homotypic or heterotypic. The method can also comprise, the negative modulation of CEACAM1 gene expression and/or translational efficiency in a population of Tumor Infiltrating Lymphocytes.

Another aspect of the present invention provides for enhancing the efficacy of Tumor Infiltrating Lymphocyte based cancer therapy by enriching a Tumor Infiltrating Lymphocyte cell population for cells lacking CEACAM1. This aspect of the invention can be achieved, for example, by either employing a screening or selection approach. For example, a screening approach might include contacting a TIL cell population with a CEACAM1 specific binding element (such as an antibody) conjugated to a detectable moiety (such as a fluorescent or radioactive probe), followed by subjection to a cell sorting methodology to separate cells expressing CEACAM1 from those lacking CEACAM1. Alternatively, a selection approach may be employed such as affinity purification. For example, a TIL cell population might be subjected to affinity chromatography purification employing a column made with a specific CEACAM1 binder (for example antibodies specific to CEACAM1). Cells flowing thru the column should be enriched for cells lacking CEACAM1. As an alternative to column affinity chromatography, a batch approach can be employed whereby a specific CEACAM1 binder (including antibodies specific to CEACAM1) is linked to a pull down moiety, such as a magnetic bead. A streptavidin/avidin pull down method can also be employed. In principle, to facilitate removal of cells expressing CEACAM1 from a TIL population, any binding partner can be employed in either an affinity column chromatography or affinity batch pull down protocol so long as one of the pair is conjugated to a CEACAM1 specific binding element. An alternative selection method includes contacting a TIL population with an immuno-conjugate composed of a CEACAM1 specific immunoglobulin (such as an antibody or antibody fragment) linked to a cytotoxic agent, thereby selectively killing those cells having surface expressed CEACAM1 and in turn enriching the TIL population for cells lacking CEACAM1.

At least one of the objects of the present invention includes inducing a tolerogenic state in a specified tissue. This aspect of the present invention for example includes the induction of CEACAM1 protein production. The specified tissue may be tissue affected by an autoimmune disease or tissue being prepared for transplantation. The induction of CEACAM1 protein production includes, for example, the generation of CEACAM1 gene expression. In at least on aspect of the present invention, induction of CEACAM1 protein production includes the transfer of genetic material into the cells of the specified tissue for which a protective immunity is to be generated. The genetic material, for example, can be composed of a CEACAM1 family gene. Cis acting genetic elements may also be added to facilitate, for example, the integration of the genetic material into the genome of the specified cells, or the production of CEACAM1 protein, or both. The cis acting genetic elements may include genetic material effective in inducing efficient gene expression, efficient translation, increased recombination frequency, increased targeted recombination, or some combination thereof.

In an additional aspect of the invention, materials and/or methods are provided for inducing a protective immunity in a specified tissue, which includes the induction of CEACAM1 protein production by transferring genetic material that includes a gene whose protein product induces the increased production of a CEACAM1 family protein. For example, the gene whose protein product induces the increased production of a CEACAM1 family protein may be a transcription factor, including for example a transcriptional activator.

One aspect of the present invention provides methods and/or materials for imparting a tolerogenic state (i.e.—immunologic tolerance) upon a specified tissue. One embodiment of this aspect of the present invention provides methods and/or materials for imparting a tolerogenic state upon a specified tissue by imparting upon or inducing within a specified tissue CEACAM1 function. The specified tissue may be any tissue upon which it is desirable to create a tolerogenic state. For example, the tissue may be tissue that is being prepared for transplantation, or the tissue may be tissue which is afflicted by autoimmune disease. One definition of a tolerogenic state is a state characterized by an immunologic tolerance.

A further aspect of the present invention provides methods and/or materials for preparing tissue for grafting or transplantation. In one embodiment, the present invention provides materials and/or methods for mitigating the potential for immunological rejection of grafted or transplanted tissue. For example, the present invention provides for increased transplant tolerance strategies that would thwart the immunological rejection of transplanted or grafted tissue by imparting upon the transplanted tissue a tolerogenic state (immunologic tolerance), while preserving a body's general immune competence, including for example normal immune responses to pathogens and cancer risks. This aspect of the present invention may be accomplished, at least in part, by conveying or imparting CEACAM1 function or activity upon tissue to be transplanted or grafted. For example, tissue to be transplanted or grafted can be transformed or transfection of with genetic material effective in facilitating or inducing the production of CEACAM1 protein. This can be performed, for example, by the transfer of genetic material that is effective in inducing CEACAM1 protein production to tissue being prepared for transplantation or grafting. The genetic material that is transferred may include, for example, one or more functional CEACAM1 family genes, or some derivative thereof, including for example genetic material encoding specific CEACAM1 protein domains. The genetic material may also contain any cis acting genetic elements that may augment CEACAM1 protein production, including for example genetic elements that facilitate transcription (gene expression) and/or translation (protein synthesis). The transfer of genetic material may be accomplished by any method known in the art.

One exemplar aspect of transplantation includes an act, process, or instance of transplanting tissue; especially the removal of tissue from one part of the body or from one individual and its implantation or insertion in another especially by surgery. The transplantation of tissue can be allogeneic (allograft), which includes transplantation of tissue between genetically different members of the same species. For example, nearly all organ and bone marrow transplants are allografts. These may be between brothers and sisters, parents and children, or between donors and recipients who are not related to each other. The transplantation can also be autologous (autograft), which includes transplantation of an organism's own tissues. A graft or transplantation of tissue from one site to another on the same individual is called an autograft. Autologous transplantation may be used to repair or replace damaged tissue. For example, autologous bone marrow transplantation permits the usage of more severe and toxic cancer therapies by replacing bone marrow damaged by the treatment with marrow that was removed and stored prior to treatment. The transplantation of tissue can also be syngeneic, which includes transplantation of tissue between genetically identical members of the same species (e.g., identical twins). The transplantation can also be xenogeneic (xenograft), which includes transplantation between members of different species; for example, the transplantation of animal tissues into humans.

One exemplar characterization of immunological rejection of transplanted tissue includes include those events by which a body's immune system attacks transplanted or grafted tissue, reacting to them as if they were harmful. Graft or transplant rejection generally involves the destruction of the grafted or transplanted tissue by attacking lymphocytes. In clinical transplantation, the types of transplant rejection may be classified into three main types: hyperacute, acute, and chronic.

The present invention also provides materials and/or methods for imparting a tolerogenic state upon engineered tissues. This aspect of the present invention can be achieved, at least in part, by imparting upon the engineered tissue CEACAM1 protein function. For example, one embodiment of the present invention involves the purification of a specific cell type of interest, followed by a transformation of the cell to produce CEACAM1 protein. These cells are then expanded in cell culture and seeded onto a scaffold of any desirable shape or rigidity prepared from a suitable biomaterial (or biocompatible material, or some combination) to form a scaffold/biological composite, or tissue engineered construct, that has decrease susceptibility to immunological rejection upon transplantation or grafting as replacement tissue.

A further aspect of the present invention provides methods and/or materials for imparting a tolerogenic state to tissue afflicted by autoimmune disease, while preserving a body's general immune competence, including for example normal immune responses to pathogens and cancer risks. This aspect of the present invention may be accomplished, at least in part, by conveying or imparting CEACAM1 function or activity upon tissue afflicted by autoimmune disease. For example, the present invention provides for the targeted transformation of tissue afflicted by autoimmune disease to express CEACAM1 protein. This can be accomplished, for example, by transfer of genetic information effective in inducing CEACAM1 protein production directly to tissue afflicted with an autoimmune disease, subsequent to any required exposure of the afflicted tissue. The genetic material that is transferred may include, for example, one or more functional CEACAM1 family genes, or some derivative thereof, including for example genetic material encoding specific CEACAM1 protein domains. The genetic material may also contain any cis acting genetic elements that may augment CEACAM1 protein production, including for example genetic elements that facilitate transcription (gene expression) and/or translation (protein synthesis). The transfer of genetic material may be accomplished by any method known in the art, and may be performed subsequent to exposure of the afflicted tissue by surgery, or if surgery is not an option, the effected tissue may be targeted utilizing receptor-mediated gene transfer technology.

Autoimmune diseases are generally characterized by the body's immune responses being directed against its own tissues, causing prolonged inflammation and subsequent tissue destruction. For example, autoimmune disorders can cause immune-responsive cells to attack the linings of the joints—resulting in rheumatoid arthritis—or trigger immune cells to attack the insulin-producing islet cells of the pancreas leading to insulin-dependent diabetes. A healthy immune system recognizes, identifies, remembers, attacks, and destroys bacteria, viruses, fungi, parasites, and cancer cells or any health-damaging agents not normally present in the body. A defective immune system, on the other hand, directs antibodies against its own tissues. Any disease in which cytotoxic cells are directed against self-antigens in the body's tissues is considered autoimmune in nature. Such diseases include, but are not limited to, celiac disease, Crohn's disease, pancreatitis, systemic lupus erythematosus, Sjogren's syndrome, Hashimoto's thyroiditis, and other endocrinopathies. Allergies and multiple sclerosis are also the result of disordered immune functioning.

Examples of different types of viruses used as vectors for the transfer of genetic material include, without limitation: retroviruses; adenoviruses; adeno-associated viruses; and herpes simplex viruses. Besides virus-mediated genetic material delivery systems, there are several nonviral options for delivery. The simplest method is the direct introduction of the genetic material into target cells. Another nonviral approach involves the creation of an artificial lipid sphere with an aqueous core. This liposome, which carries the genetic material, is capable of passing the genetic material though the target cell's membrane. Genetic material can also get inside target cells by chemically linking the genetic material to a molecule that will bind to special cell receptors. Once bound to these receptors, the genetic material constructs are engulfed by the cell membrane and passed into the interior of the target cell.

Particle mediated transfer of genetic material is also a viable method to introduce genetic material according to some aspects of the present invention. Any method regarding the particle mediated transfer of genetic material known in the art may be used. For example, the gene gun is part of a method sometimes called the biolistic (also known as bioballistic) method. Under certain conditions, DNA (or RNA) becomes "sticky," adhering to biologically inert particles such as metal atoms (usually tungsten or gold). By accelerating this DNA-particle complex in a partial vacuum and placing the target tissue within the acceleration path, DNA is effectively introduced (Gan, Carol. "Gene Gun Accelerates DNA-Coated Particles To Transform Intact Cells". *The Scientist*; Sep. 18, 1989, 3[18]:25. This reference is herein incorporated by reference). Uncoated metal particles could also be shot through a solution containing DNA surrounding the cell thus picking up the genetic material and proceeding into the living cell. A perforated plate stops the shell cartridge but allows the slivers of metal to pass through and into the living cells on the other side. The cells that take up the desired DNA, identified through the use of a marker gene (in plants the use of GUS is most common), are then cultured to replicate the gene and possibly cloned. The biolistic method is most useful for inserting genes into plant cells such as pesticide or herbicide resistance. Different methods have been used to accelerate the particles: these include for example pneumatic devices; instruments utilizing a mechanical impulse or macroprojectile; centripetal, magnetic or electrostatic forces; spray or vaccination guns; and apparatus based on acceleration by shock wave, such as electric discharge.

One aspect of the following invention provides for the manipulation of information metabolism in a specified target cell. One exemplar description of information metabolism includes without limitation those processes that are generally regarded as involving those processes by which cells receive, process, and respond to information from the environment. For example, information metabolism will include those processes associated with signal transduction. Signal transduction includes, without limitation, the transfer of information from the environment to the cell's interior. This is generally mediated for example by the initial reception of an environmental signal or stimulus by a cell-surface component, such as a receptor protein, followed by the transduction of that signal via one or more of the signal-transduction pathway(s). One exemplar description of signal-transduction pathways includes those processes and components that mediate the sensing and processing of signals or stimuli. For example, these pathways may be thought of as molecular circuits that can, without limitation, detect, amplify, and/or integrate diverse external signals to generate responses that change the biochemistry of the cell. Such changes might include changes in enzyme activity, gene expression, protein synthesis, energy metabolism, immunity, cell proliferation, cell viability, and/or ion-channel activity.

At least one aspect of the invention provides for the manipulation of information metabolism in a specified target cell achieved by the modification of that target cell to produce a chimeric receptor protein that has a combination of functional and/or structural domains that are not found in nature. This aspect of the invention can be achieved by performing a receptor domain swapping exercise in combination with either selecting or screening for a desired phenotype. In general, cell-surface receptors are membrane bound, and composed of an ectodomain(s) (or extracellular domain(s)), a membrane spanning domain(s), and an intracellular domain(s). The extracellular domain generally has a binding site that specifically recognizes a specific signal molecule (often referred to as the ligand). In an exemplar case, the interaction of the ligand and the extracellular domain(s) of the receptor alters the tertiary or quaternary structure of the receptor, including the intracellular domain(s), the consequence of which may include the elicitation of a signal transduction pathway that results in some change in cellular activity. One additional exemplar characterization of information metabolism includes those processes which are generally regarded as involving first the reception of an environmental signal by an extracellular domain of a cell-surface receptor, followed by the transduction of that signal mediated at least in part, through the interaction of an intracellular domain of the cell-surface receptor with one or more components of one or more of a signal-transduction pathway(s). One exemplar characterization of signal transduction is any process by which a cell converts one kind of signal or stimulus into another. Processes referred to as signal transduction often involve, without limitation, a sequence of biochemical reactions inside the cell, which are carried out by enzymes and linked through second messengers. For example, in many transduction processes, an increasing number of enzymes and other molecules become engaged in the events that proceed from the initial stimulus (e.g. binding of a ligand to a receptor). These chains of steps can also be referred to as a "signalling cascade" or "second messenger pathway" and the result is that a small stimulus elicits a large response.

At least one of the aspects of the present invention provides for engineered adoptively transferred immune elements. One exemplar definition of immune element as used herein includes any element of the immune system, including without limitation lymphocytes. For example, immune elements can be engineered to express a CEACAM1-recognizing element (CEACAM1 itself, derivatives of CEACAM1, anti- CEACAM1 antibody, anti-CEACAM1 scFv, other CEACAM1-recognizing elements like specific peptoids, CEACAM5, derivatives of CEACAM5) fused to a molecular module capable of transducing activating signals to effector functions.

A further aspect of the present invention provides for the change, alteration, or modulation of the response that a specific signal or stimulus produces upon reception by the ectodomain of a cell surface receptor. For example, a signal or stimulus that is generally regarded as producing a response that activates some aspect of cellular metabolism can be made to inhibit the same or a different aspect of cellular metabolism. Likewise, a signal or stimulus that is generally regarded as producing a response that inhibits some aspect of cellular metabolism can be made to activate the same or a different aspect of cellular metabolism. Moreover, a signal or stimulus that produces a response that activates a specific aspect of cellular metabolism can be made to activate a different aspect of cellular metabolism. Likewise, a signal or stimulus that produces a response that inhibits a specific aspect of cellular metabolism can be made to inhibit a different aspect of cellular metabolism. Also, the intensity with which a signal or stimulus produces either an activating or inhibitory response can be either positively or negatively modulated. As used herein, one exemplar definition of cellular metabolism includes any and all of the chemical processes occurring within a cell or organism that are associated with the maintenance of life.

At least one object of the present invention is achieved by fusing a known receptor ligand binding ectodomain with a receptor adaptor portion, to form a combination not seen in nature, and resulting in the change, alteration, or modulation of the cellular response usually associated with the ligand binding to the selected ectodomain. For example, the present invention provides a chimeric construct made by fusing an ectodomain to an adaptor portion that transduces signals different from those usually transduced upon ligand binding to the selected ectodomain. In this fashion, the response usually generated with ligand binding to the selected ectodomain can be change, altered, or modulated. This chimeric construct can be transferred into an adoptively transferred immune element, including without limitation TIL (prior to injection), or in vivo as a genetic therapy to a designated cell population of interest. The genetic construct can be cloned into any appropriate expression vector, which is suitable for transfection of cells such as primary lymphocytes and suitable for human use. These include, for example and without limitation, retroviral vectors, such as pMSGV1 (a derivative of the vector pMSGV (murine stem cell virus (MSCV)-based splice-gag vector), which was generated from pMINV. Other expression systems might be used as well.

One exemplar embodiment of the present invention is achieved by providing a chimeric construct made with at least an ectodomain capable of binding CEACAM1 fused to at least an adaptor portion that transduces activating signals to facilitate effector cellular functions. The resultant cellular response is different from what is normally associated with CEACAM1 activation, and may include without limitation any change, alteration, or modulation in cellular metabolism or activity. This construct can be transferred into an adoptively transferred immune element such as TIL (prior to injection), or in vivo as a genetic therapy to a designated cell population of interest.

Exemplar ectodomains include, without limitation, CEACAM1 whole protein, CEACAM1 subdomains, peptides derived of CEACAM1, peptoids, anti-CEACAM1 mAb, anti-CEACAM1 scFv, CEACAM5 (CEA), CEACAM5 subdomains, peptides derived of CEACAM5.

Exemplar adaptor portions include, without limitation, those capable of transporting or transducing signals that will activate the effector functions of cells. Exemplar cells include, without limitation, immune cells or any other cell afflicted with a disease state. Exemplar disease states include, without limitation, cancer and autoimmune diseases.

Exemplar adaptor portions will include, without limitation, at least one of the transmembrane and/or cytosolic portions of known adaptor proteins that transduce activating signals. These proteins include, for example, human zeta chain, DAP10, DAP12, Fc☐RI and LAT. It is also possible to use the transmembrane and cytosolic tail of other proteins that bear ITAM sequences, such as CEACAM3 and FCgRII (CD32).

The following invention also provides for the control and/or modulation of a cellular signal transduction pathway(s) designed to transduce and amplify signals emanating from the cell surface and resulting in some cellular effector function. One exemplar characterization of effector function as used herein may include responses resulting in cellular growth, differentiation, or the production (and sometimes release or transport out of the cell) of growth factors and/or other substances that have biological activity. For example, the following invention also provides for the stimulation of IL-2 production in a specified cell. This aspect of the invention can be achieved by modifying a specified cell to produce a chimeric protein having the ectodomain of the CEACAM1 receptor joined to a non-CEACAM1 adaptor portion capable of transducing signals effective in producing a response resulting in IL-2 production. One exemplar embodiment of the present invention provides chimeric constructs consisting of the extracellular portion of the human CEACAM1 protein fused to the transmembrane and cytosolic tail of the mouse zeta chain. Generation of BW cells (murine thymoma that lack ab chains of TCR, but have an intact mIL-2 secretion machinery) transfected with CEACAM1-mouse zeta construct resulted in the production of IL-2 upon addition of CEACAM1. The engagement of CEACAM1 in these cells activates the zeta chain. The BW cells are T cells, which respond to signals delivered by the zeta chain by secretion of mIL-2. The amount of mIL-2 detected in the medium correlates with CEACAM1 engagement.

CEACAM1 Based Cancer Therapy and Diagnosis

Certain aspects of the present invention relate to methods and compositions for the treatment and diagnosis of cancers expressing CEACAM1. At least one object of the present invention relates to methods and compositions for enhancing the efficacy of tumor-infiltrating lymphocyte (TIL) therapy in the treatment of cancer.

One object of the present invention is to provide methods and compositions for the regulation of the immune system and specific immune responses. Another object of the present invention is to provide methods and compositions for the regulation of lymphocyte activity. A still further object of the present invention is to provide methods and compositions for enhancing the efficacy of tumor-infiltrating lymphocyte (TIL) therapy in the treatment of cancer.

One or more of the preceding objects, or one or more other objects which will become plain upon consideration of the present specification, are satisfied by the invention described herein.

One aspect of the invention, which satisfies one or more of the above objects, is the functional modulation of at least one protein from the CEACAM protein family. Another aspect of the invention, which satisfies one or more of the above objects, is the negative functional modulation of the CEACAM1 (cd66a) protein.

Another aspect of the present invention provides methods for enhancing the efficacy of Tumor Infiltrating Lymphocyte cancer therapy that comprise the modulation of CEACAM1 protein function.

Another aspect of the present invention provides methods for enhancing the efficacy of Tumor Infiltrating Lymphocyte cancer therapy that comprises decreasing the effective concentration of CEACAM1 functional protein.

A still further aspect of the present invention provides methods for enhancing the efficacy of Tumor Infiltrating Lymphocyte cancer therapy comprising the enrichment of a Tumor Infiltrating Lymphocyte cell population for cells lacking CEACAM1.

Another aspect of the present invention provides methods for treating cancer in a human patient comprising the step of administering to the patient a therapeutically effective amount of a composition comprising a CEACAM1 binding agent conjugated to a chemotherapeutic.

A still further aspect of the present invention provides methods for diagnosing a cancer in a human patient, wherein the method comprises the step of contacting a biological sample, derived from a patient suspected of having cancer, with a CEACAM1 binding agent conjugated to a detectable moiety and/or an affinity moiety.

A still further aspect of the present invention provides methods for diagnosing a cancer in a human patient, wherein the method comprises the step of injecting into the patient a CEACAM1 binding agent conjugated to a detectable moiety.

The presently described technology relates to methods and compositions for the regulation of the immune system and specific immune responses, and in particular to methods and compositions for the regulation of lymphocyte activity. One object of the presently described technology provides methods and compositions for enhancing the efficacy of tumor-infiltrating lymphocyte (TIL) therapy in the treatment of cancer.

One aspect of the present invention is the functional modulation of at least one member of the CEACAM protein family. The CEACAM protein family, which are part of the larger Ig superfamily, include without limitation CEACAM 1, -3, -4, -5, -6, -7, and -8. The CEACAM protein family share a common basic structure of sequentially ordered different Ig-like domain(s) and are able to interact with each other.

In one embodiment of the presently described invention, regulation of the immune system and/or one or more specific immune responses is achieved by the negative modulation of CEACAM1 (cd66a) function. The negative modulation of CEACAM1 function can include the disruption of a CEACAM1 homotypic or heterotypic protein-protein interaction. The negative modulation of CEACAM1 function can include for example contacting CEACAM1 with a CEACAM1 specific binding element. The modulation of CEACAM1 function can also include for example contacting a protein interacting with the CEACAM1 protein with specific binding element or agent to inhibit or disrupt formation of a target CEACAM1 protein-protein interaction.

These elements or agents include but are not limited to linear or cyclic nucleic acids, full-length proteins, protein structural or functional domains, smaller peptides, and peptidomimetic derivatives. The terms "amino acid sequence," "nucleic acid sequence," "protein," "polypeptide," "peptide" and "nucleic acid" include compositions of the invention that also include "analogs," or "conservative variants" and "mimetics" such as "peptidomimetics" with structures and activity that substantially correspond to the compound from which the variant was derived. These agents can be derived from any protein that participates in any CEACAM family homotypic and/or heterotypic protein-protein interaction, or any other protein including but not limited to immunoglobins having binding specificity to a CEACAM family protein.

In certain embodiments of the present invention, the elements or agents employed to disrupt a CEACAM family protein-protein interaction to effect control over a particular immune response can include but are not limited to a full length CEACAM family protein, or a fragment derived therefrom. CEACAM family proteins that can be used as include but are not limited to the CEACAM1 protein represented by SEQ ID No. 1; the CEACAM3 protein represented by SEQ ID No. 2; the CEACAM5 protein represented by SEQ ID No. 3; the CEACAM6 protein represented by SEQ ID No. 4; and the CEACAM8 protein. In another embodiment of the present invention, the agent employed to disrupt a CEACAM family protein-protein interaction to effect control over a particular immune response can comprise any immunoglobulin, or fragment thereof, specific for the CEACAM family protein or protein interacting with the CEACAM family protein.

In still other embodiments of the present invention, the elements or agents employed to disrupt a CEACAM family protein-protein interaction to effect control over a particular immune response comprises a small molecule compound. The term "small molecule" means any synthetic small molecule, such as an organic molecule, inorganic molecule, or synthetic molecule, such as those generated by combinatorial chemistry methodologies. These small molecules can be synthesized using a variety of procedures and methodologies, which are well described in the scientific and patent literature, e.g., Organic Syntheses Collective Volumes, Gilman et al. (Eds) John Wiley & Sons, Inc., NY; Venuti (1989) *Pharm Res.* 6:867-873. Synthesis of small molecules, as with all other procedures associated with this invention, can be practiced in conjunction with any method or protocol known in the art. For example, preparation and screening of combinatorial chemical libraries are well known, see, e.g., U.S. Pat. Nos. 6,096, 496; 6,075,166; 6,054,047; 6,004,617; 5,985,356; 5,980,839; 5,917,185; 5,767,238.

In still other embodiments of the present invention, the elements or agents employed to disrupt a CEACAM family protein-protein interaction to effect control over a particular immune response comprises a multimer agent comprising at least two or more agents according to the present invention, linked together. The agents, linked together to form the multimer agent, can be identical or different, and can include but are not limited to any combination protein, nucleic acid, small molecules, or derivatives thereof.

In another embodiment of the presently described invention, regulation of the immune system and/or one or more specific immune responses includes the negative or positive modulation of CEACAM1 gene expression or translation of CEACAM1 mRNA. The modulation of CEACAM1 gene expression or CEACAM1 mRNA translation can involve contacting a population of cells with a protein, nucleic acid, small molecule, or any combination thereof. In another embodiment of the presently described invention, regulation of the immune system and/or one or more specific immune responses comprises the negative or positive modulation of CEACAM1 gene expression or translation of CEACAM1 mRNA. The modulation of CEACAM1 gene expression or CEACAM1 mRNA translation can comprise any number of techniques know to those skilled in the art for the modulation of gene expression, and can involve contacting any environment with a protein, peptide, peptidomimetic, nucleic acid, nucleic acid analog, small molecule, or some combination thereof.

In a further aspect of the presently described invention, there are provided methods and/or compositions for modulating the immune system and/or one or more specific immune responses in the course of treating a disease. Exemplar diseases include cancers, autoimmune conditions, and those diseases requiring tissue transplantation.

One aspect of the present invention provides methods and/or compositions for enhancing the efficacy of tumor-infiltrating lymphocyte (TIL) therapy in the treatment of cancer. In one embodiment of this aspect of the present invention, the efficacy of TIL therapy for the treatment of cancer is enhanced by the negative modulation of the functional activity of at least one member of the CEACAM protein family. In one preferred embodiment of this aspect of the present invention, the efficacy of TIL therapy for the treatment of cancer is enhanced by the negative modulation of CEACAM1 protein functional activity. The negative modulation of the at least one member from the CEACAM protein family, including but not limited to the CEACAM1 protein, can be accomplished by any number of techniques know to those skilled in the art for the negative modulation of protein function, including but not limited to the allosteric or non allosteric disruption of a homotypic or heterotypic protein-protein interaction.

Certain aspects of the present invention can be performed in situ, in vivo, or in vitro. For example, the methods and/or compositions of the present invention can be employed in a cell culture, including for example a population of Tumor Infiltrating Lymphocytes. The methods and/or compositions of the present invention may also be employed in the living body of an animal, such as a human.

In one preferred aspect of the present invention, the efficacy of TIL therapy for the treatment of cancer is enhanced by the negative modulation of CEACAM1 (cd66a) protein function in a population of tumor-infiltrating lymphocytes. In one embodiment of this aspect of the present invention, the efficacy of TIL therapy for the treatment of cancer is enhanced by the disruption of a homotypic and/or heterotypic CEACAM1 protein-protein interaction by contacting a population of tumor-infiltrating lymphocytes with CEACAM1 selective binding elements.

One object of the present invention includes methods and/or materials for controlling immunity and/or an immune response that involves the modulation of CEACAM1 function. The CEACAM1 protein may or may not be membrane bound. The modulation of CEACAM1 function can include, for example, the addition of a protein, peptide, peptidomimetic, nucleic acid, nucleic acid analog, small molecule, or any combination thereof. The CEACAM1 protein itself, in addition to any peptide or peptidomimetic derived from the CEACAM1 protein, or any immunoglobulin specific for CEACAM1, or any combination thereof, can be used to modulate CEACAM1 function. Also, a CEACAM1 binding partner can itself, in addition to any peptide or peptidomimetic derived from a CEACAM1 binding partner, or any immunoglobulin specific for a CEACAM1 binding partner, or any combination thereof, can be used to modulate CEACAM1 function.

Another aspect of the present invention provides methods for enhancing the efficacy of Tumor Infiltrating Lymphocyte cancer therapy that comprise the modulation of CEACAM1 protein function. The method of this aspect of the present invention can be performed in situ, in vivo, or in vitro. For example the method of this aspect of the present invention can be performed in a cell culture comprising a population of Tumor Infiltrating Lymphocytes. One embodiment of this aspect of the present invention comprises the disruption of a target CEACAM1 homotypic or heterotypic protein-protein interaction. The disruption of the target CEACAM1 homotypic or heterotypic protein-protein interaction comprises contacting at least one protein involved in the protein-protein interaction with an inhibitory agent that partially or completely inhibits or disrupts the protein-protein interaction. The inhibitory agent can comprise any an amino acid sequence, nucleic acid sequence, small molecule compound, or combinations thereof. The inhibitory agent can include but is not limited to any amino acid sequence derived from a CEACAM family protein sequence, including but not limited to sequences derived from the CEACAM1 protein. The inhibitory agent can also comprise an immunoglobulin or fragment thereof having specificity to at least one of the proteins involved in the CEACAM1 homotypic or heterotypic protein-protein interaction. The inhibitory agent that partially or completely inhibits or disrupts said protein-protein interaction can also be conjugated with a protein-crosslinking moiety.

Another aspect of the present invention provides methods for enhancing the efficacy of Tumor Infiltrating Lymphocyte cancer therapy that comprises decreasing the effective concentration of CEACAM1 functional protein. One embodiment of this aspect of the present invention comprises the inhibition of CEACAM1 gene expression, protein synthesis, protein stability, or combinations thereof. The method of this aspect of the present invention can be performed in situ, in vivo, or in vitro. For example the method of this aspect of the present invention can be performed in a cell culture comprising a population of Tumor Infiltrating Lymphocytes.

A still further aspect of the present invention provides methods for enhancing the efficacy of Tumor Infiltrating Lymphocyte cancer therapy comprising the enrichment of a Tumor Infiltrating Lymphocyte cell population for cells lacking CEACAM1. One embodiment of this aspect of the present invention comprises contacting the Tumor Infiltrating Lymphocyte cell population with a CEACAM1 binding element. The CEACAM1 binding element can include but is not limited to an anti-CEACAM1 immunoglobulin or fragment thereof. The CEACAM1 binding element can also include but is not limited to any amino acid sequence derived from a CEACAM family protein sequence, including but not limited to sequences derived from the CEACAM1 protein. The CEACAM1 binding element of this aspect of the present invention can be labeled with a detectable moiety, an affinity-tag moiety, or both. In certain embodiments of this aspect of the present invention the Tumor Infiltrating Lymphocyte cell population is subjected to affinity purification, cell sorting, or both. In still other embodiments of this aspect of the present invention the Tumor Infiltrating Lymphocyte cell population is contacted with an anti-CEACAM1 immunoglobulin and complement. In a still further embodiment of this aspect of the present invention the Tumor Infiltrating Lymphocyte cell population is contacted with a CEACAM1 binding element conjugated to a cell toxin.

Another aspect of the present invention provides methods for treating cancer in a human patient comprising the step of administering to the patient a therapeutically effective amount of a composition comprising a CEACAM1 binding agent conjugated to a chemotherapeutic. The CEACAM1 binding agent includes but is not limited to any amino acid sequence derived from a member of the CEACAM protein family, including but not limited to the CEACAM1 protein. The CEACAM1 binding agent can also comprise an anti-CEACAM1 immunoglobulin or fragment thereof. The CEACAM1 binding agent can also comprise a peptidomimetic or small molecule compound. The chemotherapeutic can include but is not limited to a cytotoxin, a chemokine, a pro-apoptotic, interferon, a radioactive moiety, or combinations thereof. In preferred embodiments of this aspect of the present invention, the chemotherapeutic moderates cellular metabolism. For example, the chemotherapeutic can moderate or alter nucleic acid metabolism, protein metabolism, cell division, DNA replication, purine biosynthesis, pyrimidine biosynthesis, amino acid biosynthesis, gene expression, mRNA processing, protein synthesis, apoptosis, or combinations thereof.

A still further aspect of the present invention provides methods for diagnosing a cancer in a human patient, wherein the method comprises the step of contacting a biological sample, derived from a patient suspected of having cancer, with a CEACAM1 binding agent conjugated to a detectable moiety and/or an affinity moiety. The CEACAM1 binding agent can comprise any amino acid sequence derived from a member of the CEACAM protein family, including but not limited to amino acid sequences derived from CEACAM1. The CEACAM1 binding agent can also comprise an anti-CEACAM1 immunoglobulin or fragment thereof. The CEACAM1 binding agent can also comprise a peptidomimetic or small molecule compound. The detectable moiety of this aspect of the present invention can comprise a fluorescent molecule, a radioactive molecule, or some combination thereof. The affinity moiety of this aspect of the present invention includes but is not limited to a magnetic particle.

A still further aspect of the present invention provides methods for diagnosing a cancer in a human patient, wherein the method comprises the step of injecting into the patient a CEACAM1 binding agent conjugated to a detectable moiety. The CEACAM1 binding agent can comprise any amino acid sequence derived from a member of the CEACAM protein family, including but not limited to amino acid sequences derived from CEACAM1. The CEACAM1 binding agent can also comprise an anti-CEACAM1 immunoglobulin or fragment thereof. The CEACAM1 binding agent can also comprise a peptidomimetic or small molecule compound. The detectable moiety of this aspect of the present invention can comprise a fluorescent molecule, a radioactive molecule, or some combination thereof. In certain other embodiments of this aspect of the present invention, the CEACAM1 binding agent conjugated to a detectable moiety is ingested by the human patient.

CEACAM1 Mediated Protective Immunity

The invention relates to the modulation of the immune system in general. More specifically, certain aspects of the present invention relate to the modulation of specific immune responses to create a protective immunity in the treatment of autoimmune diseases and diseases requiring the transplantation of tissue.

At least one object of the present invention is the modulation of CEACAM1 activity to effect control over the immune system and in particular specific immune responses in the treatment of disease. In particular, the present invention relates to the suppression of specific immune responses, by increasing the functional concentration of the CEACAM1 protein, to create a protective immunity in the treatment of certain disease states, including but not limited to autoimmune diseases and diseases requiring the transplantation of tissue.

Autoimmune disease results when the immune system mistakes self tissues for nonself and mounts an inappropriate attack. There are many different autoimmune diseases. Autoimmune disease can affect many parts of the body, including but not limited to nerves, muscles, the endocrine system (system that directs your body's hormones and other chemicals), and the digestive system. Some examples are Wegener's granulomatosis, multiple sclerosis, type 1 diabetes mellitus, rheumatoid arthritis, and Crohn's disease.

Transplant rejection occurs when the immune system of the recipient of a transplant attacks the transplanted organ or tissue. This is because a normal healthy human immune system can distinguish foreign tissues and attempts to destroy the transplant, just as it attempts to destroy infective organisms such as bacteria and viruses.

At present, regimens to treat both autoimmune diseases and tissue transplant rejection employ general immunosuppressant drugs. The present invention relates to the suppression of immune responses in a specific fashion, by increasing the functional concentration of the CEACAM1 protein in a target tissue to create a localized protective immunity for the treatment of autoimmune diseases and diseases requiring the transplantation of tissue.

One object of the present invention is to provide methods and compositions for the modulation of the immune system and/or one or more specific immune responses. Another object of the present invention is to provide methods and compositions for the regulation of lymphocyte activity. A further object of the present invention is to provide methods and/or compositions for inducing a tolerogenic state (immunologic tolerance or protective immunity) in a specified tissue, including but not limited to tissue affected by autoimmune disease or tissue being prepared for transplantation. A still further object of the present invention is to provide methods and compositions for the regulation of the immune system and specific immune responses in the treatment of disease, including but not limited to autoimmune diseases and diseases requiring organ transplantation.

One or more of the preceding objects, or one or more other objects which will become plain upon consideration of the present specification, are satisfied by the invention described herein.

One aspect of the present invention that satisfies one or more of the preceding objects provides methods for inducing a protective immunity in a target tissue. A further aspect of the present invention provides methods for the induction of CEACAM1 protein production in the tissue targeted for induction of a protective immunity. One embodiment of this aspect of the present invention comprises methods for the induction of CEACAM1 protein production in the tissue targeted for induction of a protective immunity.

One aspect of the present invention provides methods for inducing a protective immunity in a target tissue. One embodiment of this aspect of the present invention comprises methods for the induction of CEACAM1 protein production in the tissue targeted for induction of a protective immunity. The target tissue includes but is not limited to tissue afflicted by an autoimmune disease and/or tissue being prepared for transplantation. In preferred embodiments of this aspect of the present invention the induction of CEACAM1 protein production comprises the activation of CEACAM1 gene expression. activation of CEACAM1 gene expression can be accomplished any number of techniques known to those skilled in the art for the induction of gene expression, including but not limited to those techniques comprising contacting the target tissue with a signal transduction protein, transcriptional activator protein, nucleic acid, small molecule compound, or combination thereof. In preferred embodiments of this aspect of the present invention, the induction of CEACAM1 protein production comprises the transfer of a nucleic acid sequence into the cells of the target tissue encoding the CEACAM1 protein, or another protein that directly or indirectly increases CEACAM1 gene expression. The transfer of nucleic acid into a selected target tissue pursuant to this embodiment of the present invention can be accomplished by any number of techniques known to those skilled in the art including but not limited to viral-mediated transfer, particle-mediated transfer, or magnetic cationic liposome mediated transfer.

The presently described technology provides methods and compositions for the regulation of the immune system and specific immune responses, and in particular to methods and compositions for the regulation of lymphocyte activity. One aspect of the present invention is the functional modulation of at least one member of the CEACAM protein family, said CEACAM protein being either membrane bound or free. The CEACAM protein family, which are part of the larger Ig superfamily, include without limitation CEACAM 1, -3, -4, -5, -6, -7, and -8. The CEACAM protein family share a common basic structure of sequentially ordered different Ig-like domain(s) and are able to interact with each other.

In certain embodiments of the presently described invention, regulation of the immune system and/or one or more specific immune responses comprises the positive modulation of CEACAM1 gene expression or translation of CEACAM1 mRNA. The positive modulation of CEACAM1 gene expression or CEACAM1 mRNA translation can comprise any number of techniques know to those skilled in the art for the modulation of gene expression, and can involve contacting any cell or grouping of cells (e.g. tissue) with a protein, peptide, peptidomimetic, nucleic acid, nucleic acid analog, small molecule, or some combination thereof.

In a further aspect of the presently described invention, there are provided methods and/or compositions for modulating the immune system and/or one or more specific immune responses in the course of treating a disease. Exemplar diseases include but are not limited to autoimmune conditions, and those diseases requiring tissue transplantation.

Certain aspects of the present invention can be performed in any environment including but not limited to in situ, in vivo, or in vitro environments. For example, the methods and/or compositions of the present invention can be employed in a cell culture or in the living body of an animal, such as a human.

In a still further aspect of the presently described invention, methods and/or materials are provided for inducing a tolerogenic state (immunologic tolerance) in a specified tissue. As used herein, one exemplar definition for tissue includes any aggregate of cells. The specified tissue may include tissue affected by an autoimmune disease or tissue being prepared for transplantation. In one preferred embodiment thereof, the induction of the tolerogenic state includes the stimulation of CEACAM1 gene expression and protein production. This can be accomplished by any number of techniques know to those skilled in the art for the enhancement of gene expression and protein production.

At least one of the objects of the present invention is to induce a tolerogenic state in a specified tissue. This aspect of the present invention for example includes the induction of CEACAM1 protein production. The specified tissue may be tissue affected by an autoimmune disease or tissue being prepared for transplantation. The induction of CEACAM1 protein production includes, for example, the generation of CEACAM1 gene expression. In at least on aspect of the present invention, induction of CEACAM1 protein production includes the transfer of genetic material into the cells of the specified tissue for which a protective immunity is to be generated. The genetic material, for example, can be composed of a CEACAM1 family gene. Cis acting genetic elements may also be added to facilitate, for example, the integration of the genetic material into the genome of the specified cells, or the production of CEACAM1 protein, or both. The cis acting genetic elements may include genetic material effective in inducing efficient gene expression, efficient translation, increased recombination frequency, increased targeted recombination, or some combination thereof.

In an additional aspect of the invention, materials and/or methods are provided for inducing a protective immunity or tolorogenic state in a specified tissue, which includes the induction of CEACAM1 protein production by transferring genetic material that includes a gene whose protein product induces the increased production of a CEACAM1 family protein. For example, the gene whose protein product induces the increased production of a CEACAM1 family protein may be a transcription factor, including for example a transcriptional activator.

One aspect of the present invention provides methods and/or materials for imparting a tolerogenic state (i.e.—immunologic tolerance or protective immunity) upon a specified tissue. One embodiment of this aspect of the present invention provides methods and/or materials for imparting a tolerogenic state upon a specified tissue by imparting upon or inducing within a specified tissue CEACAM1 function. The specified tissue may be any tissue upon which it is desirable to create a tolerogenic state. For example, the tissue may be tissue that is being prepared for transplantation, or the tissue may be tissue which is afflicted by autoimmune disease. One definition of a tolerogenic state is a state characterized by an immunologic tolerance.

A further aspect of the present invention provides methods and/or materials for preparing tissue for grafting or transplantation. In one embodiment, the present invention provides materials and/or methods for mitigating the potential for immunological rejection of grafted or transplanted tissue. For example, the present invention provides for increased transplant tolerance strategies that would thwart the immunological rejection of transplanted or grafted tissue by imparting upon the transplanted tissue a tolerogenic state (immunologic tolerance), while preserving a body's general immune competence, including for example normal immune responses to pathogens and cancer risks. This aspect of the present invention may be accomplished, at least in part, by conveying or imparting CEACAM1 function or activity upon tissue to be transplanted or grafted. For example, tissue to be transplanted or grafted can be transformed or transfection of with genetic material effective in facilitating or inducing the production of CEACAM1 protein. This can be performed, for example, by the transfer of genetic material that is effective in inducing CEACAM1 protein production to tissue being prepared for transplantation or grafting. The genetic material that is transferred may include, for example, one or more functional CEACAM1 family genes, or some derivative thereof, including for example genetic material encoding specific CEACAM1 protein domains. The genetic material may also contain any cis acting genetic elements that may augment CEACAM1 protein production, including for example genetic elements that facilitate transcription (gene expression) and/or translation (protein synthesis). The transfer of genetic material may be accomplished by any method known in the art.

One exemplar aspect of transplantation includes an act, process, or instance of transplanting tissue; especially the removal of tissue from one part of the body or from one individual and its implantation or insertion in another especially by surgery. The transplantation of tissue can be allogeneic (allograft), which includes transplantation of tissue between genetically different members of the same species. For example, nearly all organ and bone marrow transplants are allografts. These may be between brothers and sisters, parents and children, or between donors and recipients who are riot related to each other. The transplantation can also be autologous (autograft), which includes transplantation of an organism's own tissues. A graft or transplantation of tissue from one site to another on the same individual is called an autograft. Autologous transplantation may be used to repair or replace damaged tissue. For example, autologous bone marrow transplantation permits the usage of more severe and toxic cancer therapies by replacing bone marrow damaged by the treatment with marrow that was removed and stored prior to treatment. The transplantation of tissue can also be syngeneic, which includes transplantation of tissue between genetically identical members of the same species (e.g., identical twins). The transplantation can also be xenogeneic (xenograft), which includes transplantation between members of different species; for example, the transplantation of animal tissues into humans.

One exemplar characterization of immunological rejection of transplanted tissue includes include those events by which a body's immune system attacks transplanted or grafted tissue, reacting to them as if they were harmful. Graft or transplant rejection generally involves the destruction of the grafted or transplanted tissue by attacking lymphocytes. In clinical transplantation, the types of transplant rejection may be classified into three main types: hyperacute, acute, and chronic.

The present invention also provides materials and/or methods for imparting a tolerogenic state upon engineered tissues. This aspect of the present invention can be achieved, at least in part, by imparting upon the engineered tissue CEACAM1 protein function. For example, one embodiment of the present invention involves the purification of a specific cell type of interest, followed by a transformation of the cell to produce CEACAM1 protein. These cells are then expanded in cell culture and seeded onto a scaffold of any desirable shape or rigidity prepared from a suitable biomaterial (or biocompatible material, or some combination) to form a scaffold/biological composite, or tissue engineered construct, that has decrease susceptibility to immunological rejection upon transplantation or grafting as replacement tissue.

A further aspect of the present invention provides methods and/or materials for imparting a tolerogenic state to tissue afflicted by autoimmune disease, while preserving a body's general immune competence, including for example normal immune responses to pathogens and cancer risks. This aspect of the present invention may be accomplished, at least in part, by conveying or imparting CEACAM1 function or activity upon tissue afflicted by autoimmune disease. For example, the present invention provides for the targeted transformation of tissue afflicted by autoimmune disease to express CEACAM1 protein. This can be accomplished, for example, by transfer of genetic information effective in inducing CEACAM1 protein production directly to tissue afflicted with an autoimmune disease, subsequent to any required exposure of the afflicted tissue. The genetic material that is transferred may include, for example, one or more functional CEACAM1 family genes, or some derivative thereof, including for example genetic material encoding specific CEACAM1 protein domains. The genetic material may also contain any cis acting genetic elements that may augment CEACAM1 protein production, including for example genetic elements that facilitate transcription (gene expression) and/or translation (protein synthesis). The transfer of genetic material may be accomplished by any method known in the art, and may be performed subsequent to exposure of the afflicted tissue by surgery, or if surgery is not an option, the effected tissue may be targeted utilizing receptor-mediated gene transfer technology.

Autoimmune diseases are generally characterized by the body's immune responses being directed against its own tissues, causing prolonged inflammation and subsequent tissue destruction. For example, autoimmune disorders can cause immune-responsive cells to attack the linings of the joints—resulting in rheumatoid arthritis—or trigger immune cells to attack the insulin-producing islet cells of the pancreas leading to insulin-dependent diabetes. A healthy immune system recognizes, identifies, remembers, attacks, and destroys bacteria, viruses, fungi, parasites, and cancer cells or any health-damaging agents not normally present in the body. A defective immune system, on the other hand, directs antibodies against its own tissues. Any disease in which cytotoxic cells are directed against self-antigens in the body's tissues is considered autoimmune in nature. Such diseases include, but are not limited to, celiac disease, Crohn's disease, pancreatitis, systemic lupus erythematosus, Sjogren's syndrome, Hashimoto's thyroiditis, and other endocrinopathies. Allergies and multiple sclerosis are also the result of disordered immune functioning.

Examples of different types of viruses used as vectors for the transfer of genetic material include, without limitation: retroviruses; adenoviruses; adeno-associated viruses; and herpes simplex viruses. Besides virus-mediated genetic material delivery systems, there are several nonviral options for delivery. The simplest method is the direct introduction of the genetic material into target cells. Another nonviral approach involves the creation of an artificial lipid sphere with an aqueous core. This liposome, which carries the genetic material, is capable of passing the genetic material through the target cell's membrane. Genetic material can also get inside target cells by chemically linking the genetic material to a molecule that will bind to special cell receptors. Once bound to these receptors, the genetic material constructs are engulfed by the cell membrane and passed into the interior of the target cell.

Particle mediated transfer of genetic material is also a viable method to introduce genetic material according to some aspects of the present invention. Any method regarding the particle mediated transfer of genetic material known in the art may be used. For example, the gene gun is part of a method sometimes called the biolistic (also known as bioballistic) method. Under certain conditions, DNA (or RNA) becomes "sticky," adhering to biologically inert particles such as metal atoms (usually tungsten or gold). By accelerating this DNA-particle complex in a partial vacuum and placing the target tissue within the acceleration path, DNA is effectively introduced (Gan, Carol. "Gene Gun Accelerates DNA-Coated Particles To Transform Intact Cells". *The Scientist*; Sep. 18, 1989, 3[18]:25. This reference is herein incorporated by reference). Uncoated metal particles could also be shot through a solution containing DNA surrounding the cell thus picking up the genetic material and proceeding into the living cell. A perforated plate stops the shell cartridge but allows the slivers of metal to pass through and into the living cells on the other side. The cells that take up the desired DNA, identified through the use of a marker gene (in plants the use of GUS is most common), are then cultured to replicate the gene and possibly cloned. The biolistic method is most useful for inserting genes into plant cells such as pesticide or herbicide resistance. Different methods have been used to accelerate the particles: these include for example pneumatic devices; instruments utilizing a mechanical impulse or macroprojectile; centripetal, magnetic or electrostatic forces; spray or vaccination guns; and apparatus based on acceleration by shock wave, such as electric discharge.

The following invention also provides for the control and/or modulation of a cellular signal transduction pathway(s) designed to transduce and amplify signals emanating from the cell surface and resulting in some cellular effector function. One exemplar characterization of effector function as used herein may include responses resulting in cellular growth, differentiation, or the production (and sometimes release or transport out of the cell) of growth factors and/or other substances that have biological activity. For example, the following invention also provides for the stimulation of IL-2 production in a specified cell. This aspect of the invention can be achieved by modifying a specified cell to produce a chimeric protein having the ectodomain of the CEACAM1 receptor joined to a non-CEACAM1 adaptor portion capable of transducing signals effective in producing a response resulting in IL-2 production. One exemplar embodiment of the present invention provides chimeric constructs consisting of the extracellular portion of the human CEACAM1 protein fused to the transmembrane and cytosolic tail of the mouse zeta chain. Generation of BW cells (murine thymoma that lack ab chains of TCR, but have an intact mIL-2 secretion machinery) transfected with CEACAM1-mouse zeta construct resulted in the production of IL-2 upon addition of CEACAM1. The engagement of CEACAM1 in these cells activates the zeta chain. The BW cells are T cells, which respond to signals delivered by the zeta chain by secretion of mIL-2. The amount of mIL-2 detected in the medium correlates with CEACAM1 engagement.

Example 1

Residues 43R and 44Q of Carcinoembryonic Antigen Cell Adhesion Molecules-1 (CEACAM1) are Critical in the Protection from Killing by Human NK Cells The present inventors have shown that the CEACAM1 (CD66a) homophilic interactions inhibit the killing activity of NK cells. This novel inhibitory mechanism plays a key role in melanoma immune evasion, inhibition of decidual immune response, and controlling NK autoreactivity in TAP2-deficient patients. These roles are mediated mainly by homophilic interactions, which are mediated through the N-domain of the CEACAM1. The N-domain of the various members of the CEACAM family shares a high degree of similarity. The present inventors have addressed which of the CEACAM family members are able to interact with CEACAM1 and what amino acid residues control this interaction. In this section it is shown that CEACAM1 interacts with CEACAM5, but not with CEACAM6. The present inventors have demonstrated the inability of CEACAM1 to bind CEACAM6. Importantly, the present inventors provide the molecular basis for CEACAM1 recognition of various CEACAM family members. Sequence alignment reveals a dichotomy among the CEACAM family members: both CEACAM1 and CEACAM5 contain the R and Q residues in positions 43 and 44, respectively, whereas CEACAM3 and CEACAM6 contain the S and L residues, respectively. Mutational analysis revealed that both 43R and 44Q residues are necessary for CEACAM1 interactions. The inventors have considered the implications for differential expression of CEACAM family members in tumors.

The inventors in this section directly show that the presence of both residues 43R and 44Q in the CEACAM1 is crucial for the homophilic CEACAM1 interaction and that substitution of these residues with the 43S and 44L, residues that are present in CEACAM6 abolishes the inhibitory effect. Importantly, the reciprocal substitution of 43S and 44L of CEACAM6 to the 43R and 44Q residues, respectively, results in the gain of inhibitory heterophilic interactions with the CEACAM1 protein. The dichotomy of CEACAM family members by recognition of CEACAM1 is determined by the presence of R and Q at positions 43 and 44. (Gal Markel et al., *The Critical Role of Residues 43R and 44Q of Carcinoembryonic Antigen Cell Adhesion Molecules-1 in the Protection from Killing by Human NK Cells, The Journal of Immunology,* 2004, 173: 3732-3739. This reference is herein incorporated by reference.)

Materials and Methods

Cells

The cell lines used were the MHC class I-negative 721.221 human cell line, the murine thymoma BW cell line that lacks expression of _- and _-chains of the TCR, and the NK tumor line YTS. Primary NK cells were isolated from PBL using the human NK isolation kit and the autoMACS instrument (Miltenyi Biotec, Auburn, Calif.). For the enrichment of CEACAM1-positive NK cells, isolated NK cells were further purified by depletion of CD16-positive NK cells, using the anti-CD16 mAb B73.1.1 and the auto MACS instrument. NK cells were grown in culture as previously described (16). CEACAM1-positive NK clones were identified by flow cytometry using the anti-CEACAM1 mAb 5F4 and were tested for inhibition in killing assays against 0.221/CEACAM1 cells.

Antibodies

The Abs used in this work were mAb Kat4c (DakoCytomation, Carpenteria, Calif.), directed against CEACAM1, -5, -6, and -8; the anti-CD99 mAb12E7; the rabbit polyclonal anti-CEACAM (DakoCytomation); and the specific anti-CEACAM1 mAb 5F4 (10). Rabbit polyclonal Abs against purified ubiquitin were used as the control.

Generation of CEACAM1-Ig Fusion Protein

The extracellular portion of the CEACAM1 protein was amplified by PCR using the following primers: the 5' primer CCCAAGCTTGGGGCCGC CACCATGGGGCACCTCT-CAGCC (including the HindIII restriction site) (SEQ ID NO 5) and the 3' primer GCGGATCCCCAGGTGAGAGGC (including the BamHI restriction site) (SEQ ID NO 30). A silent mutation, adenine885guanidine (no change in glycine281) was performed by site-directed mutagenesis to cancel the BamHI site in the amplified sequence. The production of the CEACAM1-Ig and CD99-Ig fusion proteins by COS-7 cells and purification on a protein G column were previously described (8, 17). The fusion proteins were periodically analyzed for degradation by SDS-PAGE.

Generation of Transfectants

The 721.221 cells expressing CEACAM1 and CEACAM6 proteins were generated as previously described (7). The CEACAM5 cDNA was subcloned into pcDNA3 vector. This construct was permanently transfected to 721.221 cells. For the generation of 721.221 cells expressing the CEACAM6 protein fused to the tail of CEACAM1, the extracellular portion of the CEACAM6 was first amplified without the GPI-anchoring sequence using the 5' primer CCCAAGCTTGC-CGCCACCATGGGAC CCCCCTCAGCC (including the HindIll restriction site) (SEQ ID NO 6) and the 3' primer AATGGCCCCTCCAGAGACTGTGATCATCGT (including the first nine nucleotides of the CEACAM1 transmembrane portion) (SEQ ID NO 7). The transmembrane and tail of the CEACAM1 protein were amplified with the 5' primer GTCTCTGGAGGGGCCATTGCTGGCATTG (including the last nine nucleotides of the CEACAM6 extracellular portion before the GPI anchor motif) (SEQ ID NO 8) and the 3' primer GGAATTCCTTACTGCTTTTTTACTTCTGAATA (including the EcoRI restriction site) (SEQ ID NO 9). Amplified fragments were mixed and fused by an additional PCR that was performed with the 5'-HindIII primer and the 3'-EcoRI primer. The construct was cloned into pcDNA3 vector (Invitrogen Life Technologies, Carlsbad, Calif.) and permanently transfected to 721.221 cells. For the generation of BW cells expressing the chimeric CEACAM1-_protein, the same technique was used. The extracellular portion of the human CEACAM1 protein was amplified by PCR using the 5' primer CCCAAGCTTGGGGCCGCCAC-CATGGGGCACCTCTCAGCC (including HindIII restriction site) (SEQ ID NO 10) and the 3' primer GTAGCA-GAGAG GTGAGAGGCCATTTTCTTG (including the first nine nucleotides of the mouse _-chain transmembrane portion) (SEQ ID NO 11). The mouse _-chain was amplified by PCR using the 5' primer CTCTCACCTCTCTGCTACT TGCTAGATGGA (including last nine nucleotides of human CEACAM1 extracellular portion) (SEQ ID NO 12) and the 3' primer GGAATTCCTTA GCGAGGGGCCAGGGTCTG (including EcoRI restriction site) (SEQ ID NO 13). The two amplified fragments were mixed, and PCR was performed with the 5' HindIII primer and the 3' EcoRI primer for generation of the CEACAM1-_ construct. The CEACAMI-_ construct was cloned into pcDNA3 expression vector (Invitrogen Life Technologies) and was stably transfected into BW cells. All transfectants were periodically monitored for expression by staining with the appropriate mAb.

Generation of 721.221 Cells Expressing Mutated CEACAM1 or CEACAM6 Proteins

For generation of the mutated CEACAM proteins, two overlapping fragments of the gene were amplified by PCR. The upstream fragment was amplified by using a gene-specific 5'-edge primer (including the HindIII restriction site) and an internal 3' primer bearing the mutation. The downstream fragment was amplified using an internal 5' primer bearing the mutation and a gene-specific 3'-edge primer (including EcoRl restriction site). Next, both purified fragments were mixed together with the 5'-edge primer and the 3'-edge primer to generate the mutated full-gene cDNA. All different mutants of the same CEACAM gene were generated using the same appropriate edge primers and different internal primers. The various cDNAs were then cloned into the pcDNA3 mammalian expression vector and stably transfected into the 0.221 cell line. All transfectants were periodically monitored for expression by staining with the appropriate mAb. For CEACAM1-RQ43,44SL, the 5_-CEACAM1 edge primer was CCCAAGCTTGGGGCCGCCAC-CATGGGGCACCTCTCAGCC (SEQ ID NO 5), the 3'-CEACAM1 edge primer was GGAATTCCTTACT-GCTTTTTTACT TCTGAATA (SEQ ID NO 9), the 5' internal primer was GCCAACAGTCTAATTGTA GGA (SEQ ID NO 14), and the 3' internal primer was TCCTACAATTA-GACTGTTGCC (SEQ ID NO 15). For CEACAM1-R43A, the 5' internal primer was GATGGCAACGCTCAAAT TGTA SEQ ID NO 16), and the 3' internal primer was TACAATTTGAGCGTTGCCATC (SEQ ID NO M. For CEACAM1-Q44L, the 5' internal primer was ATGGCAAC-CGTCTA ATTGTAG (SEQ ID NO 18), and the 3' internal primer was CTACAATTAGACGGTTGC CAT (SEQ ID NO 19). For CEACAM6-SL43,44RQ, the 5'-CEACAM6 edge primer was CCCAAGCTTGCCGCCACCATGGGAC-CCCCCTCAGCC (SEQ ID NO 6), the 3'-CEACAM6 edge primer was GGAATTCCCTATATCAGAGCCACCCTGG (SEQ ID NO 20), the 5' internal primer was GGCAACCGT-CAAATTGTAGGA (SEQ ID NO 21), and the 3' internal primer was TCCTACAATTTGACGGTTGCC (SEQ ID NO 22). For CEACAM6-S43R, the 5' internal primer was GATG-GCAACCGTCTAAT TGTA (SEQ ID NO 23), and the 3' internal primer was TACAATTAGACGGTTGCCATC (SEQ ID NO 24). For CEACAM6-L44Q, the 5' internal primer was GATGGCAACAGTCAAATTGTA (SEQ ID NO 25), and the 3' internal primer was TACAATTTGACTGTTGCCATC (SEQ ID NO 26).

Cytotoxicity Assays

The cytotoxic activity of YTS and NK cells against various targets was assayed in 5-h [35S]Met release assays, as described previously (16). In experiments in which rabbit polyclonal Abs were included, the final concentration was 20 _g/ml. In all cytotoxicity assays performed, spontaneous release did not exceed 20% of maximal labeling.

Cross-Linking of BW/CEACAM1 Cells

BW/CEACAM1 cells (0.5_105/well) were incubated with various amounts of Kat4c mAb on ice for 1 h in 96-well, round-bottom microplates (Nalge Nunc, Rochester, N.Y.). Treated BW/CEACAM1-_ cells, present in 200 _l of RPMI 1640 complete medium, were then cultured in 96-well, flat-bottom microplates (Nalge Nunc) precoated with 1 _g/well sheep anti-mouse IgG Abs (ICN Biomedicals, Costa Mesa, Calif.) for 24 h at 37° C. Supernatant was harvested, and the amount of murine IL-2 (mIL-2) was determined by ELISA.

CEACAM1 Protein does not Recognize CEACAM6

The surface expression of the CEACAM1 protein on tumors is associated with poor prognosis in melanoma and lung adenocarcinoma patients. Moreover, the CEACAM1 homophilic interactions confer protection from human NK-mediated cytotoxicity, and in some melanoma patients bearing CEACAM1-positive tumors, a dramatic increase in the proportion of CEACAM1-positive NK cells was observed. Because heterophilic interactions of the CEACAM1 protein with the CEACAM6 protein were reported previously (12), and because some CEACAM1-positive tumors down-regulate the CEACAM1 protein expression and instead replace it with CEACAM6 (14, 15), it was investigated whether CEACAM1 can interact with CEACAM6.

721.221 (0.221) cells were transfected with the CEACAM1 cDNA (0.221/CEACAM1) and with the CEACAM6 cDNA (0.221/CEACAM6) as described in Materials and Methods. The expression level was monitored with the Kat4c mAb (FIG. 1). For measuring direct binding of CEACAM1 to the transfected cells, the extracellular portion of the CEACAM1 fused to the Fc portion of human IgG1 (CEACAM1-Ig) was used in flow cytometry binding assays. The production and purification of the CEACAM1-Ig fusion protein were performed as described in Materials and Methods. Homophilic binding of the CEACAM1-Ig fusion protein was observed only in the 0.221/CEACAM1 cells (FIG. 1). In contrast, despite a slightly higher expression level of the CEACAM6 protein (detected by Kat4c mAb, FIG. 1), CEACAM1-Ig did not bind to 0.221/CEACAM6 cells (FIG. 1). The control CD99-Ig fusion protein did not stain any of the transfectants.

The potential heterophilic interactions between the CEACAM1 and CEACAM6 proteins were further investigated using the BW cell system. BW cells were stably transfected with the extracellular portion of the CEACAM1 fused to mouse _-chain (BW/CEACAM1-_) as described in Materials and Methods. The specific functionality of BW/CEACAM1-_ was assessed by crosslinking the CEACAM1 receptor using different amounts of immobilized Kat4c mAb as described in Materials and Methods. Engagement of the CEACAM1 protein elicited the synthesis and secretion of mIL-2 in a dose dependent manner (FIG. 2A). Treatment with the control anti-CD99 12E7 gave no response (FIG. 2A). Next, BW parental cells and BW/CEACAM1-_ were co cultured with irradiated 0.221, 0.221/CEACAM1, or 0.221/CEACAM6 cells for 48 h. Significant amounts of mIL-2 were detected in the supernatant of BW/CEACAM1-_ cells co incubated with 0.221/CEACAM1 cells (FIG. 2B). In contrast, no mIL-2 was detected when BW/CEACAM1-_ cells were co incubated with 0.221 or 0.221/CEACAM6 cells (FIG. 2B). No secretion of mIL-2 was observed when parental BW cells were used (FIG. 2B). These combined results suggest that the CEACAM1 and CEACAM6 proteins do not bind or functionally interact.

GPI Anchorage of CEACAM6 is not Responsible for the Lack of Heterophilic Interactions with the CEACAM1

Figure 3:
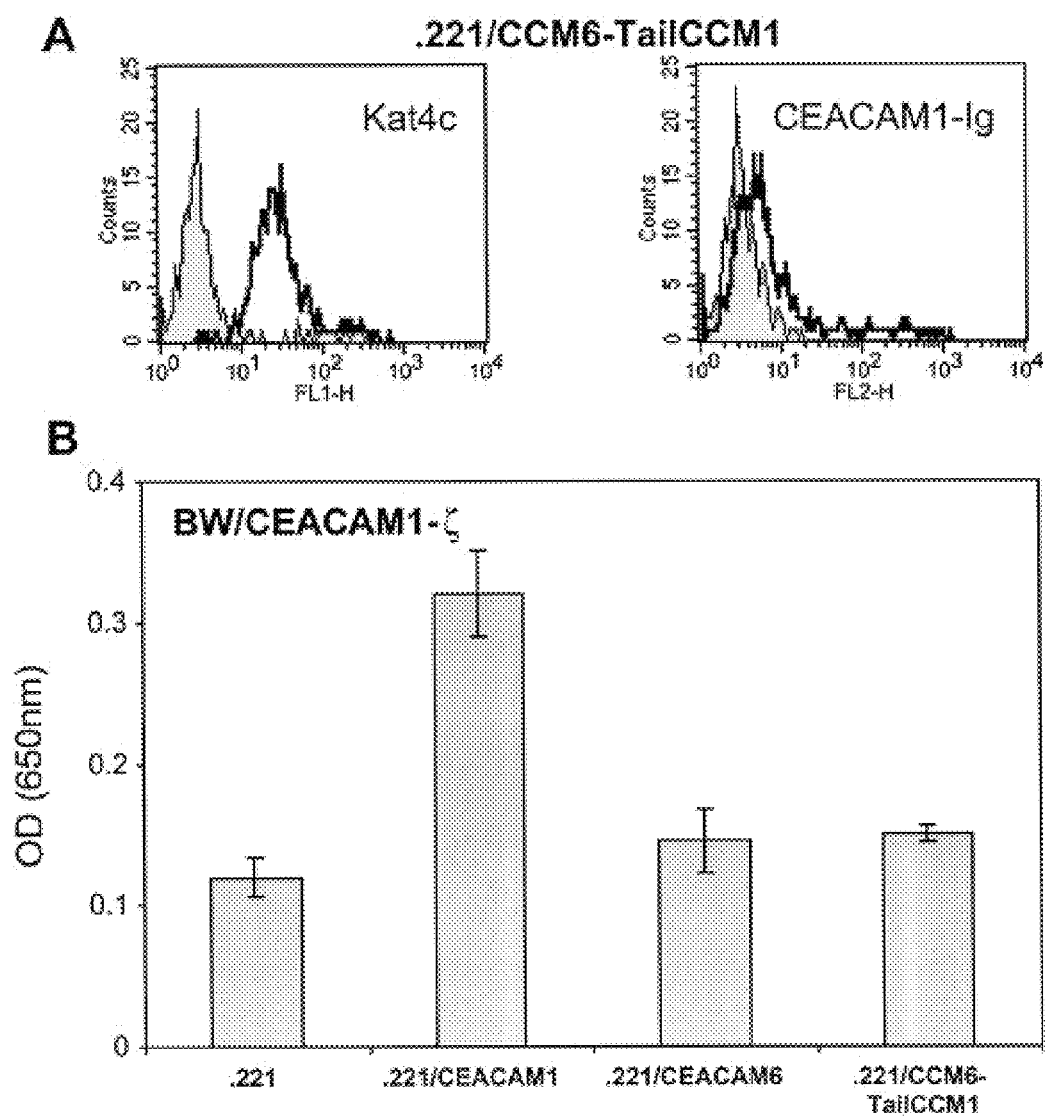
FIG. 3. Substitution of the GPI link of CEACAM6 with the transmembrane and tail of CEACAM1 does not induce heterophilic binding. A, Staining of 0.221/CCM6-TailCCM1 cells with Kat4c (empty histogram) mAb or CEACAM1-Ig (empty histogram). The reagents used are indicated in each histogram. The background is the staining of 0.221 parental cells (shaded histogram). This figure shows one representative experiment of 10 performed. B, mIL-2 secretion by BW/CEACAM1-_ cells co incubated for 48 h with irradiated 0.221 or with 0.221 transfectants. The y-axis indicates the optic density at a wavelength of 650 nm. The average of four independent experiments is shown.

Several explanations may account for the potential lack of heterophilic interactions between CEACAM1 and CEACAM6 proteins. CEACAM1 is a transmembrane protein, whereas CEACAM6 is GPI-anchored to the cell membrane. It is possible that the GPI anchor of CEACAM6 and the absence of transmembrane and cytosolic portions weaken the interaction. Furthermore, it is possible that other transmembrane elements play a key role in the interactions. For example, a cysteine residue located in the transmembrane domain of HLA-C was reported to be crucial for the inhibition mediated by an unknown inhibitory NK receptor. To test whether the GPI anchor of CEACAM6 protein is responsible for the lack of CEACAM1 binding, a chimeric construct comprised of the entire extracellular portion of CEACAM6 fused to the transmembrane and tail portions of CEACAM1 (CCM6-TailCCM1) was generated. The 0.221 cells were stably transfected with the CCM6-TailCCM1 construct (0.221/CCM6-TailCCM1). The expression level of the CCM6-TailCCM1 chimeric protein, detected by Kat4c mAb, was similar to that of the other 0.221/CEACAM stable transfectants (FIGS. 1 and 3A). Importantly, no binding of CEACAM1-Ig was observed to 0.221/CCM6-TailCCM1 cells (FIG. 3A). In agreement with the binding results, the presence of mIL-2 was not detected in the supernatant of BW/CEACAM1 cells co incubated with 0.221/CCM6-TailCCM1 cells (FIG. 3B). These results suggest that the lack of heterophilic interactions of CEACAM1 and CEACAM6 may not be due to the transmembrane and cytosolic tail portions of the proteins.

Residues 43R and 44Q are Critical for CEACAM1 Binding

CEACAM-related proteins share a common basic structure of several sequential Ig-like domains. The Ig-like domains serve as fundamental building blocks of the various CEACAM-related proteins, and they differ only slightly from one protein to another. Importantly, the binding site of the CEACAM1 is located in the N-domain (13). Sequence alignment of the N-domains of CEACAM-related proteins, including CEACAM1, CEACAM3, CEACAM5, and CEACAM6, revealed exceptional homology (FIG. 4). Within the CEACAM1 N-domain, several amino acid residues may be crucial for binding. These include amino acids 39V and 40D (13) and the salt bridge between 64R and 82D (13). All of the above-reported amino acid residues are present in the N-domain of CEACAM6 (FIG. 4), implying that they may not account for the lack of heterophilic interactions with the CEACAM1 protein.

Three short sequences located in the N-domain of CEACAM5 are critical for CEACAM5 homophilic interactions (Taheri et al. (20)). These short sequences include 30GYSWYK, 42NRQII, and 80QNDTG. Importantly, these three short sequences are present in the N-domain of the CEACAM1 protein. However, only the 30GYSWYK and 80QNDTG short sequences are preserved in the N-domain of the CEACAM6 protein, whereas the 43R44Q residues are replaced with 43S44L residues within the 42NRQII sequence (FIG. 4). A mutated construct was generated of the CEACAM6 gene that includes amino acids R and Q at positions 43 and 44 instead of S and L, respectively (CCM6-SL43,44RQ). In addition, the reciprocal mutation in CEACAM1 was generated that includes amino acids S and L at positions 43 and 44 instead of R and Q, respectively (CCM1-RQ43,44SL). The 0.221 cells were stably transfected with the various constructs and tested for expression using Kat4c mAb (FIG. 5A). The expression levels of the mutated proteins were similar to those of CEACAM1 and CEACAM6 (FIGS. 1 and 5A).

Next, 0.221/CCM6-SL43,44RQ and 0.221/CCM1-RQ43, 44SL were tested in flow cytometry binding assays using CEACAM1-Ig. Remarkably, substitution of 43R44Q with 43S44L in 0.221/CCM1-RQ43,44SL abolished homophilic binding (FIG. 5A). This abolishment was probably not merely due to a steric disturbance of the CEACAM1 N-domain structure, because the reciprocal mutation, 43S44L with 43R44Q in 0.221/CCM6-SL43,44RQ, conferred strong binding of the CEACAM1-Ig fusion protein (FIG. 5A). The CD99-Ig fusion protein did not stain any of the transfectants. Strikingly, recognition of the mutated CEACAM1 protein by the conformation-dependent anti-CEACAM1 mAb 5F4 (10, 13), was abolished, whereas specific staining of 0.221/CCM6-SL,43,44RQ was observed (FIG. 5B). These results imply that the 43R and 44Q residues are critically involved in conferring the appropriate conformation required for recognition by CEACAM1.

The binding results were also confirmed by functional assays using the BW cell system. Significant amounts of mIL-2 were detected only in supernatants of BW/CEACAM1-_ cells co incubated with irradiated 0.221/CCM6-SL43,44RQ or 0.221/CEACAM1 cells (FIG. 5C). The stronger mIL-2 induction after incubation of BW/CEACAM1-_ cells with the 0.221/CCM6-SL43,44RQ cells compared with 0.221/CEACAM1 cells might be due to the higher protein expression measured by Kat4c mAb (FIGS. 1 and 5A). The presence of mIL-2 could not be detected in the supernatants of BW/CEACAM1-_ cells co incubated with irradiated 0.221/CEACAM6 cell or 0.221/CEACAM1 RQ43,44SL (FIG. 5C). Mouse IL-2 was not detected when BW parental cells were used. These results show that residues 43R44Q are critical for the functional CEACAM1 interactions.

Residues 43R and 44Q are Critical for CEACAM1-Mediated Inhibition of NK Cell Cytotoxicity CEACAM1 plays a major role in regulation of NK cell cytotoxicity (7), inhibition of decidual immune responses after activation (8), and conferring protection from NK autoreactivity in TAP2-deficient patients (9). To test whether residues 43R44Q would also be important in the inhibition of NK killing, NK cells from several healthy donors were isolated, depleted the CD16-positive NK cells, activated NK clones were then cultured as described in Materials and Methods, and stained for CEACAM1 expression.

Figure 5:
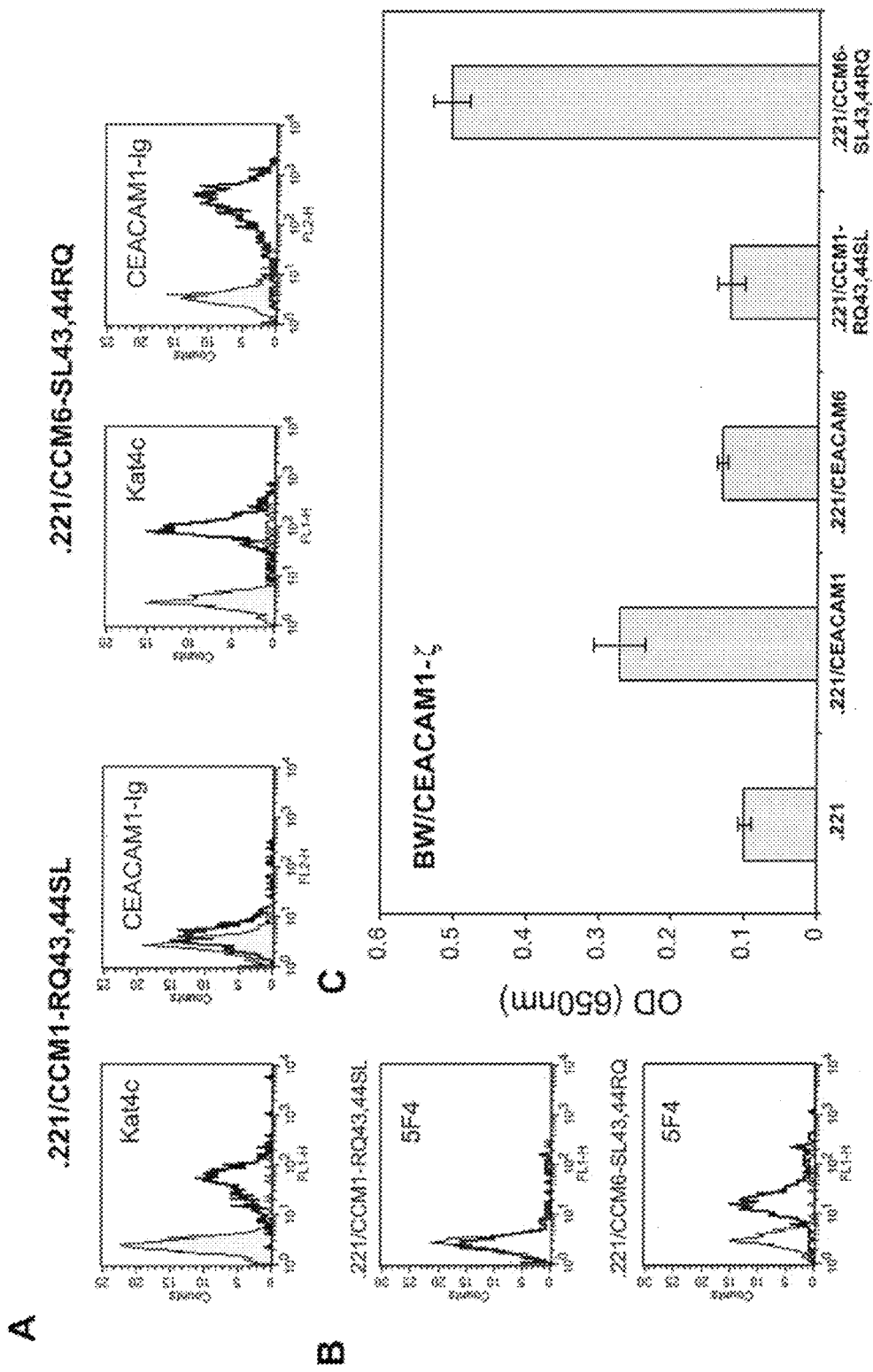
FIG. 5. Recognition of CEACAM1 is dependent on the presence of 43R44Q. A, Staining of 0.221/CCM1-RQ43, 44SL or 0.221/CCM6-SL43,44RQ cells with Kat4c mAb or CEACAM1-Ig fusion protein as indicated in each histogram. The corresponding staining of 0.221 parental cells was used as background (shaded histograms). This figure shows one representative experiment of six performed. B, Staining of 0.221/CCM1-RQ43,44SL, or 0.221/CCM6-SL43,44RQ cells with the conformation-dependent 5F4 mAb (thick lines). The corresponding staining of 0.221 parental cells was used as background (thin lines). This figure shows one representative experiment of six performed. C, mIL-2 secretion by BW/CEACAM1-_ cells co incubated for 48 h with irradiated 0.221 or 0.221 transfectants. The y-axis indicates the optic density at a wavelength of 650 nm. The average of five independent experiments is shown.
Figure 6:
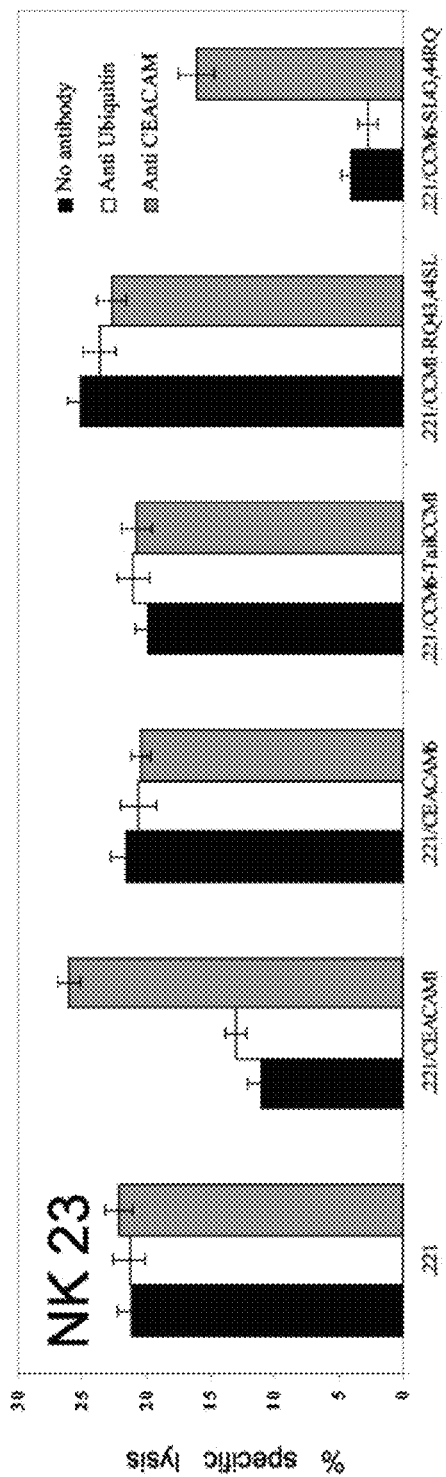
FIG. 6. NK-mediated cytotoxicity. CEACAM1-positive NK clones were obtained as described in Materials and Methods. NK clones were tested in killing assays against the indicated cells in an E:T cell ratio of 2:1. When rabbit polyclonal Abs were included in the assays, the final concentration was 20 _g/ml. This figure shows the results of a representative NK clone.

CEACAM1-positive NK clones were assayed for cytotoxic activity against 0.221 parental cells and various stable transfectants, including 221/CEACAM1, 0.221/CEACAM6, 0.221/CCM6-Tail-CCM1, 0.221/CCM1-RQ43,44SL, and 0.221/CCM6-SL43,44RQ cells. NK cytotoxicity assays were performed with no Ab included, in the presence of anti CEACAM polyclonal Abs, or with the control anti-ubiquitin polyclonal Abs. All NK clones efficiently killed parental 0.221 cells regardless of whether Abs were included (representative clone NK23 is presented in FIG. 6). As previously reported (7-9), inhibition of NK killing was observed when 0.221/CEACAM1 cells were used. This inhibition was the result of CEACAM1 inhibition, because anti-CEACAM Abs abrogated this effect (FIG. 6). The lack of heterophilic interactions between CEACAM1 and CEACAM6 was evident in the NK killing assays, because 0.221/CEACAM6 and 0.221/CCM6-TailCCM1 cells were killed as efficiently as parental 0.221 cells (FIG. 6). In agreement with the above results (FIG. 5), no inhibition was observed when 0.221/CCM1 RQ43,44SL cells were used (FIG. 6). Remarkably, a strong inhibition of killing was observed when CCM6-SL43,44RQ cells were used as targets (FIG. 6). The inhibition was even stronger than that observed with the homophilic CEACAM1 interactions, probably due to the higher CCM6-SL43,44RQ expression. This inhibition was the result of heterophilic interactions with CEACAM1 protein on NK cells, because killing was restored when anti-CEACAM Abs were included in the assay (FIG. 6). The control anti-ubiquitin had little or no effect when included in the assays (FIG. 6).

Figure 7:
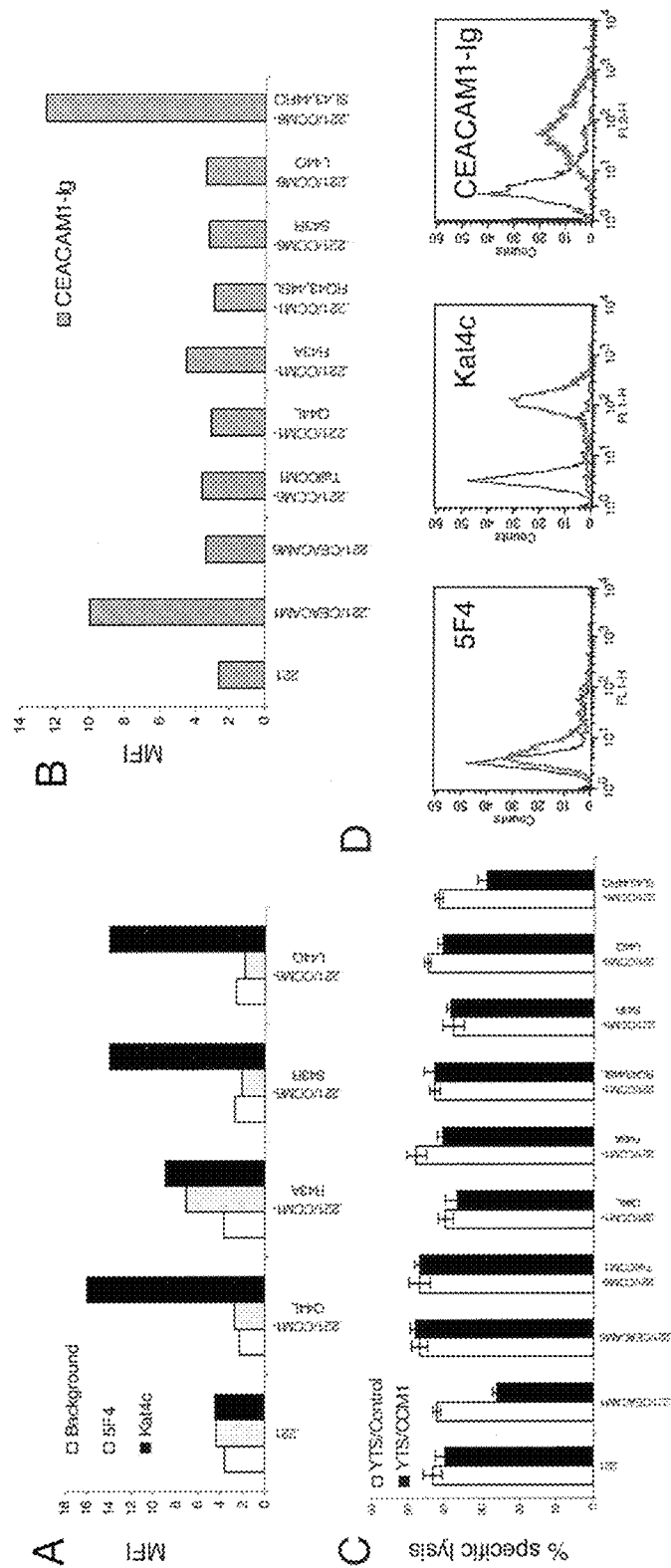
FIG. 7. Both the 43 and 44 residues of CEACAM1 are crucial for the interaction. A, Staining of 0.221 and various 0.221 stable transfectants with 5F4 mAb (u) or with Kat4c (f). The staining of the secondary reagent FITC-conjugated goat anti-mouse F(ab')2 of each cell type was used as background (squares). The y-axis indicates the median fluorescence intensity (MFI). This figure shows one representative experiment of four performed. B, Staining of 0.221 and various 0.221 stable transfectants with CEACAM1-Ig fusion protein. The y-axis indicates the median fluorescence intensity (MFI). This figure shows one representative experiment of four performed. C, YTS cells expressing the CEACAM1 protein (YTS/CCM1) or mock-transfected (YTS/control) were tested in killing assays against 0.221 and 0.221 transfectants. The E:T cell ratio was 2:1. This figure shows the average of three independent experiments. D, Staining of 0.221/CEACAM5 cells with 5F4, Kat4c, or CEACAM1-Ig was performed as indicated in each histogram. The corresponding staining of 0.221 parental cells was used as background (thin lines). This figure shows one representative experiment of six performed.

Specificity of CEACAM1 Binding to CEACAM6 is Controlled by the Presence of Both 43R and 44Q Residues To determine whether both residues are required for binding, the amino acid residues in positions 43 and 44 in CEACAM1 (contains 43R44Q) and CEACAM6 (contains 43S44L) were mutated. Using site-directed mutagenesis in the CEACAM1, the 43R residue was changed to 43A (CCM1-R43A) and the 44Q residue was changed to 44L (CCM1-Q44L). In CEACAM6, the 43S was changed to 43R (CCM6-S43R) and 44L was changed to 44Q (CCM6-L,44Q). All mutants were generated as described in Materials and Methods and stably transfected into 0.221 cells. The expression level was monitored by Kat4c mAb, and conformation was monitored by 5F4 mAb (FIG. 7A). Importantly, substitution for 44Q in CEACAM1 protein by 44L in 0.221/CCM1-Q44L completely abrogated 5F4 binding, whereas the Kat4c binding observed was similar to that of wild type CEACAM1 (FIG. 7A). This suggests that the 44Q residue is essential for maintaining appropriate conformation, which is crucial for binding of 5F4 mAb. Indeed, this mutation also resulted in a lack of recognition by the CEACAM1-Ig (FIG. 7B). Similar results were obtained when both 44Q and 43R residues in CEACAM1 were mutated (FIG. 5). The reciprocal mutant 0.221/CCM6-L44Q was not recognized by 5F4 mAb, suggesting that it is not the only factor crucial for conferring the appropriate conformation for 5F4 (FIG. 7A). Compatible with the latter observation, no binding of CEACAM1-Ig to 0.221/CCM6-L44Q could be detected (FIG. 7B). Point mutation in the 43R residue of CEACAM1 did not affect 5F4 mAb binding (FIG. 7A), suggesting that by itself the 43R residue had no significant effect on conformation of 5F4-recognized epitope. Despite that, the CEACAM1-Ig fusion protein did not recognize 0.221/CEACAM1-R43A cells (FIG. 7B). Elements of CEACAM1 other than the presence of the 5F4 epitope and the presence of the 44Q residue may play a crucial role in CEACAM1 binding. In this regard, it should be noted that the expression level of 0.221/CCM1-R43A obtained was lower than the expression levels of the other transfectants (FIG. 7A), which might account for the lack of efficient binding of CEACAM1-Ig. Therefore, to test whether the 43R residue by itself can confer CEACAM1 binding, the 43S of CEACAM6 was replaced with 43R. The 0.221/CCM6-S43R cells were not stained by either the 5F4 mAb (FIG. 7A) or the CEACAM1-Ig fusion protein (FIG. 7B). Gain-of-binding of CEACAM1-Ig to CEACAM6 was evident only when both 43S and 44L residues were replaced with 43R and 44Q, respectively (FIG. 5A). Thus, both 43R and 44Q residues are critical for interaction with CEACAM1.

These binding results were also confirmed in functional killing assays. To optimize the isolation of the experimental variables, the YTS NK tumor line was used. The NK tumor line YTS was either mock-transfected (YTS/control) or transfected with CEACAM1 protein (YTS/CCM1) as previously described (7) and tested in killing assays against the various 0.221 transfectants. The function of CEACAM1 protein in YTS/CCM1 cells was confirmed, because killing of 0.221/CEACAM1 cells was inhibited compared with killing by YTS/control cells, whereas 0.221/CEACAM6 and 0.221/CCM6-TailCCM1 cells were killed with similar efficiency (FIG. 7C). In agreement with the CEACAM1-Ig binding results, the inhibition of YTS/CCM1 cells was abolished when the 0.221/CCM1-RQ43,44SL and 0.221/CCM1-Q44L transfectants were used as targets (FIG. 7c), demonstrating the critical role of residue 44Q. In agreement with the above observation, the presence of 44Q only is not enough to confer inhibition, and only a mild inhibitory effect was observed when the 0.221/CCM1-R43A cells were used (FIG. 7c). This result was also supported by the observation that inhibition of YTS/CCM1 cells by heterophilic interactions with CEACAM6 was observed only with the 0.221/CCM6-SL43, 44RQ double mutation, whereas no inhibition was observed when 0.221/CCM6-S43R or 0.221/CCM6-L,44Q cells were used (FIG. 7C). Similar results were obtained with primary NK clones. Both R and Q residues in positions 43 and 44, respectively, are required for functional interaction with CEACAM1.

CEACAM1 can heterophilically interact with the CEACAM5 protein (12). The CEACAM5 protein is the only CEACAM family member other than CEACAM1 that contains 43R44Q residues (FIG. 4). The interactions between CEACAM1 and CEACAM5 was also examined. The expression level of 0.221/CEACAM5 transfectant was monitored with Kat4c and was similar to that of the other CEACAM transfectants (FIG. 7D). The 0.221/CEACAM5 cells were not stained by the anti-CEACAM1-specific 5F4 mAb (FIG. 7D). Efficient heterophilic binding of the CEACAM1-Ig fusion protein to 0.221/CEACAM5 was observed (FIG. 7D).

Modulation of CEACAM1 Activity in Adoptive Immunotherapy

Adoptive immunotherapy is a general term describing the transfer of immunocompetent cells (i.e. lymphocytes) to a patient for the treatment of a disease, such as cancer. For example, a cancer patient's immune system is sometimes capable of delaying tumor progression and on rare occasions can eliminate the tumor altogether. A variety of immunologic therapies designed to stimulate the patient's own immune system exist. For example, passive non-specific immunotherapy might involve the transfer of lymphokine activated killer cells. Another example is passive specific immunotherapy, including the transfer of specific immune cells such as cytotoxic T-lymphocytes or lymphocytes producing specific antibodies.

One example of adoptive immunotherapy involves removing lymphocytes from the patient, boosting their anti-cancer activity, growing them in large numbers, and then returning them to the patient. For example, stronger response against tumor cells is obtained using lymphocytes isolated from the tumor itself. These tumor-infiltrating lymphocytes (TILs) are grown in the presence of IL-2 and returned to the body to attack the tumor. Researchers are also using radiolabeled monoclonal antibodies for tumor antigens to even more closely identify lymphocytes specific for tumor cells.

One object of the present invention provides materials and/or for enhancing the efficacy of Tumor Infiltrating Lymphocyte based therapy in the treatment of cancer, which includes the modulation of CEACAM1 function in a population of Tumor Infiltrating Lymphocytes. The method may involve, for example, the disruption of a CEACAM1 protein-protein interaction, that may be either homotypic or heterotypic. The method may also involve, for example, the negative modulation of CEACAM1 gene expression and/or translational efficiency in a population of Tumor Infiltrating Lymphocytes.

Strategies and Protocols for TIL Isolation, Expansion and Treatment

One major challenge in adoptive immunotherapy is to develop immune cells with specific antitumor reactivity that could be generated in large enough quantities for transfer to tumor bearing patients. The lymphocytes infiltrating a tumor (TILs) are both cytotoxic and helper T cells and have specific antitumor activity, presumably because they recognize specific tumor antigens. TIL therapy involves harvesting the tumor-infiltrating lymphocytes from the tumor itself and then isolating the cells by growing single cell suspensions from the tumor. After several weeks of culture in the presence of IL-2, the activated TIL cells are transfused back into the patient [Rosenberg S A, Lotze M T, Yang J C et al. Prospective randomized trial of high-dose interleukin-2 alone or in conjunction with lymphokine-activated killer cells for the treatment of patients with advanced cancer. *J Nat Cancer Inst* 1993; 85:622-32. This reference is herein incorporated by reference.] This technique may require an additional biopsy procedure for the sole purpose of harvesting a portion of tumor for subsequent isolation of the TILs.

When cultured in the presence of IL-2, TILs can be activated and expanded in great numbers. TILs can be prepared from primary or metastatic tumors. The specimens are excised and digested in an enzyme solution, and the sterile, single-cell suspension is incubated in the presence of IL-2. In three to four weeks, an activated T-lymphocyte population is generated, and approximately 1011 cells are reinfused into the patient together with IL-2. The lymphocyte subpopulations vary according to the histology of the original tumor, culture conditions, IL-2 concentration, and other variables. The expansion of Human Tumor-Infiltrating Lymphocytes has been characterized under different conditions. There are many strategies and protocols for TIL isolation, expansion and treatment, including for example, the following references, which are herein incorporated by reference:

[Yannelli J R, Wroblewski J M., On the road to a tumor cell vaccine: 20 years of cellular immunotherapy, Vaccine. 2004 Nov. 15; 23 (1):97-113. This reference is herein incorporated by reference.]

[Yamaguchi Y et al., Adoptive immunotherapy of cancer using activated autologous lymphocytes—current status and new strategies, Hum Cell. 2003 December; 16 (4):183-9. This reference is herein incorporated by reference.]

[Colin C. Malone et al. *Characterization of Human Tumor-Infiltrating Lymphocytes Expanded in Hollow-Fiber Bioreactors for Immunotherapy of Cancer. Cancer Biotherapy & Radiopharmaceuticals*. October 2001, Vol. 16, No. 5: 381-390. This reference is herein incorporated by reference.]

[Whiteside T L, Miescher S, Hurlimann J, Moretta L, von Fliedner V. Separation, phenotyping and limiting dilution of T lymphocytes infiltrating human solid tumors. *Int J Cancer* 1986; 37:803-11. renal cell carcinoma. *J Urol* 1993; 150:1384-90. This reference is herein incorporated by reference.]

[Rosenberg S A, Speiss P, Lafreniere R. A new approach to adoptive immunotherapy of cancer with tumor-infiltrating lymphocytes. *Science* 1986; 233:1318-21. This reference is herein incorporated by reference.]

[Knazek R A, Wu Y W, Aebersold P A, Rosenbeg S A. Culture of tumor infiltrating lymphocytes in hollow fiber bioreactors. *J Immunol Methods* 1990; 127:29-37. This reference is herein incorporated by reference.]

[Bukowski R M, Sharfman W, Murthy S, et al. Clinical results and characterization of tumor-infiltrating lymphocytes with or without recombinant interleukin-2 inhuman metastatic renal cell carcinoma. *Cancer Res* 1991; 51:4199-4205. This reference is herein incorporated by reference.]

[Lewko W M, Good R W, Bowman D, Smith T K, Oldham R K. Growth of tumor derived activated T-cells for the treatment of cancer. *Cancer Biother* 1994; 9:211-24. This reference is herein incorporated by reference.]

[Hillman G G, Wolf M L, Montecillo E, Younes E, Ali E, Pontes J E, Haas G P. Expansion of activated lymphocytes obtained from renal cell carcinoma in an automated hollow fiber bioreactor. *Cell Transplant* 1994; 3:263-271. This reference is herein incorporated by reference.]

[Yannelli J R, Hyatt C, McConnell, et al. Growth of tumor-infiltrating lymphocytes from human solid cancers: summary of a 5-year experience. *Int J Cancer* 1996; 65: 413-22. This reference is herein incorporated by reference.]

[Schiltz P M, Beutel L D, Nayak S K, Dillman R O. Characterization of tumor infiltrating lymphocytes derived from human tumors for use as adoptive immunotherapy of cancer. *J Immunother* 1997; 20:377-386. This reference is herein incorporated by reference.]

[Topalian S L, Solomon D, Avis F P, et al. Immunotherapy of patients with advanced cancer using tumor-infiltrating lymphocytes with recombinant interleukin-2: a pilot study. *J Clin Oncol* 1988; 6:839-53. This reference is herein incorporated by reference.]

[Rosenberg S A, Packard B S, Aebersold P M, et al. Use of tumor infiltrating lymphocytes and interleukin-2 in the immunotherapy of patients with metastatic melanoma: a preliminary report. *N Engl J Med* 1988; 319: 1676-80. This reference is herein incorporated by reference.]

[Kradin R L, Kurnick J T, Lazarus D S, et al. Tumor-infiltrating lymphocytes and interleukin-2 in treatment of advanced cancer. *Lancet* 1989; 18:577-80. This reference is herein incorporated by reference.]

[Dillman R O, Oldham R K, Barth N M, et al. Continuous interleukin-2 and tumor-infiltrating lymphocytes as treatment of advanced melanoma; a National Biotherapy Study Group trial. *Cancer* 1991; 68:1-8. This reference is herein incorporated by reference.]

[Oldham R K, Dillman R O, Yannelli J R, et al. Continuous infusion interleukin-2 and tumor-derived activated cell as treatment of advanced solid tumors; a National Biotherapy Study Group. *Molec Biother* 1991; 3:68-73. This reference is herein incorporated by reference.]

[Belldegrun A, Pierce W, Kaboo R, et al. Interferon-a primed tumor-infiltrating lymphocytes combined with interleukin-2 and interferon-a as therapy for metastatic renal cell carcinoma. *J Urol* 1993; 150:1384-90. This reference is herein incorporated by reference.]

[Rosenberg S A, Yannelli J R, Yang J C, et al. Treatment of patients with metastatic melanoma with autologous tumor infiltrating lymphocytes and interleukin-2. *J Natl Cancer Inst* 1994; 86:1159-66. This reference is herein incorporated by reference.]

[Goedegebuure P S, Douville L M, Li H, et al. Adoptive immunotherapy with tumor-infiltrating lymphocytes and interleukin-2 in patients with metastatic malignant melanoma and renal cell carcinoma: a pilot study. *J Clin Oncol* 1995; 13:1939

[Fuji K, Karachi H, Takakuwa K, et al. Prolonged disease-free period in patients with advanced epithelial ovarian cancer after adoptive transfer of tumor-infiltrating lymphocytes. *Clin Cancer Res* 1995; 1:501-7.]

[Queirolo P, Ponte M, Gipponi M, et al. Adoptive immunotherapy with tumor infiltrating lymphocytes and subcutaneous recombinant interleukin-2 plus interferon alfa-2a for melanoma patients with nonresectable distant disease: a phase I/II pilot trial. *Ann Surg Oncol* 1999; 6:272-278.]

[Semino C, Martini L, Queirolo P, et al. Adoptive immunotherapy of advanced solid tumors: an eight year clinical experience. *Anticancer Research* 1999; 19: 5645-5650.]

Example 2

Biological Function of the Soluble CEACAM1 Protein and Implications in TAP2-Deficient Patients Interactions of natural killer (NK) cells with MHC class I proteins provide the main inhibitory signals controlling NK killing activity. However, TAP2-deficient patients suffer from autoimmune manifestations only occasionally in later stages of life. The present inventors have demonstrated that the CEACAM1-mediated inhibitory mechanism of NK cytotoxicity plays a major role in controlling NK autoreactivity in three newly identified TAP2-deficient siblings. This novel mechanism probably compensates for the lack of MHC class I mediated inhibition. The CEACAM1 protein can also be present in a soluble form and the biological function of the soluble form of CEACAM1 with regard to NK cells was investigated by the present inventors. In this section, the present inventors will show that the homophilic CEACAM1 interactions are abrogated in the presence of soluble CEACAM1 protein in a dose-dependent manner. Importantly, the amounts of soluble CEACAM1 protein detected in sera derived from the TAP2-deficient patients were dramatically reduced as compared to healthy controls. This dramatic reduction does not depend on the membrane-bound metalloproteinase activity. The present inventors demonstrated that the expression of CEACAM1 and the absence of soluble CEACAM1 observed in the TAP2-deficient patients practically maximize the inhibitory effect and probably help to minimize autoimmunity in these patients.

In this section, the present inventors will show that the soluble CEACAM1 protein blocks the CEACAM1-mediated inhibition of NK cell killing activity in a dose-dependent manner. Moreover, the present inventors will demonstrate that serum CEACAM1 levels among the TAP2-deficient patients are decreased when compared to normal individuals, in agreement with the dominant role of the CEACAM1-mediated inhibition in controlling NK autoreactivity in TAP2-deficient patients. (Gal Markel et al., Biological function of the soluble CEACAM1 protein and implications in TAP2-deficient patients, *Eur. J. Immunol.* 2004. 34: 2138-2148. This reference is herein now incorporated by reference.)

Materials and Methods

Cells

The cell lines used in this work were 721.221 (0.221) cells and 0.221 cells stably transfected with the CEACAM1 protein (0.221/CEACAM1) [17]. Primary human NK cells were isolated and cultures maintained as described [30]. An Institutional Review Board approved these studies and informed consent was provided according to the Declaration of Helsinki.

Antibodies and Fusion Proteins

The following mAb were used: anti-CEACAM1, 5, 6, 8 mAb Kat4c (DAKO), anti-NKp46 mAb 461-G1 [9, 20] and pan anti-MHC class I mAb W6/32. In addition, several fluorochrome conjugated mAb were used, including the anti-CD3-CyChrome (clone HIT3a, PharMingen), anti-CD4-FITC (clone MT310, DAKO), anti-CD8-PE (clone DK25, DAKO), anti-CD16-Biotin (clone LNK16, Serotec), anti-CD56-PE (clone B159, PharMingen) and the Kat4c-FITC (DAKO). Polyclonal rabbit anti-human CEACAM (DAKO) antibodies were used for blocking in killing assays and the rabbit anti-ubiquitin antibodies were used as control. The production and purification of the LIR1-Ig [48], KIR2DL2-Ig [49], CEACAM1-Ig [19] and CD99-Ig [7] were performed as described [19].

Flow Cytometry

Multiple staining analyses of PBL were performed with the following fluorochrome-conjugated antibodies: anti-CD3-CyChrome, anti-CD 16-Biotin followed by streptavidin-Cy5 (Jackson ImmunoResearch), anti-CD56-PE and anti-CEACAM-FITC. Another set of antibodies used, included the anti-CD3-CyChrome, anti-CD4-FITC and the anti-CD8-

PE. Cells were pretreated with 20% human serum to block nonspecific binding and control antibodies matching in isotype as well as in the fluorochrome were used as background. Staining with the various Ig-fusion proteins was performed as previously described [17, 19].

Detection of Serum CEACAM1 Level by ELISA

A standard sandwich ELISA protocol was used to quantify the amount of soluble CEACAM1 protein in the serum. The specific anti-CEACAM1 5F4 mAb was used as capturing antibody. For detection, biotinylated Kat4c mAb was used, followed by streptavidin-horseradish peroxidase (Jackson ImmunoResearch). Biotinylation of the Kat4c mAb was performed with Sulfo-SS-Biotin (Pierce) according to the manufacturer's instructions. The quantification was calculated according to standard samples of CEACAM1-Ig fusion proteins.

Killing Assays

The cytotoxic activity of NK cells against the various targets was assayed in 5-h 35S-release assays, as described [17]. In experiments where antibodies were included, the final Ab concentration was 20 ug/ml. In all assays performed, the spontaneous release did not exceed 25% of the maximal labeling.

MBMP Assays

Cells were tested for surface expression of various proteins following activation of MBMP with PMA [34-36]. Tested cells were distributed at 5×104 cells/well in 96-well U-bottom plates in 200 ul RPMI 1640 (Sigma) supplemented with 10% heat-inactivated FCS. When PMA was included the final concentration was 4 ng/ml. The final concentration of the metalloproteinase inhibitor BB-94 was 2 uM. The cells were incubated in a 5% CO2 humidified incubator at 37° C. for 2 hours, washed twice and analyzed by FACS.

Characterization of PBL Subpopulations in TAP2-Deficient Patients

Figure 8:
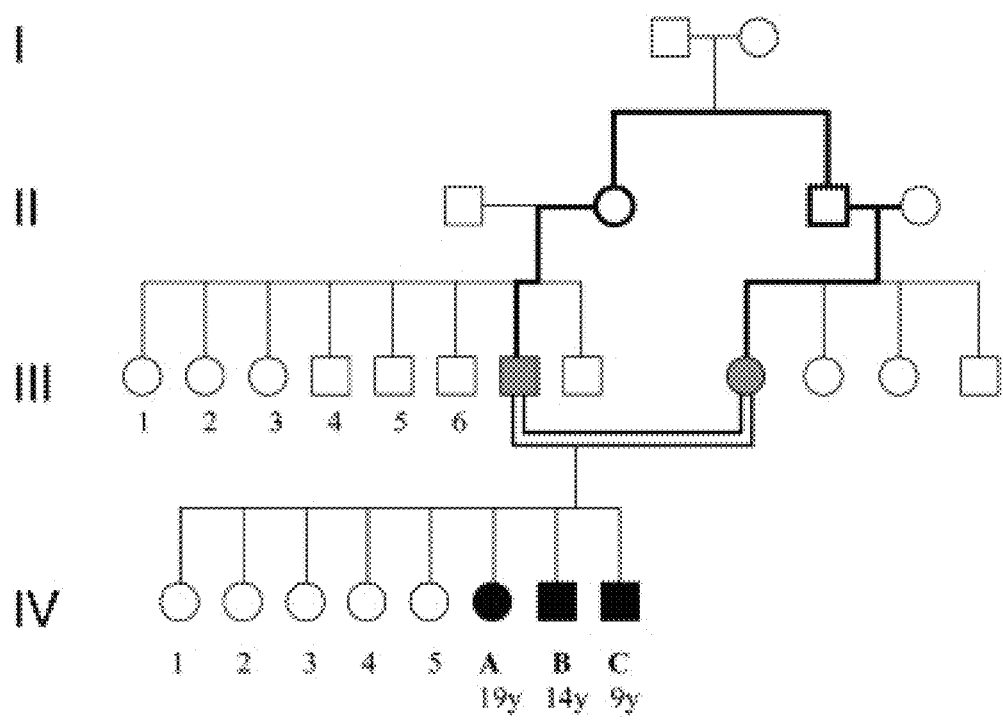
FIG. 8. Family pedigree of the TAP2-deficient patients. Patients are indicated as black symbols, the parents as gray symbols and all other healthy family members as white symbols. Cousin marriage is represented by a double line. Roman numerals indicate the generations, whereas Arabic numerals indicate individuals.

Three new siblings were identified that suffer from a deficiency in the TAP2 subunit [20]. This deficiency is inherited in an autosomal recessive pattern (FIG. 8). The siblings, patients A, B and C (19-year-old female, 14 and 9 years old males, respectively) displayed several clinical manifestations, similar to those displayed by other TAP2-deficient patients [24-26]. The other five sisters, as well as the parents, who are first cousins, showed no clinical symptoms and are considered healthy (FIG. 8).

PBL were obtained from the three patients, as well as from a healthy sister. All three patients had normal values of lymphocytes among their peripheral blood. The cells were stained for CD56 and CD3 expression to differentiate between various lymphocyte subpopulations, including NK cells (CD56+ CD3−), T cells (CD56− CD3+) and NKT cells (CD56+ CD3+). Normal distribution of these subpopulations could be observed among the three patients (FIG. 9A), implying that even the low level of MHC class I expression observed in the patients [20] is still sufficient to select for proper development of lymphocyte subpopulations.

Figure 9:
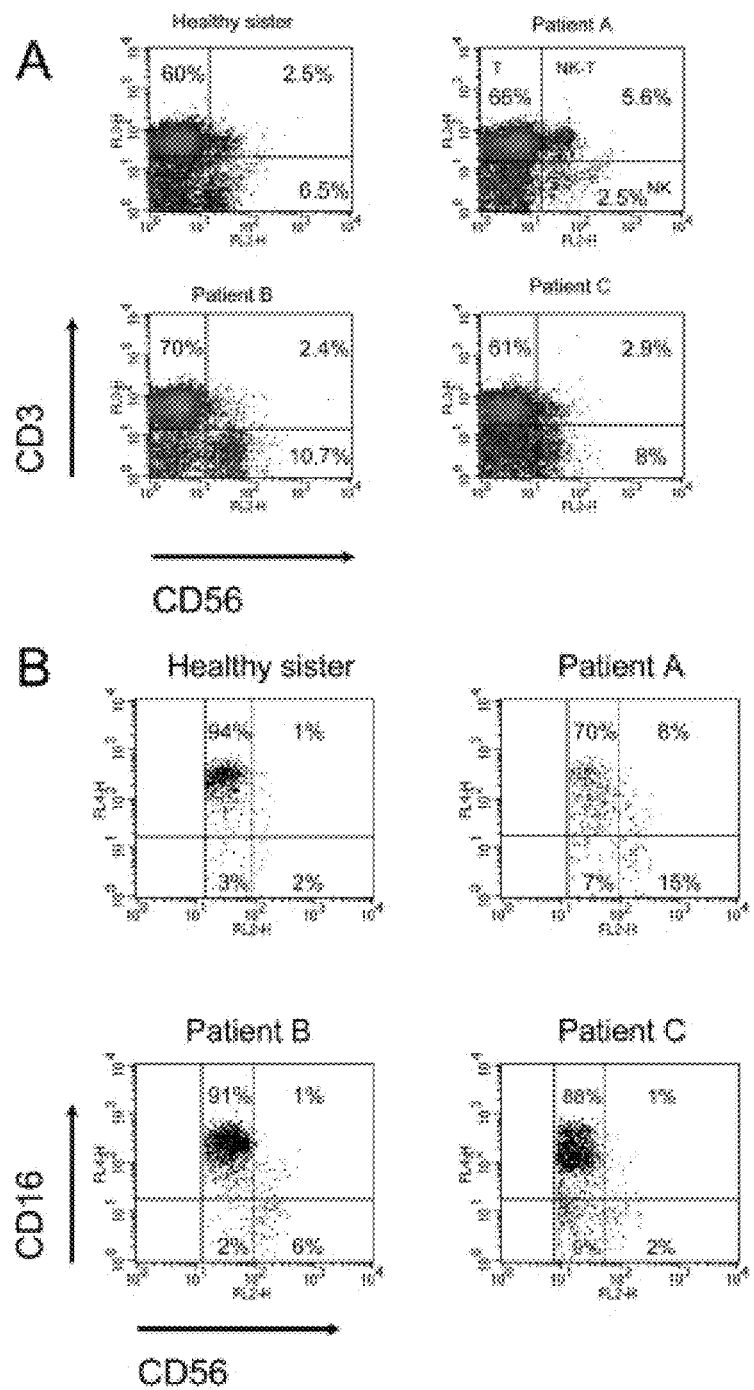
FIG. 9. PBL characterization of TAP2-deficient patients. (A) PBL obtained from the patients and from the healthy sister was stained for CD3 and CD56. (B) Staining of PBL obtained from the patients and from the healthy sister for CD3, CD56 and CD16. The dot plots analysis presented shows CD16 and CD56 expression on already gated NK cells. The vertical dashed lines discriminate CD56dim from CD56bright. For (A) and (B) one representative experiment out of three performed is shown.

Expression analysis of various MHC class I recognizing NK inhibitory receptors on NK cells obtained from the patients revealed marked changes [20]. Therefore, the expression pattern of the CD16 and the CD56 on the freshly isolated NK cells were further characterized. Patient A exhibited an increase in the percentage of CD16− subpopulation (22%) as compared to the healthy sister (5%) (FIG. 9B), whereas patients B and C displayed a milder trend (8% and 11%, respectively) (FIG. 9B). Moreover, double staining showed a skewing in the different subpopulations between the three patients and the healthy sister; the CD56dim CD16− subset was increased in patients A (7%) and C (9%) compared to the healthy sister (3%) (FIG. 9B), the CD56bright CD16− subset was markedly increased in patients A (15%) and B (6%) compared to the healthy sister (2%) (FIG. 9B) and the CD56bright CD16+ subset was increased only in patient A (8%) compared to the healthy sister (1%) (FIG. 9B). The NKp46 expression on NK cells was impaired in all patients as compared to the healthy sister, most prominently in patient A (Table 1). A remarkable difference in the CD4/CD8 ratio was observed among the T cell subpopulations; 65% of the T cells from the healthy sister expressed the CD4 receptor and 35% the CD8. There were no double-positive CD4+CD8+ T cells. In contrast, CD4 was detected on the surface of 91%, 92% and 87% of the T cells analyzed from patients A, B and C, respectively (Table 1). CD8 was detected on the surface of 9%, 8% and 13% of the T cells analyzed from patients A, B and C, respectively (Table 1). A similar skew in the CD4/CD8 ratio was also observed among T cells in other TAP2-deficient patients [24].

TABLE 1

| Subject | Subpopulation | Receptor expression[1] | | |
|---|---|---|---|---|
| | | CD4 | CD8 | NKp46 |
| Patient A | NK | — | — | <5% |
| | T | 91% | 9% | 0% |
| Patient B | NK | — | — | 60% |
| | T | 92% | 8% | 0% |
| Patient C | NK | — | — | 20% |
| | T | 87% | 13% | 0% |
| Sister | NK | — | — | 100% |
| | T | 65% | 35% | 0% |

[1]Percentages of the expression of the indicated receptors on NK cells derived from patients A, B, C and their healthy sister.

Loss of MHC Class I Mediated Inhibition in TAP2-Deficient Patients

Figure 10:
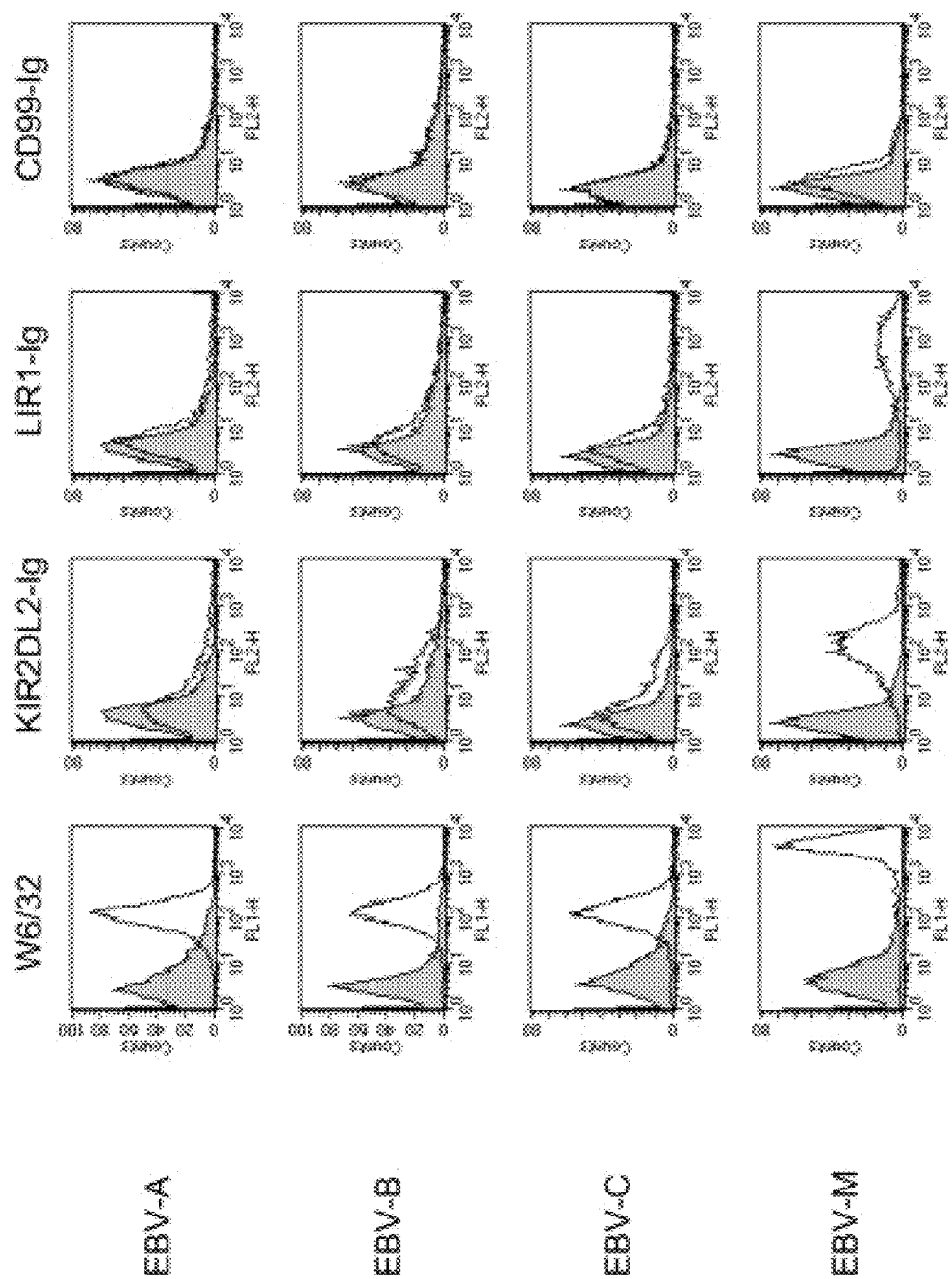
FIG. 10. Lack of recognition of the patients' cells by KIR2DL2-Ig and LIR1-Ig. The various EBV cell lines were stained with mAbW6/32 or with various Ig-fusion proteins. The secondary F(ab')2 detection antibodies alone were used as background. One representative experiment out of four performed is shown.

Polyclonal EBV-transformed B cell lines were generated from patients A, B and C (EBV-A, -B and -C, respectively) as well as from the healthy mother (EBV-M). These cells were stained for MHC class I expression using W6/32 mAb. A 30-fold reduction in the expression of MHC class I proteins was observed on EBV-A, -B and -C as compared to EBV-M (FIG. 10). Nevertheless, despite the deficiency in the TAP2 subunit, some MHC class I alleles were still expressed on cell surface (FIG. 10). The MHC haplotype of all patients is HLA-A*03, B*07, Bw6, Cw*07, DRB1*15, DRB5 and DQB1*06. The low expression of MHC class I proteins in the patients' cells is allele specific, as no expression was observed when an mAb specific for HLA-A*03 was used [20]. Next, it was tested whether the low levels of MHC class I proteins are still sufficient for interactions with inhibitory NK receptors. EBV-A, -B, -C and -M cells were stained with the KIR2DL2-Ig, recognizing HLA-Cw7 [27] that is present on the patients' cells, and with the LIR1-Ig that recognizes a broad spectrum of HLA proteins [28]. As expected, EBV-M cells were efficiently stained by both the KIR2DL2-Ig and LIR1-Ig (FIG. 10). In contrast, little or no staining was observed on EBV-A, -B or -C cells (FIG. 10).

Unusual, CEACAM1 Expression on NK CELLS Derived from TAP2-Deficient Patients

Figure 11:
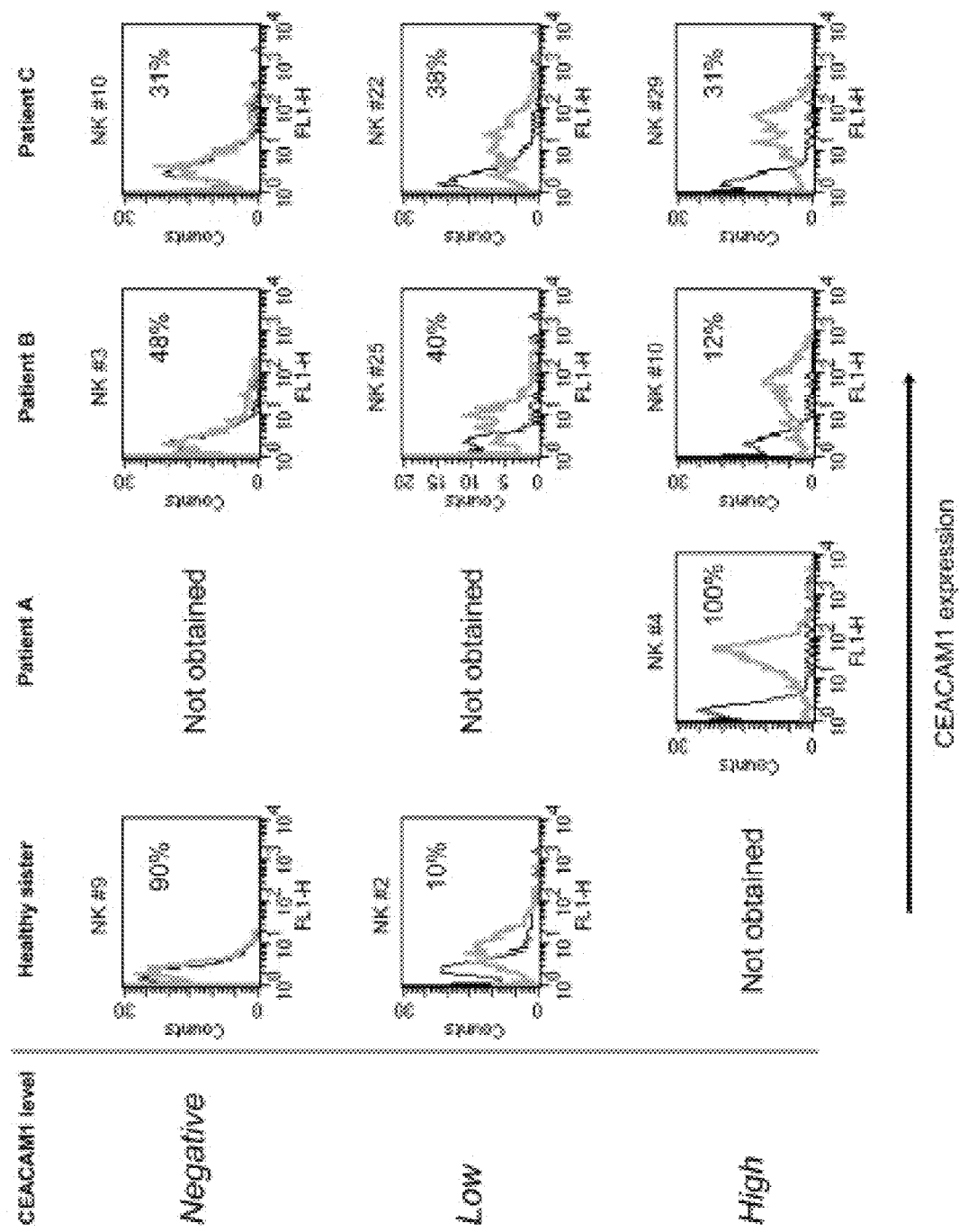
FIG. 11. High expression of CEACAM1 on activated TAP2-deficient NK cells. NK clones expressing CEACAM1 were divided into groups according to expression level of CEACAM1 (indicated on the left). CEACAM1 expression on one representative NK clone of each group is shown. The percentages of the NK clones similar to the NK clone presented in each donor are indicated in each histogram.

Fresh NK cells derived from the three TAP2-deficient patients as well as from the healthy sister were negative for CEACAM1 expression [20]. The purified NK cells were next activated with IL-2 and grown either as bulk cultures or as NK clones. CEACAM1 expression was monitored using the 5F4 mAb [29]. As reported [17, 19], around 90% of the NK clones obtained from the healthy sister or the mother did not express CEACAM1 (FIG. 11). Strikingly, all of the NK clones (100%) obtained from patient A expressed the CEACAM1 in unusually high levels (30-fold above background). (see for example NK clone 2 in the healthy sister in FIG. 11, and [17, 19]). Of the NK clones obtained from patient B, 52% expressed the CEACAM1 protein in low or high levels (FIG. 11), whereas 69% of the NK cells derived from patient C expressed CEACAM1 in low or high levels (FIG. 11).

Figure 12:
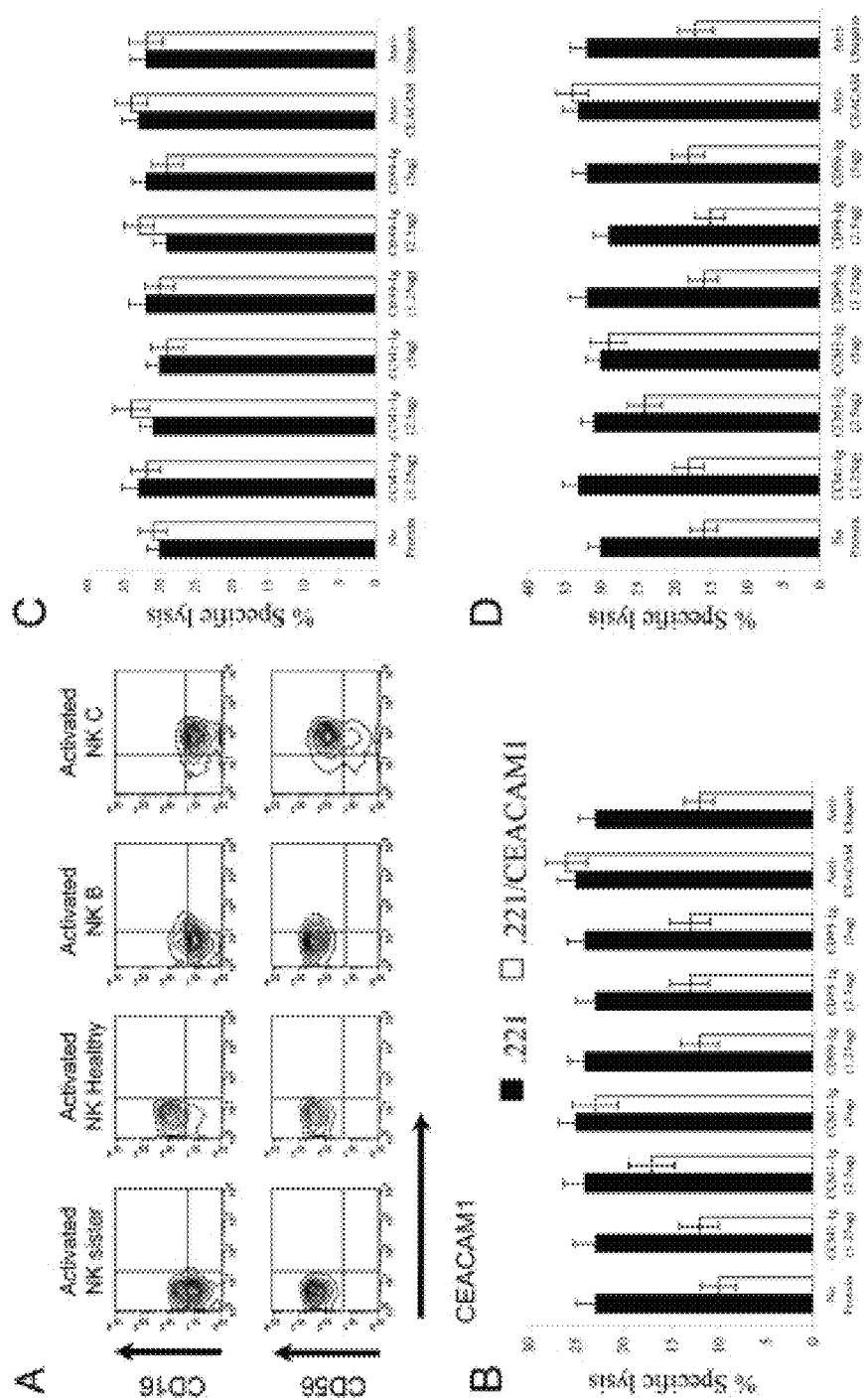
FIG. 12. CEACAM1-mediated inhibition of NK killing activity is blocked by the soluble CEACAM1-Ig. (A) Bulk NK cultures were stained for CD16, CD56 and CEACAM1. Contour plot X-axis is CEACAM1 log fluorescence and Y-axis is CD16 or CD56 log fluorescence. One representative experiment out of two performed is shown. (B-D) Killing of 0.221 and 0.221/CEACAM1 cells, incubated with various amounts of the CEACAM1-Ig (CCM1-Ig) fusion protein or the anti-CEACAM antibodies. Killing assays were performed with NK-B cells (B), CEACAM1− NK-M cells (C) or CEACAM1+ NK-Y cells (D). The E:T ratio was 2:1. For (B-D), the average of three independent experiments is shown.

Activated bulk NK cultures were next assessed for the expression of CD3, CD16, CD56 and CEACAM1. The minor CEACAM1-positive population could not be observed when the activated bulk NK cultures derived either from the healthy sister or from an unrelated healthy donor (NK-Y) were analyzed (FIG. 12A). In contrast, an up-regulation of CEACAM1 was observed on the bulk activated NK cells derived from patient B. An up-regulation in the CEACAM1 expression was observed on bulk activated NK cells derived from patient C that was associated with a moderate down-regulation in the expression of the CD16 and a reduction in the CD56 expression (FIG. 12A). The CD16 expression on the surface of NK cells obtained from the healthy sister was lower than in the unrelated healthy donor; nevertheless, no CEACAM1 expression was observed (FIG. 12A).

CEACAM1-Mediated Inhibition of NK Cytotoxicity is Abrogated by Soluble CEACAM1

CEACAM1 controls NK autoreactivity in TAP2-deficient patients [20]. Therefore, the maintenance of the CEACAM1-inhibitory interactions is critical in these patients. CEACAM1-Ig was used to investigate the effect of soluble CEACAM1 on NK-mediated killing. NK clones and bulk cultures were tested in killing assays against the 721.221 (0.221) cells and the CEACAM1-transfected 0.221 cells (0.221/CEACAM1) as described [30]. The bulk NK cultures obtained from patient B (NK-B) efficiently killed the 0.221 cells (FIG. 12B), but were inhibited by the 0.221/CEACAM1 cells (FIG. 12B). This is in agreement with the unusually high expression of the CEACAM1 protein on the surface of NK cells derived from the TAP2-deficient patients (FIG. 11, 12A, and [20]). The inhibition observed with the bulk NK cells derived from the patients was the result of the homophilic CEACAM1 interactions, as lysis was restored in the presence of blocking anti-CEACAM antibodies (FIG. 12B). Remarkably, the CEACAM1-mediated inhibition was abrogated in the presence of the soluble CEACAM1-Ig in a dose-dependent manner, reaching maximal effect in 5 ? g/well (FIG. 12B). In addition, the presence of either CEACAM1-Ig or CD99-Ig did not affect the killing activity of CEACAM1– bulk NK cultures obtained from a healthy donor, thus ruling out nonspecific increased killing due to antibody-dependent cellular cytotoxicity (FIG. 12C). Similar results were obtained with CEACAM1+ NK cells pooled from other healthy donors (FIG. 12D).

TAP2-Deficient Patients Have Decreased Level of Serum CEACAM1

The amount of the soluble CEACAM1 protein is normally around 300 ng/ml [22], but in pathologies such as obstructive jaundice it increases to 1,500 ng/ml [22]. Induction of liver diseases in animal models leads to increased soluble CEACAM1 protein in the serum [31]. Based on the blocking activity of CEACAM1-Ig (FIG. 12B, D), it is possible that serum CEACAM1 levels might be altered in TAP2-deficient patients. This is supported by other receptors that are also biologically active in soluble forms such as the Semaphorin CD100/Sema4D [32].

Figure 13:
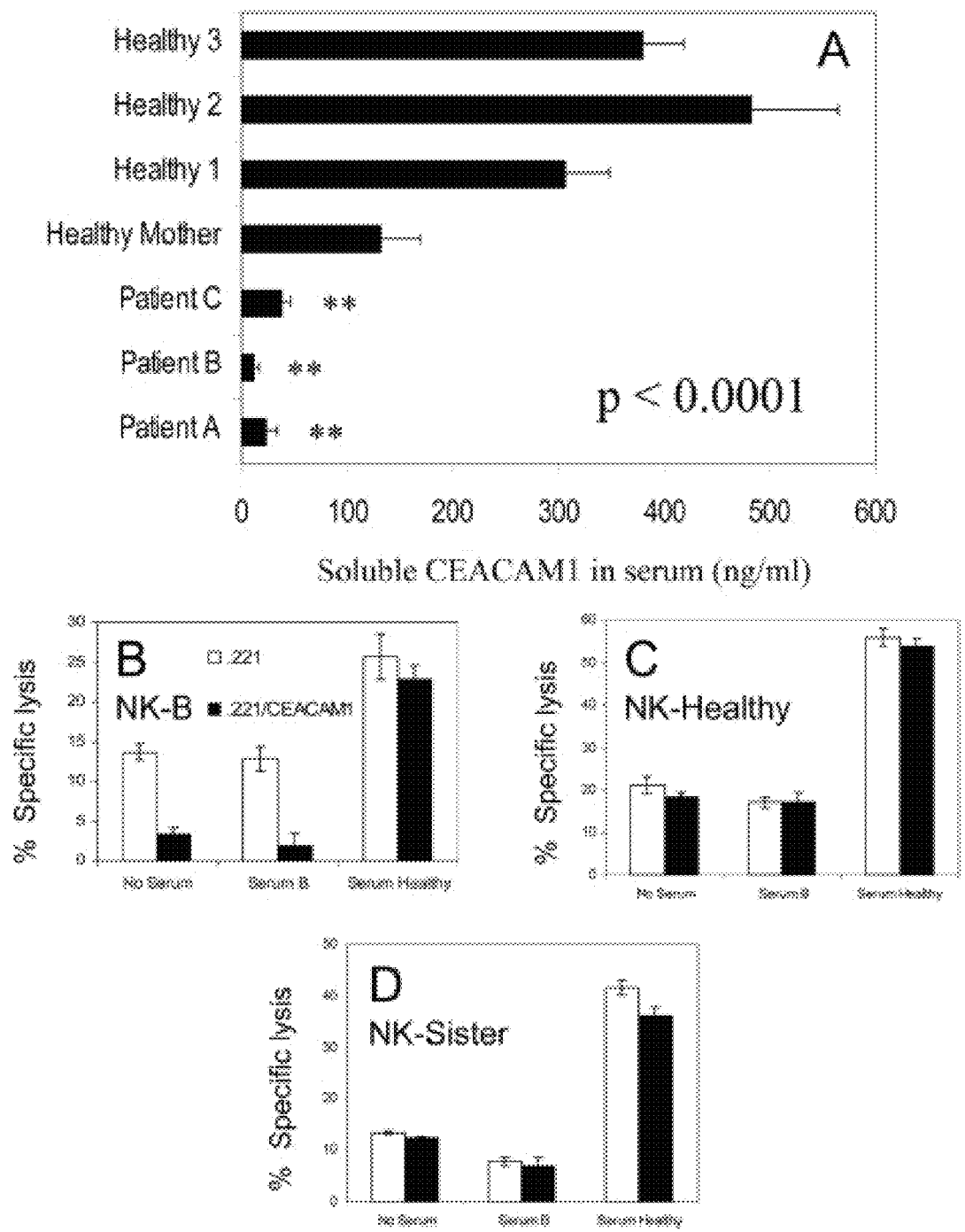
FIG. 13. Decreased level of soluble CEACAM1 protein in the serum of TAP2-deficient patients. (A) Serum samples were analyzed for the presence of soluble CEACAM1 by ELISA. X-axis indicates the amount of detected soluble CEACAM1. The mean of three independent experiments is shown. (B-D) Killing of 0.221 and 0.221/CEACAM1 pre-incubated either with no serum, with serum derived from patient B (Serum B) or from a healthy donor (Serum Healthy). Killing assays were performed with NK-B (B), NKHealthy (C) and with NK-Sister (D). The E:T was 2:1.

The levels of soluble CEACAM1 protein were tested in the patients' sera. CEACAM1 levels detected in the sera derived from unrelated healthy donors were similar to those previously described [22, 23] (FIG. 13A). In contrast, a striking decrease in the soluble CEACAM1 amount was observed in the sera derived from all three patients (FIG. 13A). Interestingly, although the amount of soluble CEACAM1 in the serum derived from the healthy mother was indeed significantly higher than that of the three patients, it was still significantly lower than normal (FIG. 13A). The TAP2 deficiency described here probably results from an autosomal recessive inherited defect, like other TAP2 deficiencies [24, 33]. Hence, the patients are probably homozygous for the defect causing the TAP2 deficiency and the mother is heterozygous. Therefore, the above significant differences in serum CEACAM1 levels between unrelated healthy donors, the healthy mother and the patients might be linked to zygocity.

The bulk NK cultures were next tested against 0.221 cells and against the 0.221/CEACAM1 pre-incubated either with no serum, with patient-derived serum or with serum derived from a healthy donor. The NK-B cells were inhibited by the 0.221/CEACAM1 cells either in the presence of the autologous serum or when no serum was included in the assay (FIG. 13B). This inhibition was abrogated in the presence of serum derived from a healthy donor (FIG. 13B), suggesting that the serum soluble CEACAM1 is able to block CEACAM1-mediated inhibition in vivo. No inhibition was observed when the CEACAM1-negative bulk NK cultures derived either from an unrelated healthy donor or from the healthy sister were used (FIG. 13C, D). The presence of serum from the healthy donor caused a marked increase in the killing activity of all NK cells tested (FIG. 13B-D). Similar activation of NK killing was observed with sera derived from other healthy donors, whereas sera derived from patient C had no effect. Additional differences other than the presence of CEACAM1 exist may exist.

Figure 14:
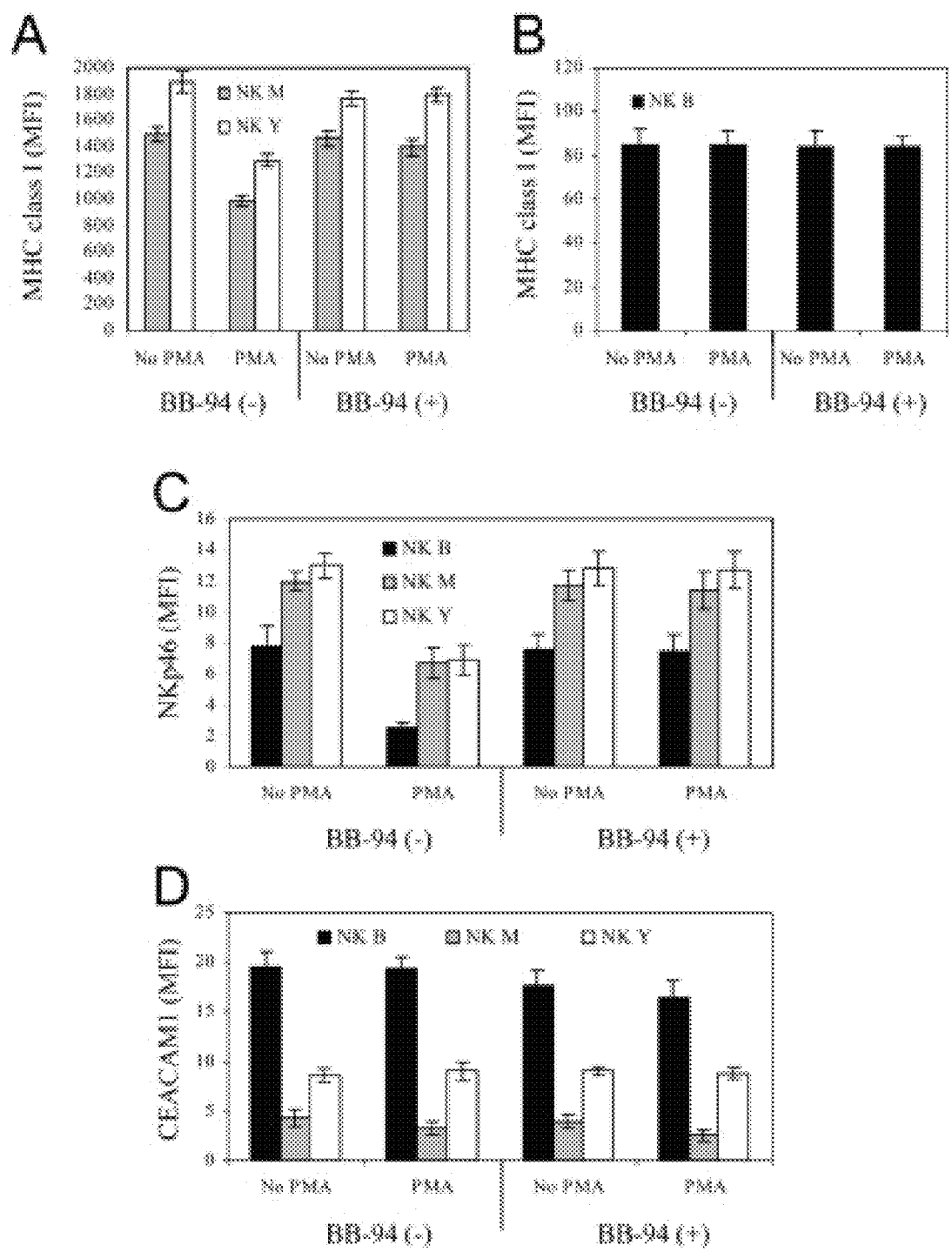
FIG. 14. Cell surface CEACAM1 level is not regulated by MBMP activity. Surface expression of the MHC class I (A, B) on NK cells derived from the mother (NK M), healthy donor (NK Y) or patient B (NK B), NKp46 (C) and the CEACAM1 protein (D). Cells were analyzed by FACS using the W6/32 (A, B), 461-G1 (C) and the Kat4c mAb (D). The tested protein is indicated on the Y-axis of each plot. Expression was analyzed following stimulation with PMA and Ca2+ ionophore. These experiments were performed either with or without the MBMP inhibitor BB-94 (indicated in the bottom of each plot). Average results of three independent experiments are shown.

Soluble CEACAM1 Protein is not Generated via Membrane-Bound Metalloproteinase Mediated Cleavage The combination of increased expression of membrane-bound CEACAM1 protein on cells derived from the TAP2-deficient patients [20], together with the significantly lower amounts of soluble CEACAM1 in the sera of the patients (FIG. 13A), suggests that NK cells in the TAP2-deficient patients have developed special mechanisms to inhibit NK activity. The soluble CEACAM1 protein found in the serum might be generated either from alternative splicing of CEACAM1 or from a cleavage of the membrane-bound CEACAM1 by membrane-bound metalloproteinase (MBMP). Whether MBMP is involved in the cleavage of CEACAM1 was tested. MBMP activity is augmented in response to cell stimulation, e.g. by PMA [34, 35], and inhibited in the presence of the inhibitor BB-94 [36]. Previous reports have demonstrated that MHC class I proteins are susceptible to external cleavage by MBMP [37]. Incubation of the NK-M or the NK-Y cells with the PMA resulted in decreased MHC class I expression (FIG. 14A). This reduction in MHC class I expression was the result of MBMP activity, because MHC class I expression level was restored in the presence of the BB-94 inhibitor (FIG. 14A). As shown above and previously (FIGS. 10, 14B and [20]), the MHC class I protein expression level on NK-B cells was significantly lower compared with the healthy donors. Surprisingly however, expression of MHC class I on the patient cells did not decrease in response to PMA (FIG. 14B). Similar results were obtained with bulk NK cultures derived from patients A and C. This may suggest that the specific MHC class I alleles expressed on TAP2-deficient cells are resistant to extracellular cleavage by MBMP. Alternatively, the activity or expression of the MBMP might be impaired in the TAP2-deficient cells.

To test the latter option, the NK-B, -M and -Y cells for the NKp46 receptor with the 461-G1 mAb were stained [9, 20]. As reported [20], expression of NKp46 was detected on the normal NK cells, NK-M and -Y. However, the NK-B cells displayed a much weaker expression (FIG. 14C). Reduction in the NKp46 expression level was observed on NK cells derived from both healthy donors and patients following incubation with PMA (FIG. 14C). The reduction in 461-G1 staining was induced by MBMP activity as NKp46 expression was restored in the presence of the BB-94 inhibitor (FIG. 14C). MBMP is active and functional in the TAP2-deficient patients.

Whether the surface CEACAM1 protein is regulated by MBMP-mediated cleavage was also tested. The NK-Y bulk culture was obtained after pooling more than 30 CEACAM1+ NK clones obtained from a healthy donor. Incubation of the various bulk NK cultures with PMA did not alter the CEACAM1 expression level (FIG. 14D). This indicated that the membrane-bound CEACAM1 protein expression level is not regulated by MBMP mediated cleavage.

Example 3

The Mechanisms Controlling NK Cell Autoreactivity in TAP2-Deficient Patients

The killing of natural killer (NK) cells is regulated by activating and inhibitory NK receptors that recognize mainly class I major histocompatibility complex (MHC) proteins. In transporter associated with antigen processing (TAP2)-deficient patients, killing of autologous cells by NK cells is therefore expected. However, none of the TAP2-deficient patients studied so far have suffered from immediate NK-mediated autoimmune manifestations. The present inventors have demonstrated the existence of a novel class I MHC-independent inhibitory mechanism of NK cell cytotoxicity mediated by the homophilic carcinoembryonic antigen-related cell adhesion molecule 1 (CEACAM1) interactions. In this section the present inventors identify 3 new siblings suffering from TAP2 deficiency. NK cells derived from these patients express unusually high levels of the various killer cell inhibitory receptors (KIRs) and the CEACAM1 protein. Importantly, the patients' NK cells use the CEACAM1 protein to inhibit the killing of tumor and autologous cells. The inventors further show that the function of the main NK lysis receptor, NKp46, is impaired in these patients. In this section the present inventors will show that the expression of the NKp46 receptor is severely impaired in a newly identified TAP2-deficient family and that the vast majority of activated NK cells derived from these patients use the CEACAM1 protein interactions to avoid tumor and autologous cell killing. These results indicate that NK cells in TAP2-deficient patients have developed unique mechanisms to reduce NK killing activity and to compensate for the lack of class I MHC-mediated inhibition. These mechanisms prevent the attack of self-cells by the autologous NK cells and explain why TAP2-deficient patients do not suffer from autoimmune manifestations in early stages of life. (Gal Markel et al., The mechanisms controlling NK cell autoreactivity in TAP2-deficient patients, Blood, 1 Mar. 2004, Vol. 103, No. 5, pp. 1770-1778. Prepublished online as a Blood First Edition Paper on Nov. 6, 2003; DOI 10.1182/blood-2003-06-2114. This reference is herein now incorporated by reference.)

Materials and Methods

Patients

Patients A, B, and C are siblings (19, 14, and 9 years old, respectively). All patients share the same human leukocyte antigen (HLA) haplotype (A*03, B*07, Bw6, Cw*07, DRB1*15, DRB5, DQB1*06). They presented with severe diffuse bronchiectasis, sinusitis, and serous otitis media with no history of severe viral infections. The Institutional Review Board of Schneider Children's Medical Center of Israel approved these studies, and informed consent was provided according to the Declaration of Helsinki.

Generation of NK Clones and Phytohaemagglutinin (PHA)-Induced T-Cell Blasts

Isolation and culturing of NK clones and bulk NK cultures were performed as described.[22] Isolation and culturing of T-cell populations were performed as described. 18

Antibodies and Immunoglobulin-Fused Proteins

The following monoclonal antibodies were used: monoclonal antibody (mAb) W6/32 and HP-1F7 directed against class I MHC molecules; anti-$\beta_2$-microglobulin mAb BBM-1, anti-CEACAM1 mAb 5F4,[23] anti-HLA-A3 GAP A3 mAb, anti-CD16 mAb B73.1.1, and anti-CD94 mAb HP-3D9 (Dako, Hamburg, Germany); the rabbit polyclonal anti-CEACAM1, CEACAM5, and CEACAM6 antibodies (Dako) that block the CEACAM1 interactions[15,18]; anti-killer cell inhibitory receptor 2DL1 (anti-KIR2DL1) mAb EB6 (ImmunoTech, Westbrook, Me.); anti-KIR2DL2 mAb GL183 (ImmunoTech); anti-leukocyte immunoglobulin-like receptor 1 (anti-LIR1) mAb HP-F1 (a kind gift from Dr López-Botet; Immunologica, Barcelona, Spain); anti-HLA-DQ mAb G46-6 (Pharmingen, San Diego, Calif.); anti-HLA-DR mAb TU36 (Pharmingen); and the anti-NKG2D mAb (R&D Systems, Minneapolis, Minn.). The specificity of all anti-CEACAM antibodies was confirmed previously.[18] The anti-NKp46 mAb 461-G1 (immunoglobulin G1 [IgG1]) was generated by immunizing mice with the NKp46-Ig fusion protein. The specificity of this mAb was determined by fluorescence-activated cell sorter (FACS) analysis on NKp46 transfectants and on NK cells (freshly isolated and IL-2 activated) (Table 4). The generation and production of fusion proteins KIR2DL2-Ig, CD99-Ig, NKp46-Ig, NKp30-Ig, and NKp44-Ig were previously described.[3,7,8]

Restoration of Class I MHC Expression by Transient B-Cell, Line Fusion

Epstein-Barr virus (EBV)-transformed B-cell lines derived from the patients were mixed either with the 721.174 (a TAP− cell line),[24] with the 721.45 (a TAP+ cell line with hemizygous MHC class I haplotype of HLA-A2, HLA-B5, and HLA-Cw1),[25] or with EBV-transformed B-cell lines derived from other TAP1- or TAP2-deficient patients. Cells to be fused were mixed together at a 1:1 ratio at a final concentration of 10×10[6]/mL and incubated for 1 hour in RPMI containing 10% fetal calf serum (FCS) and 25 µg/mL, PHA-P (Sigma, St Louis, Mo.). Cells were pelleted and resuspended in phosphate-buffered saline (PBS) containing 50% polyethylene glycol (PEG) 1500 (Sigma), and 5% dimethyl sulfoxide (DMSO) (Sigma). After incubation at 37° C. for 1 minute, cells were washed, resuspended in PBS, and incubated for a further 30 minutes at 37° C. After overnight incubation in RPMI containing 10% FCS, total fusion products were stained with GAP A3 monoclonal antibody. Cell mixtures without addition of PEG were used as negative control to rule out humoral effect.

FACS Staining, Generation of F(ab')$_2$ Fragments

FACS multistaining was performed as described.[15,18] Conjugated antibodies included Kat4c-fluorescein isothiocyanate (Kat4c-FITC) (IgG1; Dako), anti-CD56-phycoerythrin (PE) (IgG1; Dako), anti-CD3-CyChrome (IgG1; Pharmingen), anti-CD16-biotin (IgG1; Serotec, Raleigh, N.C.), and anti-NKG2D-PE (IgG1; R&D Systems). Controls were nonbinding isotype-matched fluorochrome-matched mAbs. Detection of immunoglobulin-fusion proteins was performed by means of the PE-conjugated secondary goat antihuman IgG antibodies with minimal cross-reaction (Jackson ImmunoResearch Laboratories, Bar Harbor, Me.), as described.[15,18] All FACS data in all of the figures and tables presented in this article were obtained with antibodies in the form of F(ab')$_2$. Digestion and purification of the F(ab')$_2$ fragments were performed with the ImmunoPure F(ab')$_2$ preparation kit (Pierce, Rockford, Ill.) according to the manufacturer's instructions.

Cytotoxicity Assays

The cytotoxic activity of NK cells against the various targets was assayed in 5-hour $^{35}$S-release assays, as described.[26] In experiments in which antibodies were included, the final mAb concentration was 20 µg/mL. In all assays performed, the spontaneous release did not exceed 25% of the maximal labeling.

Identification of a New Family of TAP2-Deficient Patients

A genetic defect in the class I MHC expression was identified in an Arab-Israeli family. Patients A, B, and C (19-year-old female, 14- and 9-year-old males, respectively) displayed clinical manifestations similar to those displayed by other TAP2-deficient patients.[27] The other 5 sisters as well as the parents, who are first cousins, showed no clinical symptoms. NK clones were purified from all of the patients as well from a healthy sister. Forty NK clones from each individual were analyzed by FACS for presence of class I MHC, class II MHC, and β$_2$-microglobulin by use of the W6/32 mAb, the TU36 mAb, and the BBM-1 mAb, respectively. A decrease in expression of class I MHC proteins and of β$_2$-microglobulin (approximately 20-fold) was observed on the surface of NK clones derived from the patients as compared with those derived from the healthy sister (Table 2). Analysis of class II MHC protein expression revealed only 3-fold (patient A) or 2-fold (patients B and C) reduction compared with the healthy sister (Table 2). Similar results were obtained when different types of cells, such as T cells and monocytes, were used.

To identify the genetic defect responsible for the impaired expression of class I MHC proteins observed in these patients, an EBV-transformed B-cell line was made from each patient (EBV-A, EBV-B, and EBV-C) and from their healthy mother (EBV-mother). The EBV-transformed B-cell lines were further analyzed for the expression of class I MHC, class II MHC, β$_2$-microglobulin, and HLA-A3 by using the W6/32 mAb, the TU36 and G46-6 mAbs, BBM-1 mAb, and the GAP A3 mAb, respectively. In agreement with the results described in the preceding paragraph, a dramatic down-regulation (approximately 20-fold) of class I MHC proteins and of β$_2$-microglobulin surface expression was observed on EBV-A, EBV-B, and EBV-C as compared with EBV-mother (Table 3). There was no significant difference in the expression of class II MHC proteins, such as HLA-DQ and HLA-DR (Table 3). Notably, the HLA-A3 protein was completely absent from the surface of EBV-A, EBV-B, and EBV-C, but not from EBV-mother (all patients and their mother express HLA-A3; see "methods this section"). There is a slight expression of class I MHC detected by W6/32, indicating that class I MHC proteins other than HLA-A3 are still expressed in low levels on the patient EBV cells (Table 3).

Since HLA-A3 was not detected on the patients' EBV cells, an assay that is based on the restoration of HLA-A3 expression following correction of the class I MHC biosynthetic pathway via PEG-mediated fusion of EBV-A, EBV-B, or EBV-C with various cell lines was next employed. The 721.45 cells that were used in some of the fusion experiments were hemizygous for class I MHC expression (HLA-A2, HLA-B5, and HLA-Cw1). Therefore, specific monitoring was required to discriminate between the class I MHC reconstitution (monitored by GAP A3) and the endogenous expression of the class I MHC proteins on 721.45 cells.

Figure 15:
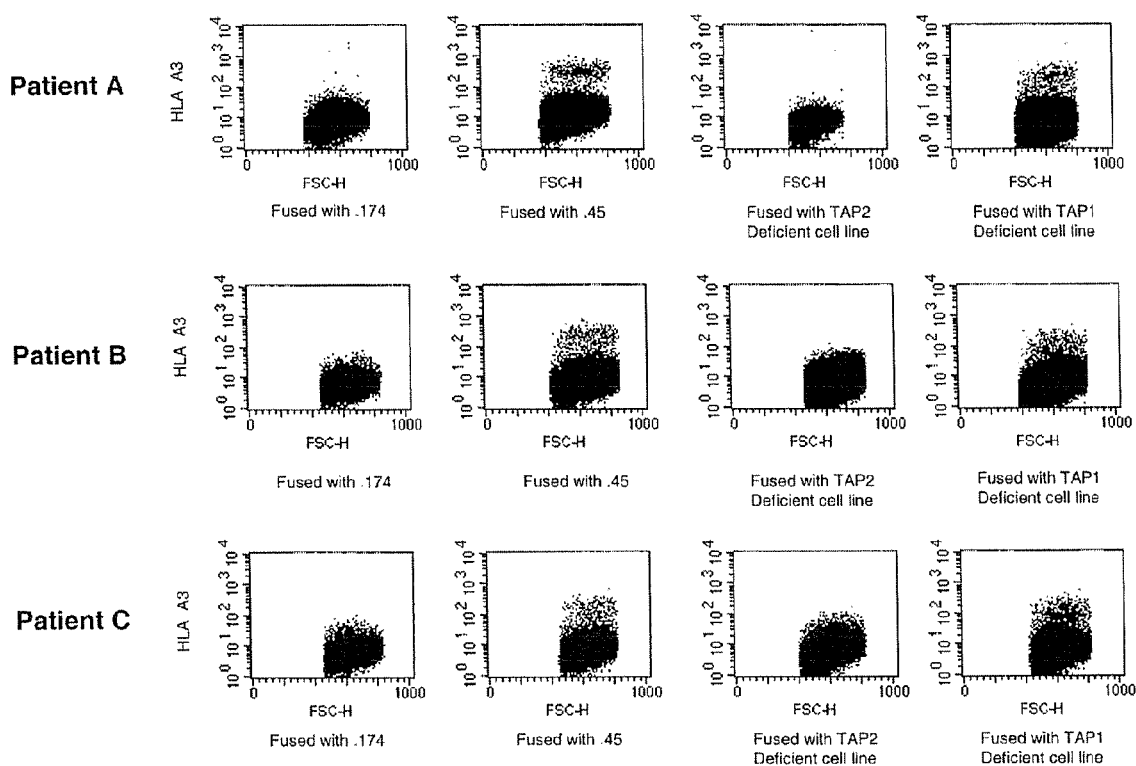
FIG. 15. The reduction in class I MHC expression is due to TAP2 deficiency. Fusion of EBV-A, EBV-B, and EBV-C with various B-cell lines defective either for the TAP1 and TAP2 subunits (0.174) or none of them (0.45). Total mixture of cells was analyzed by FACS. Fused cells were identified by HLA-A3 expression. Staining with HLA-A3 is on the y-axis, and forward scatter is on the x-axis. One representative experiment is shown of 3 performed.

Cells were fused, and the total cell mixture was analyzed with the use of the GAP A3 mAb. As not all mixed cells were fused, the fused cells were identified by the presence of HLA-A3 protein. Fusion of EBV-A, EBV-B, or EBV-C either with the 721.45 cell line that expresses both TAP1 and TAP2 subunits or with cells deficient in TAP1, resulted in the emergence of an HLA-A3$^+$ population (FIG. 15). In contrast, fusion of EBV-A, EBV-B, or EBV-C with 721.174 cell line (0.174), deficient for TAP1 and TAP2 or with B cells derived from other TAP2-deficient patients, failed to restore HLA-A3 expression (FIG. 15). The fact that mixture of EBV-A, EBV-B, or EBV-EBV-C with the various cell lines without addition of PEG failed to reconstitute HLA-A3 expression and in addition to the fact that some of the fusions performed did not restore HLA-A3 expression (FIG. 15) rule out the possibility of humoral effect. The genetic defect is in the TAP2 protein.

Impaired Expression and Function of NKp46

Figure 16:
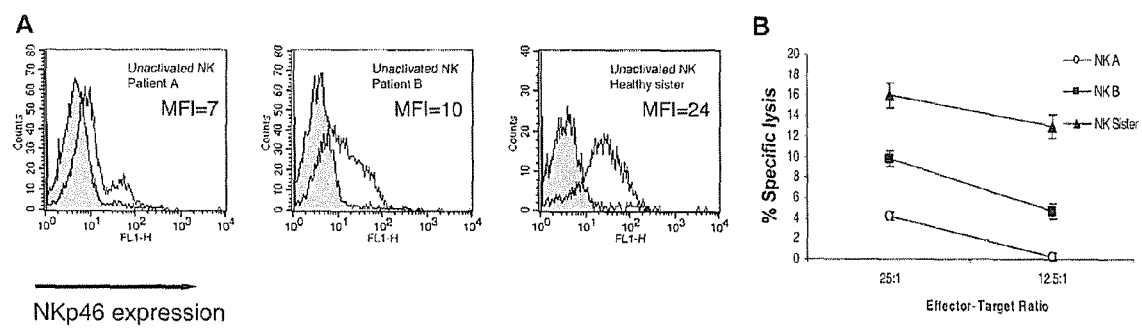
FIG. 16. Impaired expression and function of NKp46 on freshly isolated NK cells. (A) NKp46 expression on freshly isolated bulk NK cells. Staining was detected by mAb 461-G1 in the form of F(ab')$_2$, and the MFI staining is indicated in each histogram. One representative experiment is shown of 3 performed. (B) Killing of 0.221 cells by freshly isolated NK cells derived from indicated donors. The mean results of 3 independent experiments are shown. The data represent means of the percentage of killing±SDs.

NKp46 is considered to be the main NK killing receptor for NK cells and is uniquely expressed on all NK cells.[28] Expression of NKp46 on freshly isolated NK cells was monitored by using an anti-NKp46 mAb (461-G1). Relatively low levels of NKp46 were observed on the bulk NK cells isolated from the healthy sister (MFI=24) (FIG. 16A). At this stage blood samples could no longer be obtained from patient C owing to the severity of his clinical conditions. The NKp46 receptor could hardly be detected on the surface of more than 85% of the NK cells isolated from patient A (MFI=7) and on more than 60% of the NK cells isolated from patient B (MFI=10) (FIG. 16A). The function of the NKp46 receptor was assayed concomitantly against 721.221 cells, in which the lysis is controlled by the NKp46 receptor.[5] In accordance with the staining results (FIG. 16A), very low killing was observed with bulk freshly isolated NK cells derived from patient A; relatively moderate killing was observed with NK cells from patient B; and relatively efficient killing was observed with NK cells from the healthy sister (FIG. 16B).

IL-2-activated NK clones from the patients and from the healthy sister were next generated. No major difference in the NKp46 expression was observed between freshly isolated and IL-2-activated NK cells (FIG. 16A; Table 4). Activated NK clones were analyzed for NKp46 expression and for cytotoxicity against 0.221 target cells. A reduction in the NKp46 expression was observed in NK clones derived from all of the patients as compared with the healthy sister. All 30 NK clones (100%) derived from patient A did not express the NKp46 protein; 19 (39%) of 49 clones and 56 (80%) of 70 clones derived from patient B and patient C, respectively, were also NKp46$^-$ (Table 4). The absence of the NKp46 receptor on these NK clones was correlated with poor cytolytic activity against 0.221 cells (Table 4). NKp46$^-$ clones were not observed in the healthy sister (Table 4). On the other hand, 29 (61%) of 49 NK clones derived from patient B, 14 (20%) of 70 from patient C, and 30 (100%) of 30 from the healthy sister were NKp46$^+$ (Table 4). The level of the NKp46 expression was similar in all positive clones (Table 4). Accordingly, the NKp46$^+$ NK clones displayed efficient cytotoxic activity against 0.221 target cells (Table 4). Efficient killing of other cells types such as EBV-A, EBV-B, EBV-C, 293T, or RPMI 8866 was also observed when assayed against the NKp46$^+$ clones.

Activated NK Clones Derived from the TAP2-Deficient Patients Express Unusually High Levels of CEACAM1− and Class I MHC-Recognizing Receptors The killing of targets by NK cells derived from the TAP2-deficient patients can be reduced by the diminished NKp46 expression. However, 61% and 20% of the clones in patients B and C, respectively, still expressed NKp46 (Table 4). The present inventors hypothesized the existence of a class I MHC-independent inhibitory mechanism in their patients that controls NK autoreactivity and examined whether CEACAM1 interactions were involved in controlling the killing activity of activated NK cells in TAP2-deficient patients.

Peripheral blood lymphocytes (PBLs) were isolated from all 3 patients and the healthy sister and analyzed by multi-staining for the expression of the CD3, CD16, CD56, and CEACAM1. All patients had normal values of lymphocytes in their peripheral blood and a normal lymphocyte distribution, including T, NK, and NKT cells. Thus, the low levels of class I MHC proteins (Tables 2, 3) were probably sufficient to select for the development of normal members of lymphocytes. PBLs from all 4 donors were also tested for the expression of the CEACAM1 protein. Little or no expression of the CEACAM1 protein was observed among all fresh PBLs.

Activated NK clones were generated from the 3 patients and from the healthy sister. Sixty NK clones from each individual were assessed for CEACAM1 expression by using the 5F4 mAb. The NK clones from each individual were sub grouped according to the CEACAM1 expression level (negative, low, or high). Low levels of CEACAM1 expression (MFI around 8) had already been observed on NK clones and proved sufficient to confer protection.[15,18] The high expression level of CEACAM1 (MFI around 30) observed on the surface of NK clones had not been observed before. 53 (88%) of 60 NK clones obtained from the healthy sister were negative for CEACAM1 (Table 5). In contrast, virtually all of the NK clones (98%) obtained from patient A expressed the CEACAM1 protein in unusually high levels. Of the 60 NK clones obtained from patient B, 43 (71%) expressed the CEACAM1 protein in low or high levels (43% and 28%, respectively; Table 5) whereas 44 (73%) of 60 NK cells derived from patient C expressed CEACAM1 in low or high levels (23% and 50%, respectively; Table 5).

In addition, all of the NK clones were stained for the presence of CD16, KIR2DL1, KIR2DL2, CD94, or LIR1. In each individual, the total NK clones were further sub classified in each CEACAM1 subgroup according to the staining intensity of each receptor (negative, dim, and bright), and the mean MFI±SD was calculated accordingly. The overall percentages of NK clones from each individual expressing KIR2DL1, KIR2DL2, and LIR1 was compared. KIR2DL1 was expressed on 62%, 77%, and 72% of the NK clones obtained from patients A, B, and C, respectively, compared with only 25% of the NK clones from the healthy sister (Table 5). KIR2DL2 was expressed on 65%, 65%, and 85% of the NK clones obtained from patients A, B, and C, respectively, compared with only 35% of the NK clones from the healthy sister (Table 5). Finally, the LIR1 was expressed on 67%, 68%, and 60% of the NK clones obtained from patients A, B, and C, respectively, compared with only 15% of the NK clones from the healthy sister (Table 5). Expression of all inhibitory NK receptors tested was up-regulated on the NK cells derived from the patients. The increase in the percentage of NK clones derived from the patients that express class I MHC-recognizing inhibitory receptors is statistically significant when compared with the healthy sister: KIR2DL1 (P=0.01), KIR2DL2 (P=0.04), and LIR1 (P=0.02). Further analysis reveals that the receptor expression level is also increased among NK clones obtained from the patients as compared with those obtained from the healthy sister. Bright expression of KIR2DL, was observed on 24 of 60, 32 of 60, and 33 of 60 NK clones obtained from patients A, B, and C, respectively, but not on any of the 60 NK clones obtained from the healthy sister (P=0.003) (Table 5). Similarly, bright expression of KIR2DL2 was observed on 21 of 60, 34 of 60, and 37 of 60 NK clones obtained from patients A, B, and C, respectively, as opposed to only 16 of 60 obtained from the healthy sister (P=0.06) (Table 5). Patients of in the present section express the Cw7 protein, which is recognized by KIR2DL2.[30] A statistically significant bright expression of KIR2DL1 but not KIR2DL2 was observed in the patients' NK clones, suggesting that the expression level of the various NK receptors is somehow shaped by the appropriate MHC proteins (Table 5). Thus, the low levels of class I MHC proteins in the patients have resulted in an impaired repertoire of inhibitory receptors, manifested not only in the increased percentages of positive clones but also in the higher expression levels.

Expression of the CD94 receptor was observed on 95%, 97%, and 92% of the NK clones obtained from patients A, B, and C, respectively, and on 100% of the NK clones from the healthy sister (P=0.66) (Table 5). The expression of CEACAM1 is confined mainly to the CD16$^-$ subset of NK cells.[15,18] Expression of CD16 was observed on 83%, 98%, and 87% of the NK clones obtained from patients A, B, and C, respectively, and on 90% of the NK clones from the healthy sister (P=0.29) (Table 5). CEACAM1 expression on NK clones derived from the healthy sister was restricted mainly to the CD16$^-$ cells (6 of 7 CEACAM1$^{dim}$ NK clones; Table 5). In contrast, 50 of 59, 42 of 43, and 37 of 44 NK clones derived from patients A, B, and C, respectively, expressed both CD16 and CEACAM1 (P=0.007) (Table 5). There was observed expression of CEACAM1 on both CD16⁻ and CD16⁺ NK clones derived from the patients (Table 5).

Figure 17:
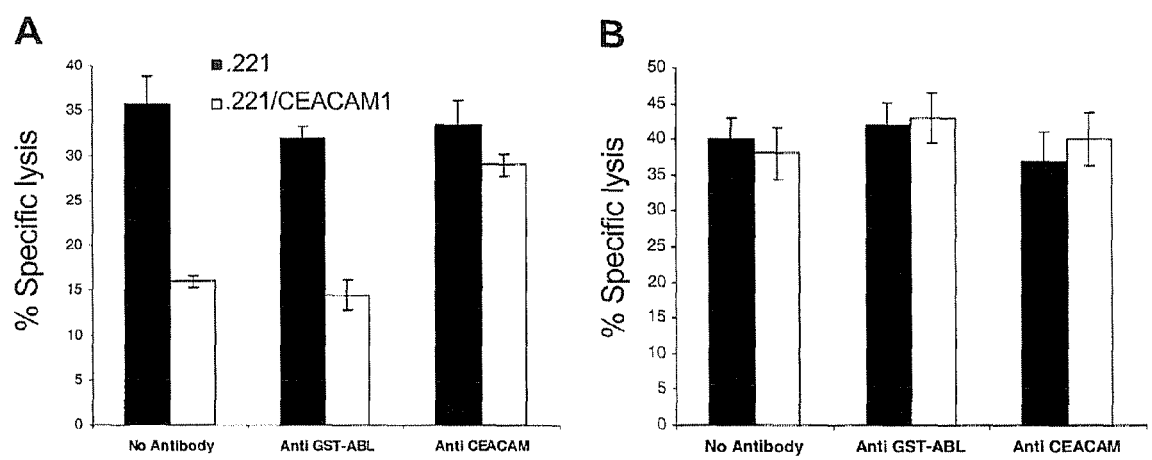
FIG. 17. Inhibition of NK-mediated killing by homophilic CEACAM1 interactions. Killing of 0.221 and 0.221/CEACAM1 cells, incubated with or without polyclonal anti-CEACAM antibodies, by a representative CEACAM1+ NK clone (panel A) or by a CEACAM1− NK clone (panel B). As control, anti-glutathion S-transferase (GST)-ABL polyclonal antibodies were used. The effector-to-target (E/T) ratio was 2:1. All antibodies used were in the form of F(ab')$_2$. Figures show the average of 3 independent experiments. The data represent means of the percentage of killing±SDs.

3.5 CEACAM1 Interactions Protect Autologous PHA-Induced T-Cell Blasts from NK Cell-Mediated Killing The functional significance of CEACAM1 expression was assayed with clones capable of killing 0.221 cells (Table 4). As the CEACAM1 protein binds via homophilic interactions to other CEACAM1 proteins,[15,18,31,32] the various NK clones were tested for killing against 0.221 cells expressing the CEACAM1 protein.[15,18] Inhibition of killing was observed when CEACAM1⁺ NK clones were used (representative clone in FIG. 17A). This inhibition was the result of CEACAM1 interactions, as lysis was restored when anti-CEACAM F(ab')$_2$ antibodies were included in the assay (FIG. 17). No inhibition was observed when CEACAM1⁻ NK clones were used (FIG. 17B).

It was nest determined whether normal, nonvirally infected, PHA-induced T-cell blasts will be killed by the patients' NK cells. In agreement with reports demonstrating that activated T cells express the CEACAM1 protein,[23,29] expression of CEACAM1 was observed on all PHA-induced T-cell blasts derived from all patients (FIG. 18A). The expression level of the CEACAM1 protein on the PHA-induced T-cell blasts derived from the TAP2-deficient patients was approximately 5-fold higher as compared with the PHA-induced T-cell blasts obtained from the healthy sister (FIG. 18A). Low levels of class I MHC protein expression were observed on PHA-induced T-cell blasts derived from patients compared with the healthy sister (FIG. 18A). Staining of the various PHA-induced T-cell blasts for the presence of ligands for the NKp46, NKp44, and NKp30 receptors with the use of immunoglobulin-fusion proteins was negative (FIG. 18B). NKp46-Ig, NKp30-Ig, and NKp44-Ig did, however, recognize tumor targets such as LnCap (FIG. 18B) or other cell lines.[7,8] The cellular ligands for these receptors may be either not expressed or may be expressed in low levels on the surface of the PHA-induced T-cell blasts. The expression of other lysis ligands such as MICA is present on the PHA-induced T-cell blasts.[33]

CEACAM1⁺ NK clones from each patient were assayed for lysis against the various PHA-induced T-cell blasts. All CEACAM1⁻ NK clones and bulk cultures derived from the healthy sister killed the TAP2-deficient PHA-induced T-cell blasts (see, e.g., "NK Sister CEACAM1⁻" in FIG. 18C). Similar results were obtained with bulk NK cells and clones obtained from other healthy donor. None of the tested NK clones or bulk cultures derived from the patients killed their autologous PHA-induced T-cell blasts (see, e.g., NK A, NK B, and NK C in FIG. 18C). Blocking antibodies were included in the assay to test whether the lack of self-killing is because of CEACAM1- or class I MHC-mediated inhibition. The PHA-induced T-cell blasts were preincubated with or without the anti-CEACAM antibodies, the control antiubiquitin antibodies, HP-1F7 mAb, or the control 12E7 mAb. A significant enhancement of the killing activity of the patients' NK clones (A, B, and C) was observed when the F(ab')$_2$ fragments of anti-CEACAM antibodies were included in the assay, either alone or in combination with the anti-class I MHC mAb HP-1F7 (FIG. 18C). Similar results were obtained regardless of whether the NK clones tested expressed the NKp46 receptor. No effect was observed when the F(ab')$_2$ fragments of the anti-class I MHC mAb HP-1F7 were included (FIG. 18C). The low expression level of class I MHC proteins was not enough to confer protection. Killing was not restored when the control F(ab')$_2$ fragments of either the polyclonal antiubiquitin antibodies or the 12E7 mAb were used (FIG. 18C). These results indicate that self-attack of the autologous PHA-induced T-cell blasts by NK clones derived from the patients is prevented by the homophilic CEACAM1 inhibitory interactions.

Autologous NK clones negative for CEACAM1 expression were unable to kill the autologous PHA-induced T-cell blasts (see, e.g., patient C's CEACAM1⁻ NK cells, which express NKp46; FIG. 18C). This property is unique to NK cells derived from the patients, as CEACAM1⁻ NK cells from the healthy sibling efficiently attacked self-cells following MHC class I blocking (FIG. 18C-D).

The NK clones and bulk cultures obtained from patients A, B, and C and the healthy sister were next tested in killing assays against PHA-induced T-cell blasts derived from the healthy sister. The various cells were treated as described in the text discussion of FIG. 18C. CEACAM1⁻ NK clones derived from the healthy sister were unable to kill the autologous PHA-induced T-cell blasts. The inhibition was the result of class I MHC interactions, as the F(ab')$_2$ fragments of HP-1F7 mAb included in the assay, either alone or in combination with the F(ab')$_2$ fragments of anti-CEACAM antibodies, abolished this inhibition (FIG. 18D). When CEACAM1⁺ NK clones derived from the TAP2-deficient patients were used, lysis of the sister's PHA-induced T-cell blasts could be completely restored only when the F(ab')$_2$ fragments of both the HP-1F7 and anti-CEACAM antibodies were used (FIG. 18D). Partial restoration of killing was observed when either the CEACAM1 or the class I MHC interactions were disrupted, indicating that both inhibitory mechanisms prevent the killing of normal PHA-induced T-cell blasts. Similar results were obtained when CEACAM1⁺ NK clones derived from the healthy sister were used.

CEACAM1 protein is up-regulated on NK cells derived from some melanoma patients and from decidua.[15,18] The vast majority of activated NK cells derived from TAP2-deficient patients express the CEACAM1 protein in high levels, the expression of the CEACAM1 protein is restricted to patient-derived NK cells with the ability to kill self-cells, and the CEACAM1 protein is capable of inhibiting NK killing. NK cells derived from TAP2-deficient patients have developed or acquired a unique mechanism to control the killing of self-cells by using the CEACAM1 interactions.

TABLE 2

Expression of MHC proteins on NK clones

| Antibody | Patient A | Patient B | Patient C | Healthy sister |
| --- | --- | --- | --- | --- |
| Secondary F(ab')$_2$ background | 3.2 ± 0.7 | 2.2 ± 0.3 | 2.8 ± 0.4 | 3.4 ± 0.8 |
| W6/32 F(ab')$_2$ | 36.7 ± 8.2 | 23 ± 6.5 | 30.7 ± 8.0 | 629 ± 183 |
| BBM-1 F(ab')$_2$ | 7.7 ± 2.5 | 5.3 ± 1.7 | 7.1 ± 1.6 | 130 ± 30 |
| MHC class II F(ab')$_2$ | 33.1 ± 3.6 | 54.3 ± 9.6 | 54.6 ± 7.7 | 94.7 ± 9.1 |

Forty NK clones were isolated from each of the 3 patients and from the healthy sister. Clones were stained by various mAbs as indicated and analyzed by FACS. All antibodies used were in the form of F(ab')$_2$ fragments. Background was the secondary mAb in the form of F(ab')$_2$. Data are presented as the median fluorescence intensity (MFI) of 40 clones±standard deviation (SD). All 160 clones were stained at the same time.

TABLE 3

Expression of MHC proteins on EBV-transformed B-cell lines

| Cells | Background | W6/32 | BBM-1 | HLA-DQ | HLA-DR | HLA-A3 |
|---|---|---|---|---|---|---|
| EBV-A | 2.5 ± 0.5 | 122.5 ± 4.9 | 12.5 ± 2.1 | 22.5 ± 2.1 | 91.5 ± 23.3 | 2.5 ± 0.5 |
| EBV-B | 3 ± 0.5 | 106.5 ± 2.1 | 8 ± 4.2 | 24 ± 2.8 | 99.5 ± 14.8 | 2.8 ± 0.6 |
| EBV-C | 2 ± 0.4 | 76 ± 1.4 | 7.35 ± 2.9 | 29.5 ± 4.9 | 114.5 ± 17.7 | 3.0 ± 0.5 |

EBV-transformed B-cell lines were made from the indicated individuals. Cell lines were stained by various mAbs in the form of F(ab')$_2$ as indicated and analyzed by FACS. Background was the secondary mAb in the form of F(ab')$_2$. Data are presented as the average MFI of 3 independent experiments±SD.

TABLE 4

Impaired expression and function of NKp46 on activated NK clones

| | Patient A | | Patient B | | Patient C | | Healthy sister | |
|---|---|---|---|---|---|---|---|---|
| | .221 cells | | .221 cells | | .221 cells | | .221 cells | |
| | NKp46, MFI | killed, % | NKp46, MFI | killed, % | NKp46, MFI | killed, % | NKp46, MFI | killed, % |
| NKp46⁻ | 2.2 ± 0.9 (30/30) | 6.7 ± 2.9 (30/30) | 1.7 ± 0.6 (19/49) | 7.2 ± 3.7 (19/49) | 1.8 ± 0.7 (56/70) | 4.8 ± 2.1 (56/70) | N/O | N/O |
| NKp46⁺ | N/O | N/O | 16.5 ± 6.3 (29/49) | 25 ± 5.9 (29/49) | 13.5 ± 6 (14/70) | 20.9 ± 6 (14/70) | 16.9 ± 5 (40/40) | 26.5 ± 5.3 (40/40) |

Activated NK clones were prepared from each individual as indicated. Clones were stained for NKp46 expression by means of the 461-G1 mAb in the form of F(ab')$_2$ and concomitantly tested for cytotoxic activity against 0.221 cells. NKp46 expression is presented as the mean MFI of different NK clones±SD. Cytotoxic activity is presented as the mean percentage of 0.221 cells killed by NK clones. The data represent mean percentage of cells killed±SD. The number of NK clones included in the analysis out of total NK clones tested in each group are indicated in parentheses.

N/O Indicates not Observed.

TABLE 5

Analysis of various NK receptors in accordance with CEACAMI expression

| CEACAM1 oppression and receptor staining intensity | Background | CD16 | KIR2DL1 | KIR2DL2 | CD94 | LIR1 |
|---|---|---|---|---|---|---|
| Patient A | | | | | | |
| Negative CEACMA1 expression[a] | | | | | | |
| Receptor staining intensity | | | | | | |
| Negative | 2 ± 0.5 | N/O | 2.2 (1/1) | 2.5 (1/1) | N/O | 3 (1/1) |
| Dim | 2 ± 0.5 | 28 (1/1) | N/O | N/O | 48 (1/1) | N/O |
| Bright | 2 ± 0.5 | N/O | N/O | N/O | N/O | N/O |
| Low CEACMA1 expression[b] | | | | | | |
| Receptor staining intensity | | | | | | |
| Negative | 2 ± 0.5 | N/O | N/O | N/O | N/O | N/O |
| Dim | 2 ± 0.5 | N/O | N/O | N/O | N/O | N/O |
| Bright | 2 ± 0.5 | N/O | N/O | N/O | N/O | N/O |
| High CEACMA1 expression[c] | | | | | | |
| Receptor staining intensity | | | | | | |
| Negative | 2 ± 0.5 | 5 ± 1 (9/59) | 3 ± 2 (22/59) | 4 ± 1 (20/59) | 4 ± 0 (3/59) | 3 ± 1 (19/59) |
| Dim | 2 ± 0.5 | 15 ± 4 (50/59) | 21 ± 5 (18/59) | 18 ± 12 (18/59) | 19 ± 5 (26/59) | 18 ± 9 (33/59) |
| Bright | 2 ± 0.5 | NO | 151 ± 39 (21/59) | 198 ± 79 (21/59) | 98 ± 34 (30/59) | 104 ± 13 (7/59) |
| Sum of positive clones (%) | NA | 50/60 (83) | 37/60 (62) | 39/60 (65) | 57/60 (95) | 40/60 (67) |
| Patient B | | | | | | |
| Negative CEACMA1 expression[d] | | | | | | |
| Receptor staining intensity | | | | | | |
| Negative | 2 ± 0.5 | N/O | 3 ± 0 (2/17) | 2 ± 0.5 (7/17) | N/O | 4 ± 1 (6/17) |
| Dim | 2 ± 0.5 | 15 ± 5 (4/17) | 30 ± 16 (6/17) | 9 ± 2 (2/17) | 24 ± 10 (7/17) | 15 ± 3 (9/17) |
| Bright | 2 ± 0.5 | 161 ± 70 (13/17) | 122 ± 37 (9/17) | 222 ± 77 (8/17) | 95 ± 23 (10/17) | 88 ± 15 (2/17) |

TABLE 5-continued

Analysis of various NK receptors in accordance with CEACAMI expression

| CEACAM1 oppression and receptor staining intensity | Background | CD16 | KIR2DL1 | KIR2DL2 | CD94 | LIR1 |
|---|---|---|---|---|---|---|
| Low CEACMA1 expression[e] Receptor staining intensity | | | | | | |
| Negative | 2 ± 0.5 | N/O | 2 ± 1 (9/26) | 3 ± 1 (11/26) | 4 (1/26) | 3 ± 1 (8/26) |
| Dim | 2 ± 0.5 | 20 ± 8 (12/26) | 29 ± 2 (4/26) | 12 ± 3 (3/26) | 18 ± 6 (9/26) | 11 ± 3 (14/26) |
| Bright | 2 ± 0.5 | 142 ± 70 (14/26) | 149 ± 2 (13/26) | 274 ± 140 (12/26) | 90 ± 21 (16/26) | 100 (4/26) |
| High CEACMA1 expression[f] Receptor staining intensity | | | | | | |
| Negative | 2 ± 0.5 | 3 (1/17) | 2 ± 1 (3/17) | 2 ± 0 (3/17) | 4 (1/17) | 4 ± 1 (5/17) |
| Dim | 2 ± 0.5 | 38 ± 16 (6/17) | 31 ± 15 (4/17) | N/O | 28 ± 13 (8/17) | 10 ± 2 (9/17) |
| Bright | 2 ± 0.5 | 115 ± 47 (10/17) | 168 ± 55 (10/17) | 209 ± 54 (14/17) | 82 ± 15 (8/17) | 93 ± 25 (3/17) |
| Sum of positive clones (%) | NA | 59/60 (98) | 46/60 (77) | 39/60 (65) | 58/60 (97) | 41/60 (68) |
| Patient C Negative CEACMA1 expression[g] Receptor staining intensity | | | | | | |
| Negative | 2 ± 0.5 | 2 (1/16) | 3 ± 1 (10/16) | 3 ± 11 (3/16) | 3 ± 1 (2/16) | 3 ± 1 (7/16) |
| Dim | 2 ± 0.5 | 16 ± 10 (13/16) | 43 ± 13 (3/16) | 73 ± 22 (3/16) | 35 ± 9 (14/16) | 9 ± 3 (9/16) |
| Bright | 2 ± 0.5 | 72 ± 4 (2/16) | 149 ± 73 (3/16) | 184 ± 65 (10/16) | N/O | N/O |
| Low CEACMA1 expression[h] Receptor staining intensity | | | | | | |
| Negative | 2 ± 0.5 | 4 ± 0 (2/14) | 5 ± 0.4 (3/14) | 4 ± 1 (3/14) | 3 ± 2 (1/14) | 3 ± 1 (6/14) |
| Dim | 2 ± 0.5 | 18 ± 9 (8/14) | 44 ± 16 (6/14) | 82 ± 9 (7/14) | 40 ± 13 (13/14) | 9 ± 2 (8/14) |
| Bright | 2 ± 0.5 | 88 ± 32 (4/14) | 146 ± 43 (5/14) | 321 ± 23 (4/14) | N/O | N/O |
| High CEACMA1 expression[i] Receptor staining intensity | | | | | | |
| Negative | 2 ± 0.5 | 4 ± 2 (5/30) | 4 ± 2 (4/30) | 4 ± 1 (3/30) | 3 ± 1 (3/30) | 3 ± 2 (11/30) |
| Dim | 2 ± 0.5 | 20 ± 11 (23/30) | 27 ± 10 (1/30) | 63 ± 18 (4/30) | 37 ± 15 (27/30) | 10 ± 2 (19/30) |
| Bright | 2 ± 0.5 | 88 ± 10 (2/30) | 188 ± 81 (25/30) | 267 ± 102 (23/30) | N/O | N/O |
| Sum of positive clones (%) | NA | 52/60 (87) | 43/60 (72) | 51/60 (85) | 55/60 (92) | 36/60 (60) |
| Healthy sister Negative CEACMA1 expression[j] Receptor staining intensity | | | | | | |
| Negative | 2 ± 0.5 | N/O | 3 ± 2 (38/53) | 3 ± 1 (33/53) | N/O | 3 ± 1 (46/53) |
| Dim | 2 ± 0.5 | 45 ± 6 (53/53) | 50 ± 23 (15/53) | 27 ± 14 (5/53) | 26 ± 12 (36/53) | 10 ± 3 (7/53) |
| Bright | 2 ± 0.5 | N/O | N/O | 208 ± 97 (15/53) | 80 ± 25 (17/53) | N/O |
| Low CEACMA1 expression[k] Receptor staining intensity | | | | | | |
| Negative | 2 ± 0.5 | 4 ± 1 (6/7) | 3 ± 2 (7/7) | 5 ± 2 (6/7) | N/O | 3 ± 11 (5/7) |
| Dim | 2 ± 0.5 | 40 (1/7) | N/O | N/O | 16 ± 3 (4/7) | 10 ± 2 (2/7) |
| Bright | 2 ± 0.5 | N/O | N/O | 108 (1/7) | 71 ± 8 (3/7) | N/O |
| High CEACMA1 expression[b] Receptor staining intensity | | | | | | |
| Negative | 2 ± 0.5 | N/O | N/O | N/O | N/O | N/O |
| Dim | 2 ± 0.5 | N/O | N/O | N/O | N/O | N/O |
| Bright | 2 ± 0.5 | N/O | N/O | N/O | N/O | N/O |
| Sum of positive clones (%) | NA | 54/60 (90) | 15/60 (25) | 21/60 (35) | 60/60 (100) | 9/60 (15) |

NK clones were prepared from the indicated individuals. Sixty NK clones from each donor were analyzed for CEACAM1 expression and were classified into 3 groups according to CEACAM1 intensity (negative, low, and high). All NK clones in each CEACAM1 subgroup were further stained for various NK receptors and were subdivided according to intensity of the expression of the particular receptor (negative, dim, and bright). The mean MFI of the various groups ± SD is presented, with the number of the relevant NK clones of the total number of NK clones in each CEACAM1 subgroup indicated in parentheses. The sum of all positive (dim and bright) clones in each subgroup is indicated for each patient, with the percentage indicated in parentheses (total number of clones for each patient is 60). All staining was performed with antibodies in the form of F(ab')2 and at the same time. Data are presented in all groups as means of MFI ± SD.
N/O indicates not observed; and NA, not available.
[a]MFI = 3 (1/60 = 2%).
[b]MFI = NO.
[c]MFI = 32 ± 13 (59/60 = 98%).
[d]MFI = 2 ± 0.6 (17/60 = 29%).
[e]MFI = 8 ± 2 (26/60 = 43%).
[f]MFI = 25 ± 7 (17/60 = 28%).
[g]MFI = 2 ± 0.6 (16/60 = 27%).
[h]MFI = 8 ± 2 (14/60 = 23%).
[i]MFI = 31 ± 13 (30/60 = 50%).
[j]MFI = 3 ± 1 (53/60 = 88%).
[k]MFI = 8 ± 1 (7/60 = 12%).

Example 4

CD66a Interactions Between Human Melanoma and NK Cells: a Novel, Class I MHC-Independent Inhibitory Mechanism of Cytotoxicity NK cells are able to kill virus-infected and tumor cells via a panel of lysis receptors. Cells expressing class I MHC proteins are protected from lysis primarily due to the interactions of several families of NK receptors with both classical and nonclassical class I MHC proteins. The present inventors show that a class I MHC-deficient melanoma cell line (1106mel) is stained with several Ig-fused lysis receptors, suggesting the expression of the appropriate lysis ligands. This melanoma line was not killed by CD16-negative NK clones. The lack of killing is shown to be the result of homotypic CD66a interactions between the melanoma line and the NK cells. Furthermore, 721.221 cells expressing the CD66a protein were protected from lysis by YTS cells and by NK cells expressing the CD66a protein. Redirected lysis experiments demonstrated that the strength of the inhibitory effect is correlated with the levels of CD66a expression. Finally, the expression of CD66a protein was observed on NK cells derived from patients with malignant melanoma. These findings suggest the existence of a novel class I MHC-independent inhibitory mechanism of human NK cell cytotoxicity. This may be a mechanism that is used by some of the class I MHC-negative melanoma cells to evade attack by CD66a-positive NK cells. (Gal Markel et al., *CD66a Interactions Between Human Melanoma and NK Cells: A Novel Class I MHC-Independent Inhibitory Mechanism of Cytotoxicity*, The Journal of Immunology, 2002, 168: 2803-2810. This reference is herein incorporated by reference.)

Materials and Methods

Cells and Mab

The cell lines used in this section are the class I MHC-negative human cell line 721.221, the YTS NK tumor line, and various MHC class I-negative and -positive human melanoma cell lines. NK cells were isolated from PBL using the human NK cell isolation kit and the autoMACS instrument (Miltenyi Biotec, Auburn, Calif.). For the enrichment of CD66a-positive NK cells, isolated NK cells were further purified by depletion of CD16-positive NK cells using anti-CD16 mAb 3G8 and the autoMACS instrument. NK cells were grown in culture as described. The production and specificity of anti-NKp44 and NKp46 sera were as described. The mAbs used in this section were mAb W632, directed against class I MHC molecules, the mAb anti-CD66 a,b,c,e Kat4c (purchased from DAKO, Carpenteria, Calif.), anti-CD66a mAb 5F4, and the rabbit polyclonal anti-CD66a,c,e Abs (purchased from DAKO). The anti-CD99 mAb 12E7, used as a control, was from the Hospital de L'Archet, Nice, France. The anti-CD56 mAb (BD PharMingen, San Diego, Calif.) was also used as control.

Cytotoxicity Assay and Ig Fusion Proteins

The cytotoxic activity of YTS and NK cells against the various targets was assayed in 5-h $^{35}$S release assays as described. In experiments in which mAb were included, the final mAb concentration was 10 μg/ml, or 40 μl/ml in cases where rabbit polyclonal Abs were used. Redirected lysis experiments were performed as described. The production of CD99-Ig, CD16-Ig, NKp30-Ig, NKp44-Ig, and NKp46-Ig fusion proteins by COS-7 cells and purification on a protein G column were as described.

Quadruple Staining

For quadruple staining, the following fluorochrome-conjugated mAbs were used: FITC-conjugated anti-CD66 Kat4c mAb (DAKO), PE-conjugated anti-CD56 mAb (BD PharMingen), and CyChrome-conjugated anti-CD3 (BD PharMingen). As the fourth color, biotinylated anti-CD16 mAb (Serotec, Oxford, U.K.) was used, followed by streptavidin-Cy5 (Jackson ImmunoResearch Laboratories, West Grove, Pa.) as a second reagent. To block nonspecific binding, cells were first incubated for 1 h on ice with 25% human serum and then incubated with the various Abs.

Generation of YTS and 721.221 Cells Expressing CD66a

The primers used for the amplification of CD66a cDNA needed for the transfection of 721.221 cells were as follows: 5' primer, CCCAAGCTTGGGGCCGCCAC-CATGGGGCACCTCTCAGCC (including the HindIII restriction site) (SEQ ID NO 10), and 3' primer, GGAATTC-CTTACTGCTTTTTTACTTCTGAATA (including the EcoRI restriction site) (SEQ ID NO 9). cDNA was cloned into the pcDNA3 vector (Invitrogen, San Diego, Calif.) and transfected into 721.221 cells as described. For transfection into YTS cells, CD66a cDNA was amplified by PCR using the 5' primer GGAATTCCGCCGCCACCATGGGGCAC-CTCTCAGCC (including the EcoRI restriction site) (SEQ ID NO 27) and the 3' primer GCGTCGACTTACTGCTTTTT-TACTTCTGAATA (including the SalI restriction site) (SEQ ID NO 28). For amplification of the CD66aTrunc cDNA, the same 5' primer was used, with the 3' primer GCGTCGA-CATCTTGTTAGGTGGGTCATT (SEQ ID NO 29). Amplified fragments were cloned into the pBABE retroviral vector and transfected into YTS cells as described.

Expression of Various Lysis Ligands, CD66a, and Class I MHC Proteins on Human Melanoma Cells The roles of NKp30, NKp44, NKp46, and CD16 receptors in NK recognition of various melanoma cells deficient in class I MHC expression (except from LB33melA1, used as a control) were studied by production of fusion proteins in which the extracellular domains of NKp30 NKp44, NKp46, and CD16 were fused to the Fc portion of Ig. cDNA encoding the extracellular domains of CD99 fused to the human IgG1 DNA was used as a control. The Ig fusion proteins were incubated with the various melanoma cells and analyzed for binding by indirect immunostaining as previously described (15). In general, the highest staining of the melanoma cells was observed with the NKp30-Ig and NKp44-Ig fusion proteins (Table 6). Little staining of all Ig fusion proteins was observed with LB33melA1 cells, a cell line that is hardly killed by NK cells. All other cell lines that can be killed by NK cells were stained to various degrees with the Ig fusion proteins (Table 6).

IL-2-activated CD16-negative NK cells inefficiently kill 1106mel cells. Surprisingly, 1106mel cells probably express the ligands for all the NK lysis receptors tested, including CD16, NKp30, NKp44; and NKp46 (Table 6). Thus, killing of 1106mel cells was expected to occur even when CD16-negative NK cells, which express the NKp44 and NKp46 receptors, were used. The present inventors hypothesized the existence of a class I-independent mechanism of inhibition of NK cell cytotoxicity that controls the lysis of 1106mel cells. The present inventors hypothesized that this inhibitory mechanism should include a protein that is expressed mainly on the surface of IL-2-activated CD16-negative NK cell and is expected to deliver an inhibitory signal via the ITIM. The CD66a (carcinoembryonic Ag CAM1) protein is expressed primarily on CD16-negative NK cells, it contains ITIM sequences, and it can bind in a homotypic/heterotypic manner to various CD66 proteins. The inhibitory effect of the CD66a protein on human NK cell cytotoxicity was investigated by the present inventors.

The present inventors tested whether the expression of CD66a molecule can be detected on the surface of various melanoma cell lines and NK cells. Remarkably, all seven class I MHC-negative melanoma cell lines tested expressed the CD66a protein at moderate or high levels (Table 7). No expression of MHC class I protein (detected with the W632 mAb) was observed among these cell lines, except from the LB33melB1 cell line that expresses the HLA-A24 protein only. In contrast, 40% of the class I MHC-positive melanoma lines tested showed little or no staining for the CD66a protein (Table 7).

Figure 19:
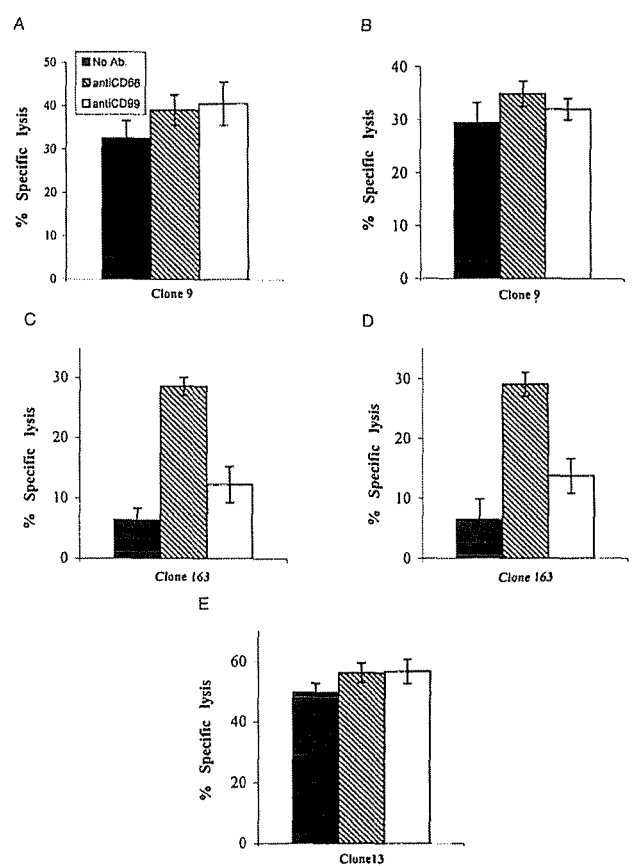
FIG. 19. Killing of melanoma lines by NK clones. Lysis of 1106mel cells (A-D) and 1259mel cells (E) by CD16$^+$ CD66a$^-$ NK clone (A and B) or CD16$^-$CD66a$^+$ NK clone (C-E) was performed as described in Materials and Methods of this section. The anti-CD99 mAb (12E7) and anti-CD66a polyclonal Abs were incubated with the target cells (A and C) or with the effector cells (B, D, and E). The E:T cell ratio was 3:1.

Recognition of CD66a Expressed on 1106mel by CD66a on CD16-Negative NK Cells Leads to Inhibition of Lysis The CD66a isoform is expressed on CD16-negative NK cells. Whether 1106mel cells would be protected from lysis by CD 16-negative NK cells expressing the CD66a protein was tested. For the generation of CD16-negative NK cells expressing CD66a, NK cells were first isolated from PBL of various healthy donors and then depleted from CD16-positive NK cells by using the anti-CD16 mAb 3G8 (as described in Materials and Methods of this section). Of 63 CD16-negative clones tested, 28 (45%) expressed the CD66a protein. In rare cases (2%) CD66a expression could be detected on the surface of CD16-positive NK clones (see FIG. 23). The percentage of CD16-negative, CD66a-positive NK cells can vary among different donors after activation. Various NK clones were then tested in killing assays against 1106mel cells. Efficient killing of 1106mel cells was observed with CD16$^+$ CD66a$^-$ NK clones (FIG. 19, A and B). The addition of anti-CD66 polyclonal Abs or the control 12E7 mAb (incubated with either effector or target cells) had little or no effect (FIG. 19↓, A and B). Similar results were obtained when CD16$^-$CD66a$^-$ NK clones were used (see FIG. 23↓). In agreement with other observations, little killing of 1106mel cells was observed when CD16$^-$CD66a$^+$ NK cells (for example, clone 163) were used (FIG. 19↓, C and D), whereas effective killing (32.4%) of the CD66-deficient NK-sensitive 721.221 cell line was observed. The low rate of 1106mel killing observed was the result of the inhibition mediated by the CD66 homotypic interactions, as lysis of 1106mel cells was restored when either the effector or the target cells were incubated with anti-CD66a polyclonal Abs (FIG. 19, C and D). The anti-CD66 polyclonal Abs specifically stained all cells that were positive for CD66a expression (NK clones, melanomas, and various transfectants) and did not stain cells that were negative for CD66a expression (for example, CD66a-negative NK clone). The controls, 12E7 mAb or polyclonal Abs from rabbit immunized with purified ubiquitin, had little or no effect (FIG. 19). Similar results were obtained when CD16$^+$CD66a$^+$ NK clones were used (see FIG. 23). Reversal of the CD66a-mediated inhibition was also observed even when the LB33melB1 cell line was used as a target. This cell line expressed the lowest levels of CD66a proteins among all seven class I-negative melanoma cells tested (Table 7). No inhibition of lysis by CD66a-positive NK cells was observed when these clones were incubated with the 1259mel melanoma line, a cell line that is efficiently killed by CD16-negative NK cells (FIG. 19E). The expression levels of the lysis ligands for CD16, NKp30, NKp44, and NKp46, detected by the Ig fusion proteins were similar to those of 1106mel cells. One possible explanation is that other lysis ligands for other lysis receptors exist on the surface of 1259mel cells, and the combined effect of all lysis receptors overcomes the CD66a-mediated inhibition.

Figure 20:
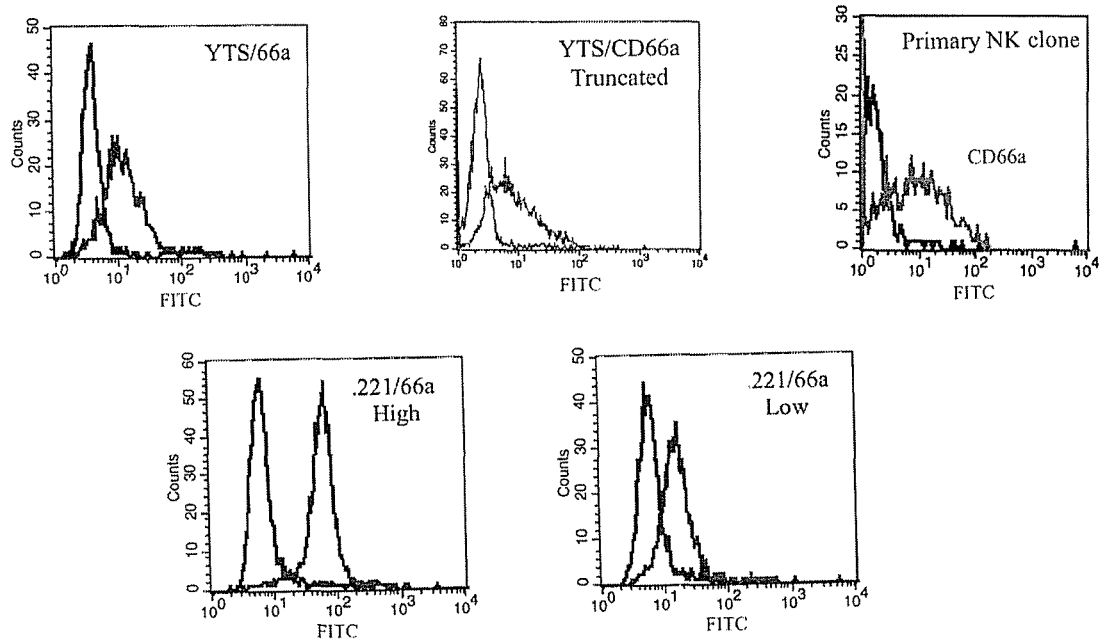
FIG. 20. Expression of CD66a on various cell types. Transfectants were generated as described in Materials and Methods of this section. Shown is CD66a staining of transfected 0.221 and YTS cells with the anti-CD66a mAb Kat4c (dark line) overlaid on the staining of the parental cells (0.221 and YTS) with the same mAb (light line). Staining of a representative NK clone by Kat4c (dark line) overlaid on the staining of the same NK clones with the control FITC-conjugated goat anti-mouse Abs (light line) is also shown. The figure shows one representative experiment of three performed.
Figure 21:
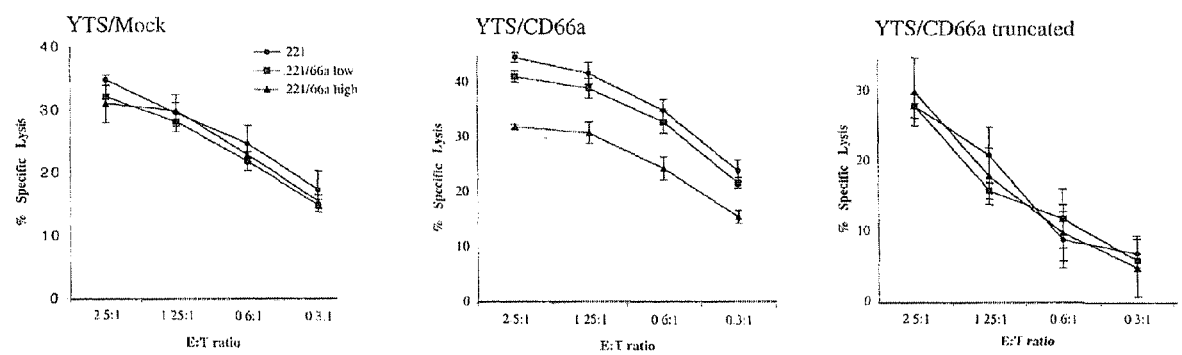
FIG. 21. Killing of various 721.221 transfectants by various YTS transfectants. Killing assays were performed as described in this section. The various YTS transfectants are indicated in each histogram. The figure shows one representative experiment of six performed.

The 721.221 Cells Expressing the CD66a Protein are Protected from Lysis by CD66a-Positive NK and YTS Cells To directly test the role of the CD66a protein in inhibition of NK cell cytotoxicity, 721.221 target cells and YTS effector cells (both deficient for CD66a expression; FIG. 20↓) were transfected with the CD66a cDNA. Several clones of 721.221 cells expressing various levels of CD66a protein (0.221/CD66a) were obtained. Two representative clones, expressing either low (0.221/CD66a$^{low}$) or high (0.221/CD66a$^{high}$) levels, are shown in FIG. 20. YTS cells expressing either CD66a (YTS/CD66a) or CD66a in which the cytoplasmic tail of the molecule was truncated not to include the ITIMs (YTS/CD66aTrunc) were also generated (FIG. 20). The expression level of the CD66a protein on YTS cells was similar to the physiological level of expression on an average primary NK clone (median fluorescence intensity (MFI) was >2-fold over the background; a representative clone is shown in FIG. 20). YTS transfectants expressing higher levels of CD66a protein could not be obtained. Transfectants were next tested in cytotoxicity assays. Inhibition of YTS/CD66a killing was observed when cells were incubated with 0.221/CD66a$^{high}$ in all E:T cell ratios tested (FIG. 21). The percentages of killing of other targets, including the parental 721.221 or the 0.221/CD66a$^{low}$ may be considered similar. Similar results were obtained with other YTS and 721.221 cells expressing similar levels of CD66a.

Lysis of all target cells tested against YTS cells transfected with the pBABE vector alone (YTS/MOCK) was similar. The CD66a inhibitory signal is probably transduced via the ITIM sequences, as no inhibition of lysis by YTS/CD66aTrunc was observed, even when these cells were incubated with 721.221/CD66a$^{high}$ cells (FIG. 21). The low level of CD66a expression on target cells (0.221/CD66a$^{low}$) did not confer protection (FIG. 21). The inhibition of lysis of 0.221/CD66a$^{high}$ cells by YTS/CD66a was the result of the CD66a interactions, as lysis was restored when anti-CD66 Abs were included in the assays (incubated either with the effector cells (FIG. 22A) or with the target cells. The controls, 12E7 mAb or rabbit polyclonal Abs directed against ubiquitin, had no effect.

Figure 22:
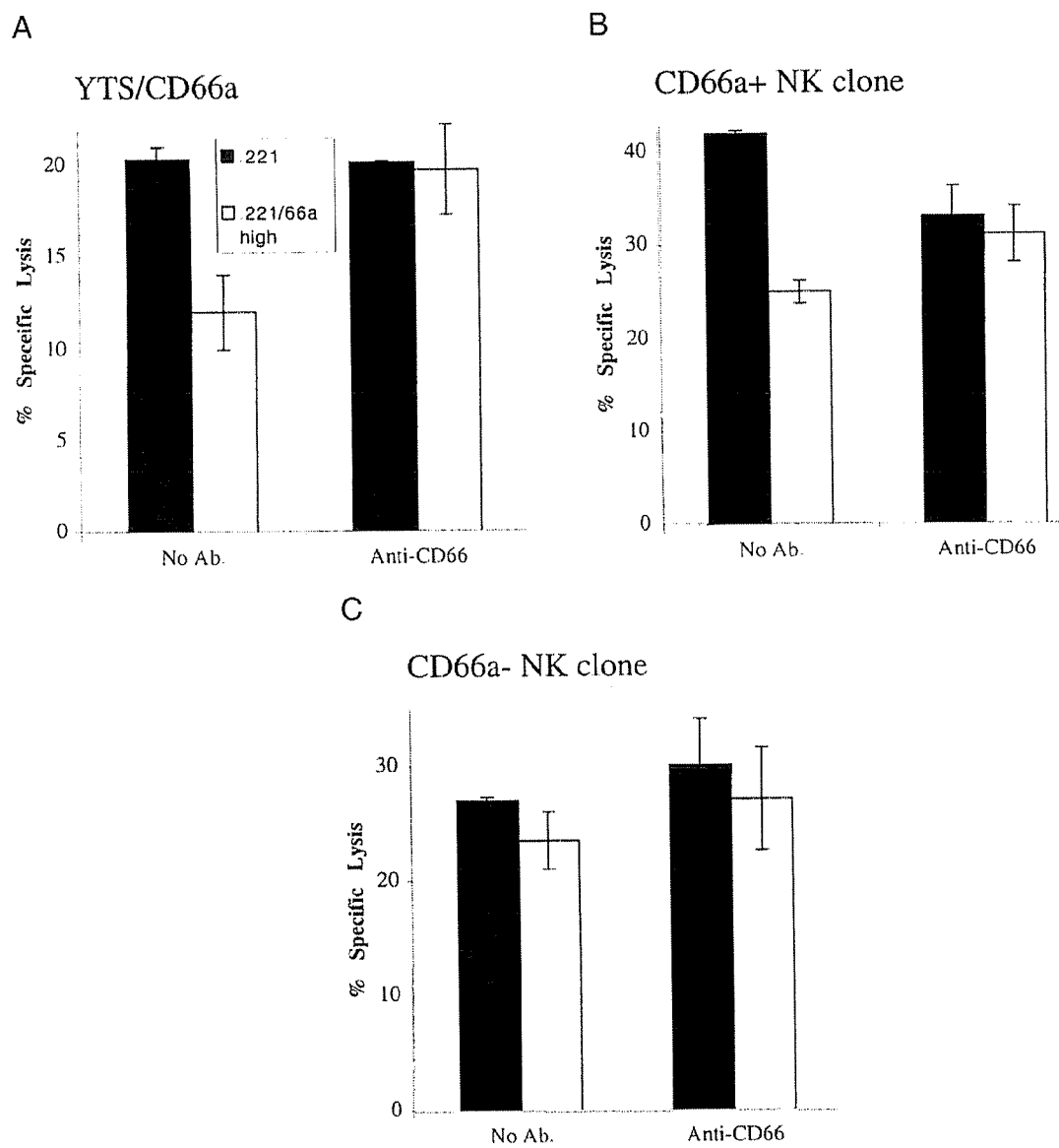
FIG. 22. Killing of 0.221/CD66a$^{high}$ cells by NK clones. Killing of target cells by YTS/CD66a (A), CD66-positive NK clone (B), and CD66-negative NK clone (C) incubated with or without anti-CD66a polyclonal Abs. The figure shows one representative experiment of five performed.

Lysis experiments were also performed with NK clones positive or negative for the expression of CD66a. NK clones were prepared as described above and tested against 0.221/CD66a$^{high}$ cells. CD66a-dependent inhibition of lysis of 0.221/CD66a$^{high}$ cells was observed when CD66a-positive NK cells were used (a representative clone is shown in FIG. 22B). No inhibition of lysis of 0.221/CD66a$^{high}$ cells was observed when CD66a-negative NK clones were used (representative clone is shown in FIG. 22C).

Levels of CD66a Expression on Both Effector and Target Cells are Important for Effective Inhibition One potential explanation for the moderate inhibition observed when 0.221/CD66a$^{high}$ cells were incubated either with YTS/CD66a or with CD66a$^+$ NK cells is the level of CD66a expression on both target and effector cells. Indeed, no inhibition of lysis was observed when 0.221/CD66a$^{low}$ cells were used (FIG. 21), moderate inhibition was observed when 0.221/CD66a$^{high}$ cells were used (FIG. 21), and strong inhibition of lysis was observed when 1106mel cells were used (FIG. 19, C and D). The 1106mel cell line expresses the CD66a protein at a level 10-fold higher than that of the 0.221/CD66a$^{high}$ transfectants (Table 7 and FIG. 20). 721.221 cells expressing the CD66a protein at a higher level than the transfectant presented in FIG. 20 could not be obtained. Thus, the level of CD66a expression on target cells is important for effective inhibition of both YTS and NK cells.

Figure 23:
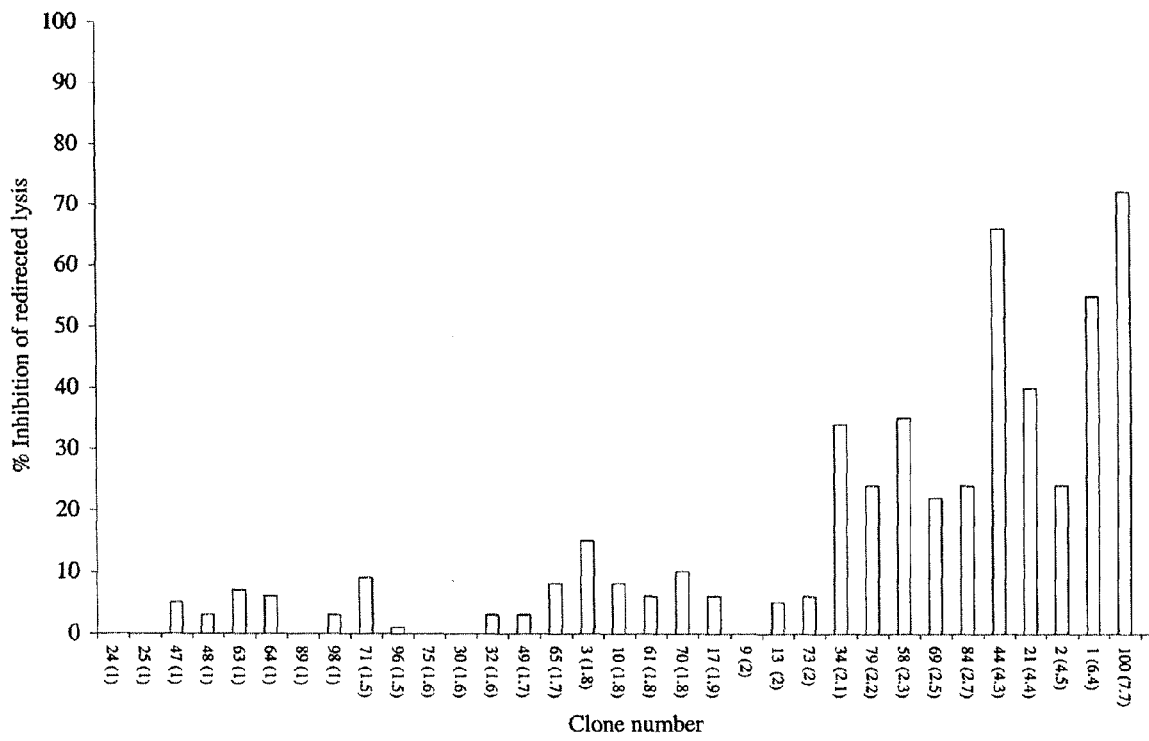
FIG. 23. The high level of CD66a expression on NK clones correlates with efficient inhibition of redirected lysis of P815 cells. The CD66a expression on NK clones was monitored by FACS. To correctly compare the level of CD66a expression among different NK clones, and because the background staining F(ab)'$_2$ of FITC-conjugated goat anti-mouse IgG Abs of each NK clone might be different, the level of CD66a expression in each clone was determined by dividing the MFI of the CD66a staining on a given clone with the MFI of the background staining of the same clone. The fold increase in CD66a staining above the background of each clone is indicated in brackets. The percent inhibition of each clone was calculated by dividing the percentage of specific lysis of the NK clone incubated with anti-CD66 mAb by that of the clone incubated with no mAb. Similar results were obtained when the specific lysis of each NK clone incubated with anti-CD66 mAb was divided by the percent specific lysis of the same NK clone incubated with control mAb. The NK clones are presented in the figure in the order of the fold increase in CD66a above background. The figure shows CD16$^-$CD66$^-$ clones (24, 89, and 98), CD16$^-$CD66$^+$ clones (21, 79, 84, and 100), CD16$^+$CD66$^-$ clones (25, 47, 48, 63, and 64), and CD16$^+$CD66$^+$ clones (1, 2, 3, 9, 10, 13, 17, 30, 32, 34, 43, 44, 49, 58, 61, 65, 69, 70, 71, 73, 75, and 96). When CD16$^-$ NK clones were used, anti-NKp44 and NKp46 sera were included to stimulate the redirected lysis experiments. When CD16$^+$ NK clones were used, anti-CD16 mAb was included in the redirected lysis experiments. The figure shows NK clones generated from one healthy donor YF that contains an unusually high number of CD16$^+$CD66$^+$ NK clones.

To correlate the level of expression of CD66a on NK cells and the strength of inhibition, various NK clones (positive or negative for CD16) expressing different levels of CD66a were used. The redirected lysis of P815 cells was induced with either anti-CD16 mAb or anti-NKp44 and -NKp46 sera depending whether the NK clone tested expressed the CD16 protein. A direct correlation was observed between the level of CD66 expression on the surface of the NK clones and the percentage of inhibition of redirected lysis (FIG. 23). The level of CD66a expression had to be at least 2-fold above the background staining for efficient inhibition to occur (FIG. 23).

Elevation of CD66a Expression on NK Cells Derived from Melanoma Patients

The in vivo significance of the CD66a interactions was studied by the staining of NK cells derived from either metastasized lymph nodes or peripheral blood. The lymph node of patient M-169 was infiltrated with melanoma cells, highly positive for the CD66a expression (MFI, 247). The lymph node was surgically removed, and lymphocytes in direct contact with the tumor cells were obtained after digestion and density gradient separation. Quadruple staining of the lymphocytes was performed for the expression of the CD16, CD3, CD56, and CD66 receptors. Remarkably, 12.85% of the NK cells (CD56$^+$CD3$^-$) obtained from M-169 lymph node expressed the CD66a protein (FIG. 24A). A total of 10.5% of the NK cells obtained were CD16$^-$CD66$^+$, and 2.35% were CD16$^+$CD66$^+$. The MFI of the CD66a-positive NK population was 8-fold above background, which is sufficient for effective inhibition (an MFI >2-fold above background is needed; see FIG. 23). Similar results were obtained when peripheral blood NK cells derived from patient 3 were analyzed with the same quadruple staining; 14.8% of the NK cells were CD66a positive, and the MFI of this NK population was 7.5-fold above background (FIG. 24B).

In contrast, little or no CD66a expression was observed among NK cells derived from the metastasized lymph node of patient M-172 (FIG. 24C). Strikingly, the infiltrating M-172 melanoma cells did not express the CD66a protein. Furthermore, no CD66a expression was observed among NK cells derived from the peripheral blood of 10 other melanoma patients with no clinical evidence of active disease.

Figure 24:
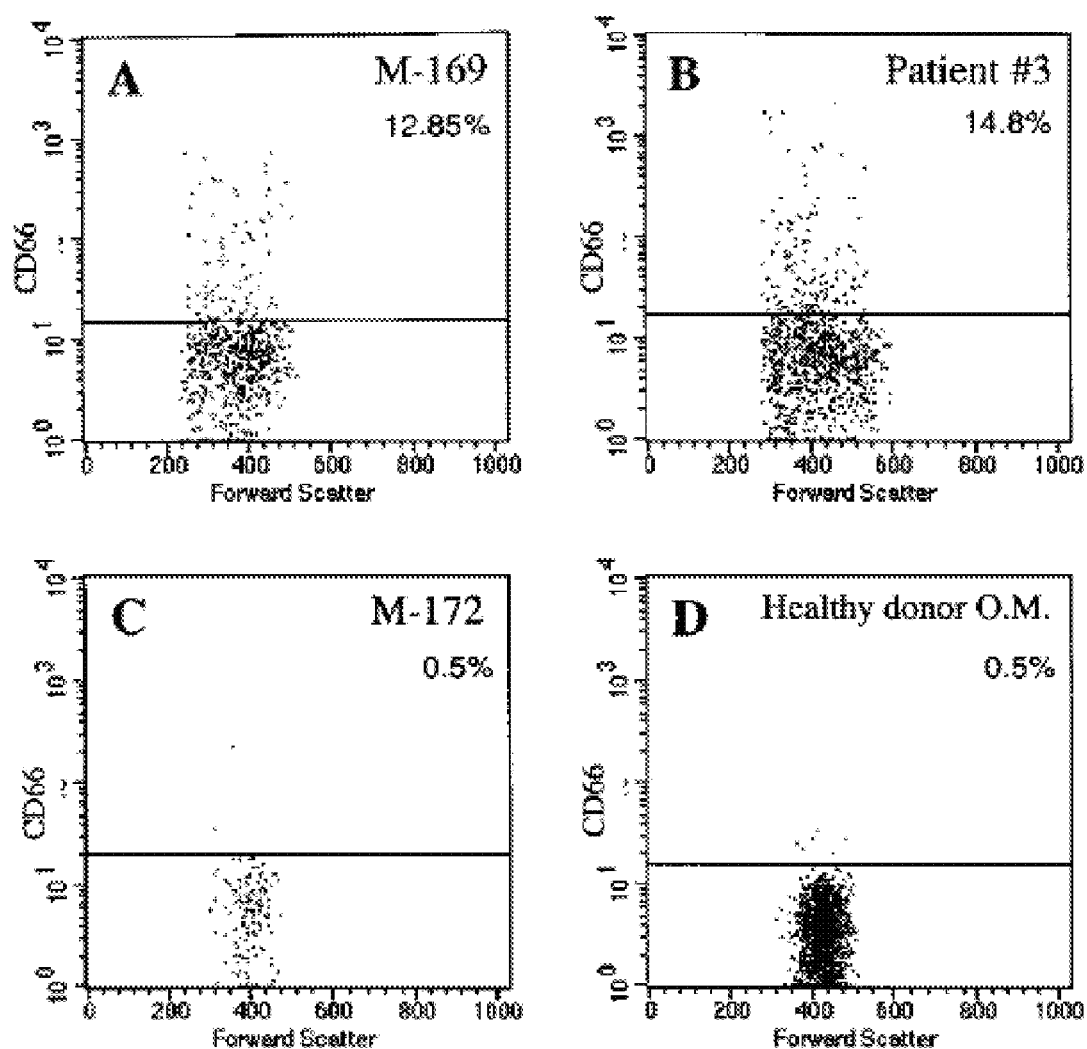
FIG. 24. CD66a expression on NK cells derived from healthy donors and melanoma patients. Lymphocytes were obtained from surgically removed lymph nodes derived from two different melanoma patients, infiltrated with melanoma metastases positive (A) or negative (C) for CD66a expression. Lymphocytes were also obtained from peripheral blood of another melanoma patient (B) or from peripheral blood of representative healthy donor (D). Lymphocytes were stained for expression of CD3, CD16, CD56, and CD66 as described in Materials and Methods of this section. The figure shows CD66a expression on NK cells.

PBL from eight healthy donors were also obtained, and the expression of CD66a on NK cells was analyzed using the same quadruple staining as that described above. Very little or no CD66 staining was observed among all NK cells tested (a representative healthy donor OM is shown in FIG. 24↑D). This is in agreement with an other observation demonstrating the expression of the CD66a molecule on activated NK clones only.

CD66a interactions are used by some melanoma cells as a mechanism of defense to avoid attack by CD66a-positive NK cells.

TABLE 6

Expression of various putative lysis ligands on human melanoma cell lines

| Melanoma Cell Lines | CD99-Ig | CD16-Ig | NKp30-Ig | NKp44-Ig | NKp46-Ig |
|---|---|---|---|---|---|
| L33melA1 | 0.0 | 0.20 | 2.71 | 3.28 | 0.52 |
| L33melB1 | 0.0 | 1.14 | 8.76 | 6.41 | 1.45 |
| 1106mel | 0.0 | 3.70 | 39.1 | 15.22 | 3.05 |
| FO-1 | 0.0 | 2.44 | 12.32 | 13.47 | 2.26 |
| 1259mel | 0.0 | 1.24 | 13.81 | 11.63 | 6.01 |
| 1074mel | 0.0 | 1.16 | 12.42 | 24.35 | 2.44 |
| 1612mH | 0.0 | 0.0 | 4.49 | 20.15 | 9.75 |
| 1612mel | 0.0 | 0.1 | 2.53 | 15.28 | 2.71 |

Melanoma cell lines were stained with various Ig fusion proteins as described in Materials and Methods of this section. Data are presented as MFI after subtraction of the background PE-conjugated anti-human Fc staining and are representative of one experiment of three performed.

TABLE 7

Expression of class I MHC and CD66a proteins on human melanoma cell lines

| Melanoma Cell Lines | Background | W632 | Kat4c |
|---|---|---|---|
| 1106mel | 2.97 | 3.25 | 200 |
| 1074mel | 3.25 | 3.25 | 137.7 |
| 1259mel | 1.60 | 1.60 | 108.3 |
| 1612mel | 3.13 | 3.79 | 35.5 |
| FO-1 | 2.60 | 2.44 | 25.9 |
| 1612mH | 3.79 | 3.82 | 25.4 |
| L33melB1 | 2.89 | 78.4 | 15.5 |
| M-77 | 3.59 | 257 | 120 |
| M-112 | 2.19 | 154 | 91 |
| M-112 | 2.19 | 154 | 91 |
| M-21 | 3.55 | 449 | 84.6 |
| M-5 | 3.55 | 1555 | 67.5 |
| M-139/1 | 4.68 | 1286 | 49.7 |
| M-128 | 1.67 | 226 | 39 |
| M-147 | 2.39 | 518 | 26.9 |
| M-145 | 5.1 | 1715 | 23.1 |
| M-117 | 4.66 | 143 | 15.6 |
| M-144 | 2.97 | 159 | 6.3 |
| M-82 | 2.79 | 109 | 6.0 |
| M-139/2 | 5 | 1000 | 5.0 |
| M-133 | 2.48 | 2308 | 3.02 |
| L33melA1 | 2.81 | 132 | 3.16 |
| M-90 | 1.89 | 1382 | 2.23 |

Staining of class I MHC-negative and -positive melanoma cell lines was performed with the pan anti-class I mAb W632 and the anti-CD66 mAb Kat4c. Similar staining levels of all melanoma cell lines were observed when the anti-CD66a mAb 5F4 was used. Data (MFI) are representative of one experiment of three performed.

Example 5

Pivotal Role of CEACAM1 Protein in the Inhibition of Activated Decidual Lymphocyte Functions Lymphocytes in direct contact with embryonic extravillous trophoblasts constitute more than 40% of decidual cells and appear to play major roles in implantation and early gestation. A unique subset of NK cells, making tip 70-80% of decidual lymphocytes, express high levels of CD56 but lack CD16.

The present inventors have demonstrated a novel class I MHC-independent inhibitory mechanism of NK cell cytotoxicity that is mediated by CEACAM1 homotypic interactions. This mechanism is used by some melanoma cells to avoid attack, mainly by CD16– NK cells. The present invention demonstrate that CEACAM1 is expressed on primary extravillous trophoblasts and is upregulated on the vast majority of IL-2-activated decidual lymphocytes, including NK, T, and NKT cells. In this section it is shown that CEACAM1 interactions inhibit the lysis, proliferation, and cytokine secretion of activated decidual NK, T, and NKT cells, respectively. In vivo analysis of decidual lymphocytes isolated from cytomegalovirus-infected (CMV-infected) pregnant women revealed a dramatic increase in the expression of CEACAM1. It is possible that a novel ligand for this adhesion molecule is present on the surface of CMV-infected fibroblasts. This section demonstrates a major role for the CEACAM1 protein in controlling local decidual immune responses. [Gal Markel et al., *Pivotal role of CEACAM1 protein in the inhibition of activated decidual lymphocyte functions, The Journal of Clinical Investigation,* 110:943-953 (2002). This reference is herein incorporated by reference.]

During embryonic implantation, the extravillous trophoblast (EVT) cells invade the uterine endometrium. At this site, a direct-contact interface forms between maternal and embryonic cells, which locally modifies the properties of the uterine mucosa. Embryonal-maternal interface together with specialized ECM constitutes the decidua basalis. Remarkably, more than 40% of decidual cells are immune cells. This suggests that the maternal immune system is involved in the modulation of maternal-embryonal interactions. The decidual lymphocyte composition differs significantly from that of peripheral blood lymphocytes. More than 70% of decidual lymphocytes are CD56bright CD16– (FcRγII) NK cells, while T cells constitute only 10%. In contrast, only 10% of the peripheral blood lymphocytes are NK cells that are characterized by a moderate expression level of the CD56 protein and the expression of the CD16 receptor. It is currently believed that decidual lymphocytes are important for control of normal trophoblastic growth, differentiation, and invasion. However, their role in combating pathogens in the context of pregnancy is only poorly understood.

The gentle balance between immune tolerance and immune activation that might lead to the rejection of the embryo by the decidual lymphocytes is maintained via several mechanisms, involving both decidual lymphocytes and EVTs. EVT invasion might be controlled by the modulation of the local cytokine profile, and therefore the cytokine release of decidual lymphocytes must be tightly regulated. The killing activity of both NK cells and CTLs, belonging to the innate and adaptive branches of the immune system, respectively, is regulated by the class I MHC proteins. While the recognition of the class I MHC proteins by the T cell receptors (TCRs) of CTLs activates T cell-mediated killing, the interactions between NK cells and the same proteins suppress NK cell cytotoxicity. It was reported that EVTs express an unusual combination of two nonclassical class I MHC proteins, the HLA-E and HLA-G, along with the classical HLA-C protein, but that they do not express the HLA-A and HLA-B proteins. As most of the CTLs are directed against HLA-A and -B proteins, this unique pattern of expression of class I MHC proteins probably prevents rejection of the semiallogeneic fetus by CTLs. The HIV virus uses a similar mechanism of specific downregulation of HLA-A and -B proteins, mediated by the Nef protein, to avoid attack by CTL.

NK cells compose the vast majority of decidual lymphocytes that are in contact with EVTs. The fetus is protected from rejection by maternal NK cells for several reasons. First, decidual NK cell inhibition appears skewed toward HLA-C recognition, compared with peripheral blood NK cells. Fifty to eighty percent of decidual NK cells are inhibited by HLA-C, compared with only 5-20% of the peripheral blood NK cells. Second, virtually all decidual NK cells express the HLAE-binding inhibitory receptor complex CD94/NKG2A five times more than do peripheral blood NK cells. Furthermore, the HLA-E protein, which is expressed on cell surface upon binding of peptides derived from the leader sequence of various class I MHC proteins, binds, with the greatest affinity, the leader peptides of HLA-G and HLA-C proteins, which are both expressed on the EVT cells. Third, all decidual NK cells express the inhibitory LIR1 (ILT2) or KIR2DL4 receptors, both of which are able to interact with the HLA-G proteins. Fourth, decidual NK cells have decreased killing activity against class I MHC-negative target cells. This wide spectrum of mechanisms aimed at controlling the cytolytic function of decidual NK cells further demonstrates the importance of these cells in the rejection of allogeneic transplants. It also implies that other mechanisms with the ability to control the function of decidual lymphocytes might exist.

The CEACAM1 protein, a member of the CEACAM family, is expressed on a broad spectrum of cells (13). It belongs to the Ig superfamily and interacts in both a homotypic manner and a heterotypic manner with other variants of the CEACAM family, including the CEACAM6 and CEACAM5 proteins. The CEACAM1 homotypic interactions between NK cells and various target cells inhibit NK cytotoxicity. This novel class I MHC-independent mechanism appears to be used mainly by CD16– NK cells and might play an important role in the development of various pathologies, such as melanoma.

It is shown that CEACAM1 is expressed by EVTs as well as by the majority of IL-2-activated decidual lymphocyte subsets. The engagement of the CEACAM1 protein leads to the inhibition of NK killing, T cell proliferation, and IFN-γ secretion by NKT cells. The in vivo upregulation of the CEACAM1 protein on the majority of decidual lymphocytes might have an important role in controlling local immune response. This is demonstrated by the analysis of decidual lymphocyte subsets obtained from decidua of cytomegalovirus infected (CMV-infected) women, which revealed a dramatic upregulation of surface CEACAM1 expression. In addition, evidence is provided that CEACAM1 binds and functionally interacts with an unidentified molecule present on human primary fibroblasts infected with the laboratory AD169 CMV strain or with a clinical CMV strain isolated from infected decidua. These combined results suggest a major role for the CEACAM1 protein in controlling local decidual immune responses.

Methods

Cells, Transfections, Virus Propagation, and Antiviral, Agent

The cell lines used in this section were the class I MHC-negative Epstein-Barr virus-transformed B cell line 721.221 (0.221), 0.221 cells transfected with the CEACAM1 cDNA, and the murine thymoma BW cell line, which lacks expression of α and β chains of the TCR. Stable transfection of 0.221 cells expressing CEACAM6 and CEACAM5 was performed by electroporation (0.23 kV, Cap uF] 250 uF). The cDNA for CEACAM6 was amplified by RT-PCR and cloned into pcDNA3 expression vector, and the CEACAM5 cDNA was a kind gift from W. Zimmermann, Ludwig-Maximilians-University, Muenchen, Germany) Human foreskin fibroblasts (HFFs) were used for propagation and infection of human CMV strain AD169 (American Type Culture Collection, Manassas, Va., USA), as previously described. After a 1-hour period of virus adsorption to cells, 300 ug/ml of the CMV DNA polymerase inhibitor phosphonoformate (PFA; Sigma-Aldrich, St. Louis, Mo., USA) was added for inhibition of virus replication.

Primary CMV Infection, Definition of Congenital CMV Infection, and Termination of Pregnancy Primary CMV infection during pregnancy was diagnosed by documentation of maternal seroconversion, with appearance of CMV antibodies during pregnancy in women known to be CMV seronegative before gestation. Diagnosis of CMV fetal infection was based on viral isolation (by shell viral culture and conventional culture) from amniotic fluid obtained at the 22nd week of gestation, along with PCR detection of viral DNA in the amniotic fluid. Congenital disease could be predicted by the presence of characteristic ultrasonographic findings including cerebral calcifications and microcephaly. Decision to terminate pregnancy was based on documentation of fetal infection and disease. Deciduae from first-trimester elective terminations were obtained by scraping.

Antibodies

The mAb's used in this section were FITC conjugated Kat4c mAb directed against CEACAM1, -5, and -6 (DAKO, Glostrup, Denmark), phycoerythrin conjugated anti-CD56 mAb (BD Pharmingen, San Diego, Calif., USA), CyChrome-conjugated anti-CD3 mAb (BD Pharmingen), and biotinylated anti-CD16 mAb (Serotec, Oxford, United Kingdom), followed by Cy5-streptavidin (Jackson ImmunoResearch Laboratories Inc., West Grove, Pa., USA). The anti-CD4 mAb (DAKO), anti-Vβ3 (BD Pharmingen), anti-Vβ17 (BD Pharmingen), and the anti-CEACAM1 5F4 mAb were also used. For blocking assays, rabbit polyclonal anti-CEACAM1, -5, and -6 (DAKO) antibodies and the control rabbit polyclonal antibodies against purified ubiquitin were used. The following anti-IFN-γ mAb's were purchased from BD Pharmingen: mAb B27, used for measuring intracellular IFN-γ production; and biotinylated mAb 4S.B3 (detection) and purified mAb HIB42 (capture), both used in the ELISA assays. The production of mouse IL-2 from BW/CEACAM1ξ-transfected cells was detected by ELISA using purified anti-mouse IL-2 mAb JES6-1A12 (capture) and biotinylated anti-mouse IL-2 mAb JES6-5H4 (detection) (both from BD Pharmingen). ELISA assays were performed according the manufacturer's instructions (BD Pharmingen).

Isolation of Decidual Lymphocytes

The Hadassah Medical Organization Institutional Board approved obtaining deciduae from elective pregnancy-termination procedures, from induced labors, and from caesarian sections, in keeping with the principles of the Helsinki Declaration. The tissue was trimmed into 1-mm pieces and enzymatically digested for 20 minutes, using vigorous shaking, with 1.5 mg type I DNase and 24 mg type IV collagenase present in 15 ml of RPMI-1640 medium. This procedure was repeated three times. After an additional 5 minutes' incubation at room temperature without shaking, the supernatants were collected and incubated overnight in a tissue culture dish. Nonadherent cells were collected and loaded on Ficoll density gradient to purify the lymphocyte population. Cells were further analyzed by flow cytometry. NK and NKT cells were purified using anti-CD56 mAb followed by incubation with microbeads of conjugated goat anti-mouse IgG antibodies (Miltenyi Biotec Inc., Auburn, Calif., USA). Separation was performed with the AutoMACS instrument (Miltenyi Biotec Inc.). Positive (NK and NKT cells) and negative (T cells) fractions were collected and cloned (one cell per well) in the presence of IL-2.

Quadruple Staining

For quadruple staining, the following fluorochrome-conjugated mAb's were used: FITC conjugated anti-CEACAM Kat4c mAb (DAKO), phycoerythrin-conjugated anti-CD56 mAb (BD Pharmingen), and CyChrome-conjugated anti-CD3 mAb (BD Pharmingen). As the fourth color, biotinylated anti-CD16 mAb (Serotec) was used, followed by Cy5-streptavidin (Jackson ImmunoResearch Laboratories Inc.) as a second reagent. To block nonspecific binding, cells were first incubated for 1 hour on ice with 25% human serum, and then incubated with the various antibodies.

Cytotoxicity Assays

The cytotoxic activity of NK cells against the various targets was assayed in 5-hour 35S release assays, as described previously. Briefly, cells were labeled overnight with 35S-methionine and washed, and 5·103 labeled target cells were incubated at various effector-to-target ratios. The killing rate was calculated as percent 35S-methionine release=(cpm sample−cpm spontaneous release)/(cpm total−cpm spontaneous release)×100. Total 35S-methionine release was measured after incubation of the cells with 0.1 M NaOH. In all presented cytotoxic assays, the spontaneous release was less than 25% of maximal release. In experiments where mAb's were included, the final mAb concentration was 10 ug/ml, or 40 ul/ml in those cases where rabbit polyclonal antibodies were used.

Staphylococcal Enterotoxin B-Induced T Cell Proliferation

These assays were performed as previously described. Briefly, target 0.221 and 0.221/CEACAM1 cells were irradiated (60 Gy). Thereafter, 50,000 T cells, 25,000 target cells, and various concentrations of superantigen were mixed in a total volume of 200 ul of RPMI-10% FCS in each well of a 96-well plate. After incubation at 37° C. and 5% CO2 for 2 days, 1 uCi of 3H-thymidine was added to each well and the cells were further incubated at 37° C. overnight. The cells were then harvested and counted on a liquid scintillation counter (1450 Micro-Beta PLUS; Wallac, Turku, Finland). In analysis of the cpm from each well, the background cpm from wells in which identical reagents and target cells were placed in the absence of any T cells was subtracted.

Generation of Ig Fusion Proteins

The extracellular portion of the CEACAM1 protein was amplified by PCR using the following primers: 5'-CCCAAGCTTGGGGCCGCCAC-CATGGGGCACCTCTCAGCC (including HindIII restriction site) (SEQ ID NO 10) and 3'-GCGGATCCCCAGGT-GAGAGGC (including BamHI restriction site) (SEQ ID NO 30). A silent mutation, adenine 885 guanidine (no change in glycine 281), was performed by site-directed mutagenesis to cancel the BamHI site in the amplified sequence. The generation, production, and staining procedures of the Ig fusion proteins were previously described. [Gal Markel et al., Pivotal role of CEACAM1 protein in the inhibition of activated decidual lymphocyte functions, The Journal of Clinical Investigation, 110:943-953 (2002). This reference is herein incorporated by reference.] Briefly, the PCR-generated fragments were cloned into a mammalian expression vector containing the Fc portion of human IgG1 (a kind gift from B. Seed, Massachusetts General Hospital, Department of Molecular Biology, Boston, Mass., USA). Sequencing of the constructs revealed that all cDNAs were in frame with the human Fc genomic DNA and were identical to the reported sequences. COS-7 cells were transiently transfected with the plasmids containing cDNAs using FuGENE6 reagent (Roche Molecular Biochemicals, Indianapolis, Ind., USA) according to the manufacturer's instructions, and supernatants were collected and purified on a protein G column. SDS-PAGE analysis revealed that all Ig fusion proteins were approximately 95% pure and of the proper molecular mass. To assay for the CEACAM binding, various cells were incubated with 50 ug/ml of fusion protein for 2 hours on ice. The cells were washed and incubated with Fc fragment-specific (minimal cross-reaction to bovine, horse, and mouse serum proteins), phycoerythrin-conjugated affinity-purified F(ab2)2 fragment of goat anti-human IgG (Jackson ImmunoResearch Laboratories Inc.). Incubation was performed for 1 hour and analyzed by flow cytometry with a FACScan (Becton Dickinson Immunocytometry Systems, San Jose, Calif., USA).

Generation of BW Cells Expressing the Chimeric CEACAM1 ƒ Protein and the Production of IL-2

The extracellular portion of the human CEACAM1 protein was amplified by PCR using the following primers: 5'-CCCAAGCTTGGGGCCGCCAC-CATGGGGCACCTCTCAGCC (including HindIII restriction site) (SEQ ID NO 10) and 3'-GTAGCAGAGAGGT-GAGAGGCCATTTTCTTG (including first nine nucleotides of mouse .xi. chain transmembrane portion). The mouse .xi. chain was amplified by PCR using the following primers: 5'-CTCTCACCTCTCTGCTACTTGCTAGATGGA (including last nine nucleotides of human CEACAM1 extracellular portion) (SEQ ID NO 31) and 3'-GGAATTCCTTAGC-GAGGGGCCAGGGTCTG (including EcoRI restriction site) (SEQ ID NO 32). The two amplified fragments were mixed, and PCR was performed with the 52.quadrature.HindIII primer and the 32 EcoRI primer for the generation of the CEACAM1 construct. The CEACAM1.quadrature. construct was cloned into pcDNA3 expression vector (Invitrogen Corp., Carlsbad, Calif., USA) and stably transfected into BW cells. For measurement of IL-2 production resulting from the homotypic CEACAM1 interactions, 50,000 BW or BW-transfected cells were incubated in RPMI-10% FCS medium for 48 hours at 37.degree. C. and 5% CO2. Supernatants were collected and the presence of IL-2 was monitored by using anti-IL-2 mAb and standard ELISA assays (BD Pharmingen). For measurement of IL-2 production resulting from the CEACAM1 interactions of different cell types, 50,000 BW or BW-transfected cells were incubated in RPMI-10% FCS with irradiated 0.221 or with 0.221/CEACAM1 cells for 24 hours or with CMV infected HFF cells for 48 hours at 37.degree. C. and 5% CO2. The presence of mouse IL-2 in cell supernatants was measured as above.

Cross-Linking of NKT Cells

NKT cells (105 per well) were incubated with or without 0.5 ⌈ g of Kat4c mAb on ice for 1.5 hours in 96 round bottom microplates (Nalge Nunc, Rochester, N.Y., USA). Treated NKT cells, present in 200 ul of IL-2-containing medium, were then cultured in 96 flat bottom microplates (Nalge Nunc) precoated with 1 ug/well of sheep antimouse IgG antibodies (ICN Biomedicals Inc., Costa Mesa, Calif., USA) for 24 hours at 37° C. Cells were then analyzed by FACS.

Permeabilization and Intracellular IFN-γ Staining

The permeabilization and intracellular IFN-© staining were performed using the Cytofix/Cytoperm Plus (with GolgiStop) kit (BD Pharmingen) according to the manufacturer's instruction.

Results

CEACAM1 is Expressed on Different Decidual Lymphocytes after Activation

Figure 25:
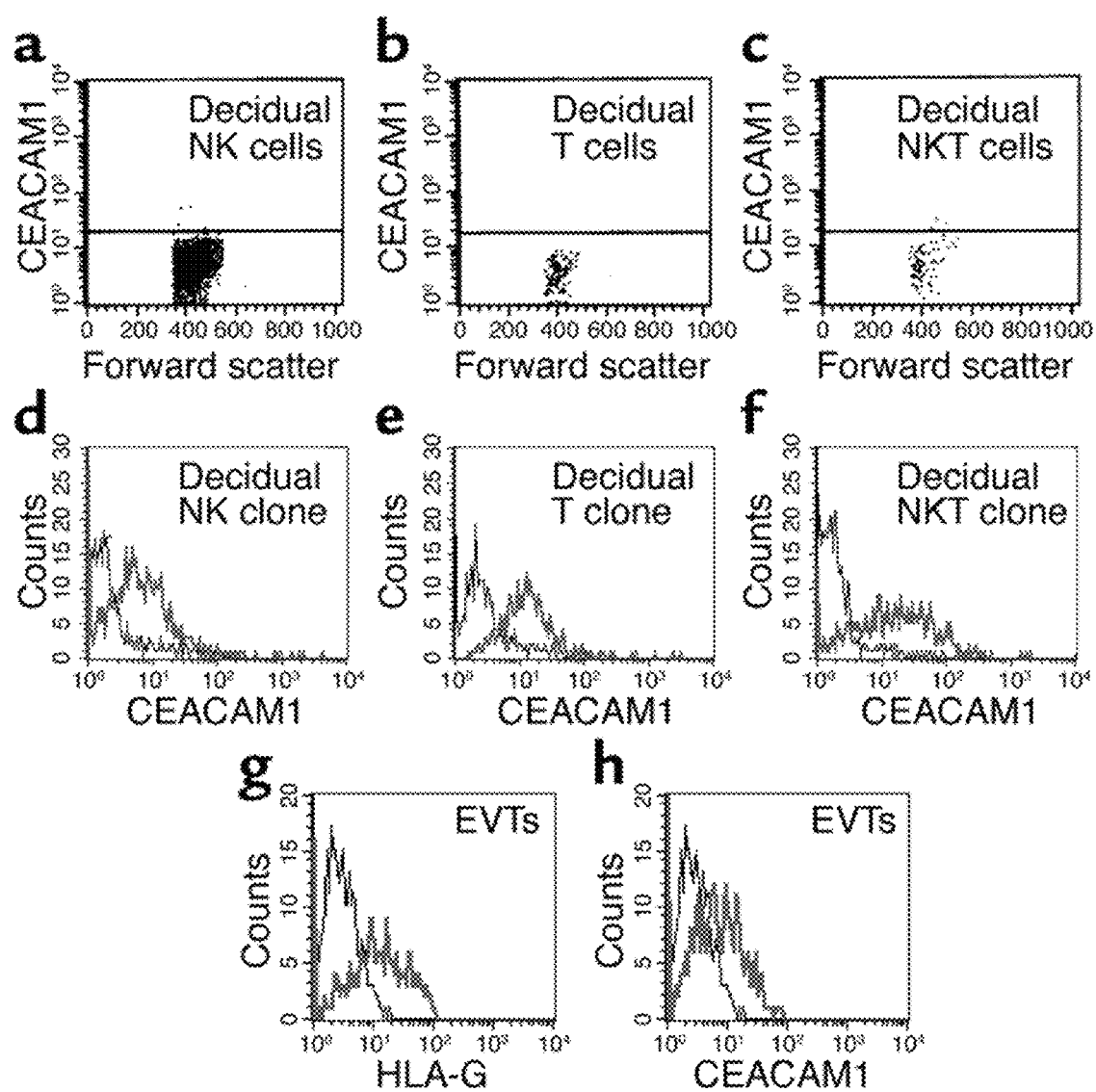
FIG. 25. CEACAM1 staining of decidual lymphocytes. Decidual lymphocytes were isolated and quadruple-stained as described in Methods. (a-c) CEACAM1 staining on non-activated decidual NK cells (a), T cells (b), and NKT cells (c). One representative experiment is shown out of three performed. Decidual lymphocytes were cultured in the presence of IL-2 as described (20) and then screened for CEACAM1 expression with the 5F4 mAb. (d-f) CEACAM1 staining for activated decidual NK clone (d), T clone (e), and NKT clone (f). Similar results were obtained when other lymphocyte clones were used. (g and h) Staining of EVTs for HLA-G and CEACAM1, respectively. Bold lines represent mAb staining and thin lines show background staining.

To test the possible role of CEACAM1 in controlling decidual lymphocyte functions, decidual lymphocytes from first-trimester elective pregnancy terminations were isolated as described in Methods. Obtained tissues were identified as decidua by histologic analysis. Lymphocytes were isolated from nine different deciduae and quadruple-stained using flow cytometry for the expression of CD3, CD16, CD56, and CEACAM. In agreement with previous observations, the total decidual lymphocyte population contained mainly CD16− NK cells (70-80%, characterized by CD3−CD56bright), but T (characterized by CD3+ CD56−) and NKT (characterized by CD3+ CD56+) cells were also identified (5.3% and 3.2%, respectively). Little or no staining for the CEACAM1 protein was observed among all decidual lymphocyte populations tested (FIG. 25, a-c).

Various lymphocytes were cloned and cultured for 3 weeks in the presence of IL-2 (50 U/ml). Remarkably, staining with the 5F4 anti-CEACAM1 mAb (see FIG. 26) revealed a dramatic increase in the CEACAM1 protein expression on the surface of the vast majority of NK, T, and NKT cell clones tested (85%, 86%, and 95%, respectively; surface expression of CEACAM1 on representative clones is shown in FIG. 25, d-f). This is in marked contrast to NK cells derived from peripheral blood, in which surface CEACAM1 expression could be detected on only 2-3% of IL-2-activated CD16+ NK clones and on about 45% of the IL-2-activated CD16− clones. Notably, the expression levels of the CEACAM1 on the surface of all tested clones were more than threefold above background. This level of expression was reported to be sufficient for effective inhibition of NK cytotoxicity.

Figure 30:
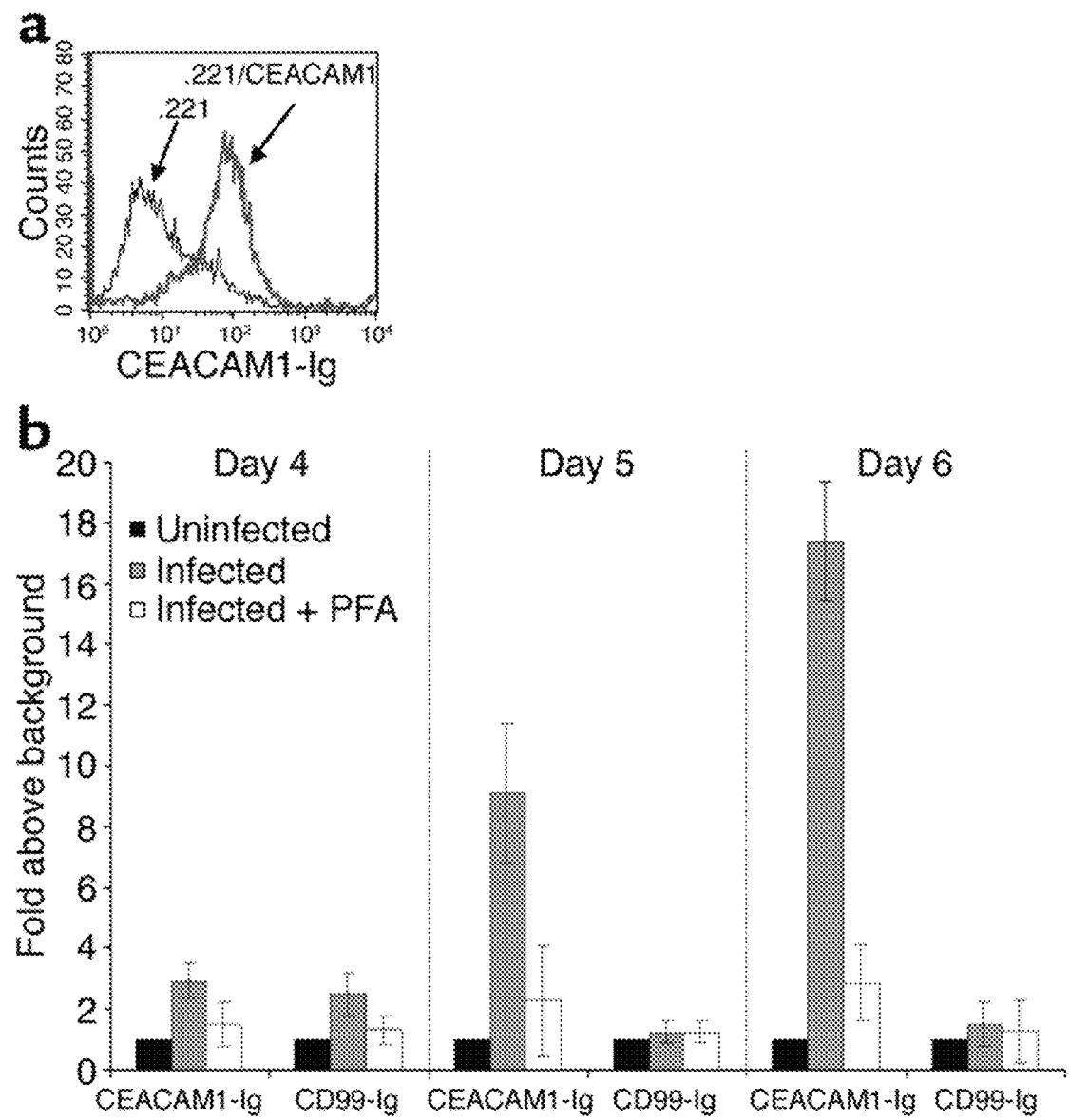
FIG. 30. CEACAM1-Ig specifically binds to CMV-infected fibroblasts. (a) Binding of CEACAM1-Ig to 0.221/ CEACAM1 cells (bold line) but not to parental 0.221 (thin line). The figure shows a representative experiment out of three performed. (b) Day-by-day staining of uninfected and CMV-infected HFF cells in the presence or absence of 300 ☐g/ml of the antiviral agent PFA. Cells were stained with CEACAM1-Ig and with the control CD99-Ig fusion protein as described in Methods. Data are presented as fold increase above the staining of uninfected cells. The average of two independent experiments is shown.
Figure 31:
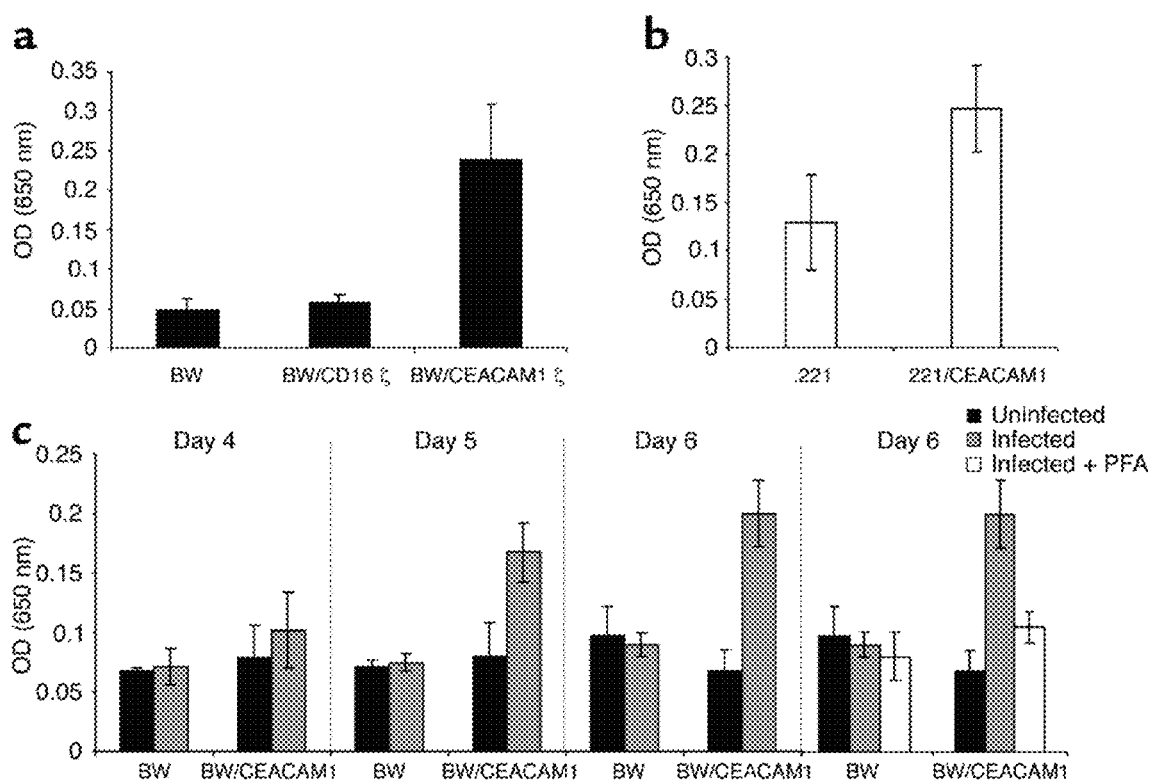
FIG. 31. The functional interactions between BW/CEACAM1☐ and CMV-infected HFFs elicit IL-2 secretion. (a) Spontaneous IL-2 secretion by BW and various BW transfectants after 48 hours of incubation. The average of 20 independent experiments is shown. (b) IL-2 secretion by BW/CEACAM1☐☐ cells coincubated for 24 hours with irradiated 0.221 or with 0.221/CEACAM1 cells. The average of six independent experiments is shown. (c) IL-2 secretion after coincubation of BW or BW/CEACAM1☐☐ cells with uninfected or CMVinfected HFF cells for 48 hours. No IL-2 secretion above background levels was observed when PFA was included in the assay (only day 6 is shown). Experiments were performed concomitantly with the flow cytometry binding assays of CEACAM1-Ig shown in FIG. 29. The average of two independent experiments is shown.

As the CEACAM1 protein interacts homotypically with other CEACAM1 proteins (see FIGS. 30 and 31) and decidual lymphocytes are in direct contact with embryonic EVT cells in vivo, it was important to test whether EVT cells express the CEACAM1 protein. EVT cells were obtained from the same elective pregnancy terminations from which decidual lymphocytes were isolated and were tested for the expression of HLA-G and CEACAM1. As the expression of HLA-G is restricted to EVT cells only, isolated cells were identified as EVT cells by using specific staining with the anti-HLA-G specific mAb MEM-G/13B. The mAb MEMG/13B specifically stains the class I MHC-negative 0.221 cells transfected with HLA-G; it did not stain 0.221 cells transfected with other class I MHC cDNA. FACS staining analysis of isolated EVT cells showed that these cells express the HLA-G (FIG. 25g) and the CEACAM1 (FIG. 25h) proteins. These findings suggest that CEACAM1 might mediate direct interactions between activated decidual lymphocytes and EVTs and thus might display a novel control mechanism protecting the embryo from sustaining damage.

CEACAM1 Interactions Inhibit Decidual NK Cytotoxicity

It has been demonstrated that the CEACAM1-mediated inhibition of NK cells can be blocked by using rabbit polyclonal anti-CEACAM antibodies and not by the mAb 5F4 or the mAb Kat4c [Markel, G., et al. 2002. CD66a *interactions between human melanoma and NK cells: a novel class I MHC-independent inhibitory mechanism of cytotoxicity J. Immunol* 168:2803-2810. 158:11-25. This reference is incorporated by reference.]. It is shown that the CEACAM1 protein interacts with other CEACAM proteins, such as CEACAM5 and CEACAM6, and that the binding site of CEACAM1 was located at the N-terminal Ig-V-type domain of the CEACAM1 protein (23). The N-terminal Ig-V-type domain of the CEACAM family reveals 70-90% sequence similarity among the different variants. It was therefore important to determine the specificity of all anti-CEACAM1 antibodies used in this work. 0.221 cells were transfected with CEACAM1, CEACAM6, and CEACAM5 and stained for surface expression using the various anti-CEACAM antibodies.

Figure 26:
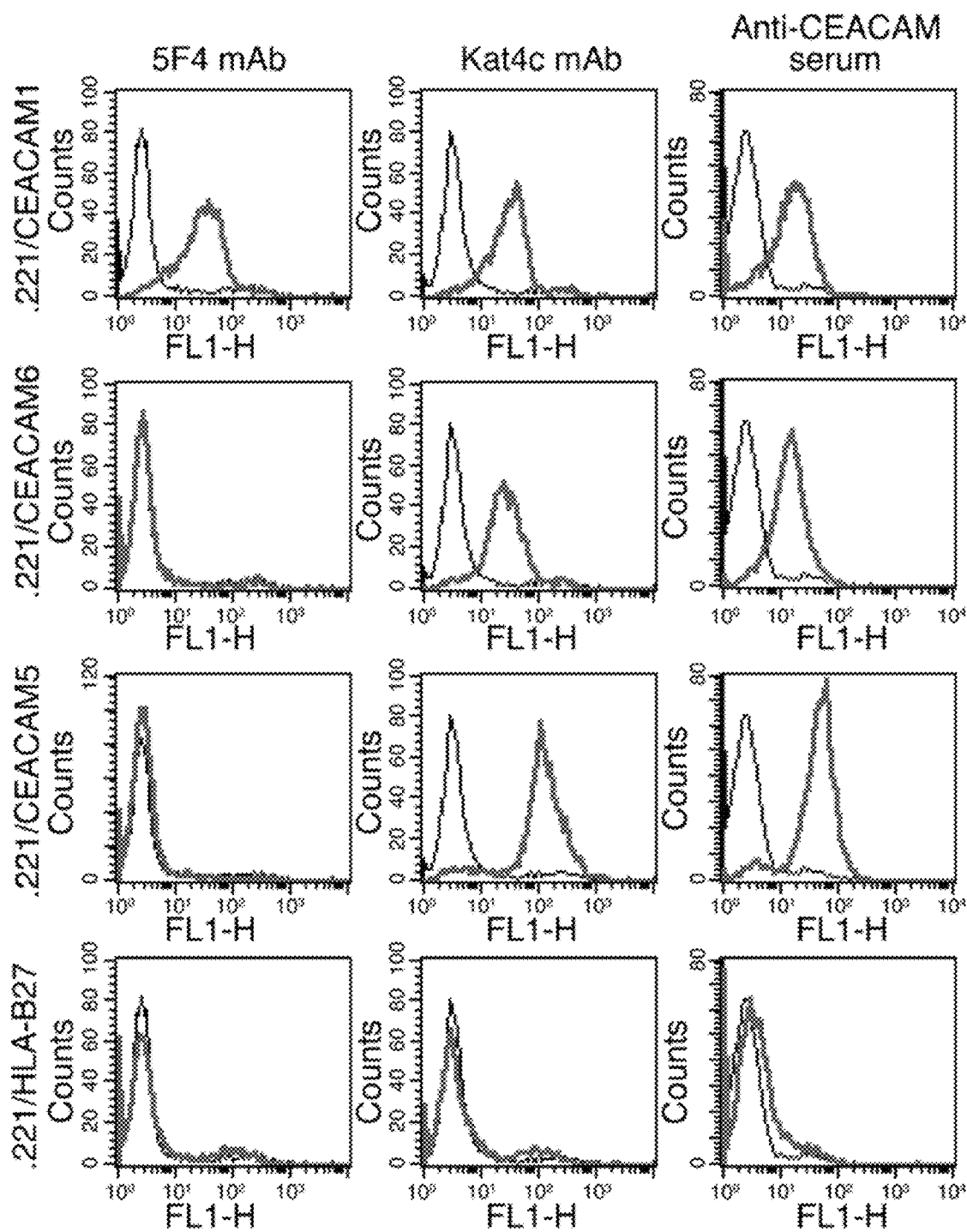
FIG. 26. Staining of 0.221 cells expressing various members of the CEACAM family using specific anti-CEACAM antibodies. 0.221 transfectants were generated as described in Methods. Each row shows the staining performed on a particular transfectant (indicated at left), and each column shows the staining with a particular antibody (indicated at top). Bold lines represent antibody staining and thin lines show background staining on 0.221 cells. One representative experiment is shown out of three performed.

FIG. 26 shows that all anti-CEACAM antibodies specifically recognized members of the CEACAM family. This is because no staining was observed on either nontransfected 0.221 cells or the control HLAB27-transfected 0.221 cells. The 5F4 mAb recognized the CEACAM1 protein only, whereas the Kat4c mAb and the rabbit polyclonal antibodies directed against CEACAM recognized CEACAM1, CEACAM6, and CEACAM5 proteins (FIG. 26).

Figure 27:
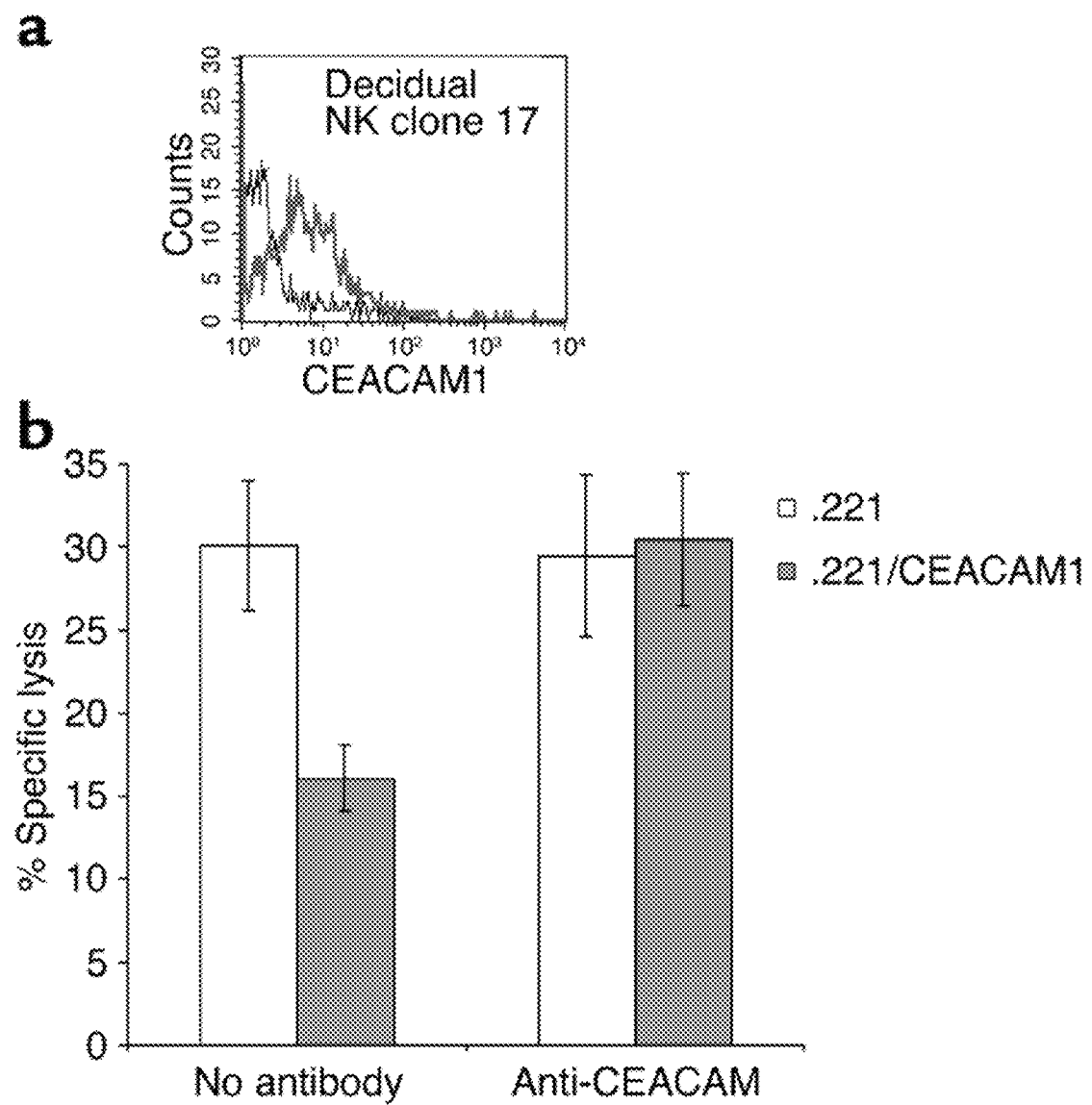
FIG. 27. CEACAM1-mediated inhibition of decidual NK cytotoxicity. Decidual NK clones were stained for CEACAM1 expression. (a) CEACAM1 staining of decidual NK clone 17 using the anti-CEACAM1 mAb 5F4 (bold line). The thin line shows the control staining. (b) Killing and inhibition of NK clone 17 by 0.221 cells and by 0.221 cells transfected with CEACAM1 (0.221/CEACAM1). Blocking experiments were performed using 40 μl/ml of anti-CEACAM antibodies. Average of three independent experiments is shown. Similar results were obtained when other CEACAM1+ NK clones were used.

To investigate whether the CEACAM1 protein is functional, IL-2-activated decidual NK clones, expressing the CEACAM1 protein (a representative clone is shown in FIG. 27a), were tested in killing assays against 0.221 cells and 0.221 cells transfected with CEACAM1 (0.221/CEACAM1). The generation of these transfectants was described previously (15). The CEACAM1+ NK clones effectively killed 0.221 cells, whereas inhibition of lysis was observed when 0.221/CEACAM1 cells were used (FIG. 27b). The inhibition of NK killing by 0.221/CEACAM1 cells was the result of the CEACAM1 homotypic interactions, as lysis of 0.221/CEACAM1 cells was restored when rabbit anti-human CEACAM antibodies were included in the assay. The addition of a control rabbit serum derived from ubiquitin-immunized rabbit had no effect. No difference in the lysis of 0.221 or 0.221/CEACAM1 cells was observed when CEACAM1− NK clones were used. Most decidual NK clones displayed only limited cytotoxicity against the 0.221 target cells (10-20% lysis). The killing of 0.221/CEACAM1 cells by "low killer" decidual NK clones was also decreased because of the homotypic CEACAM1 interactions, and the addition of anti-CEACAM polyclonal antibodies restored lysis.

Figure 28:
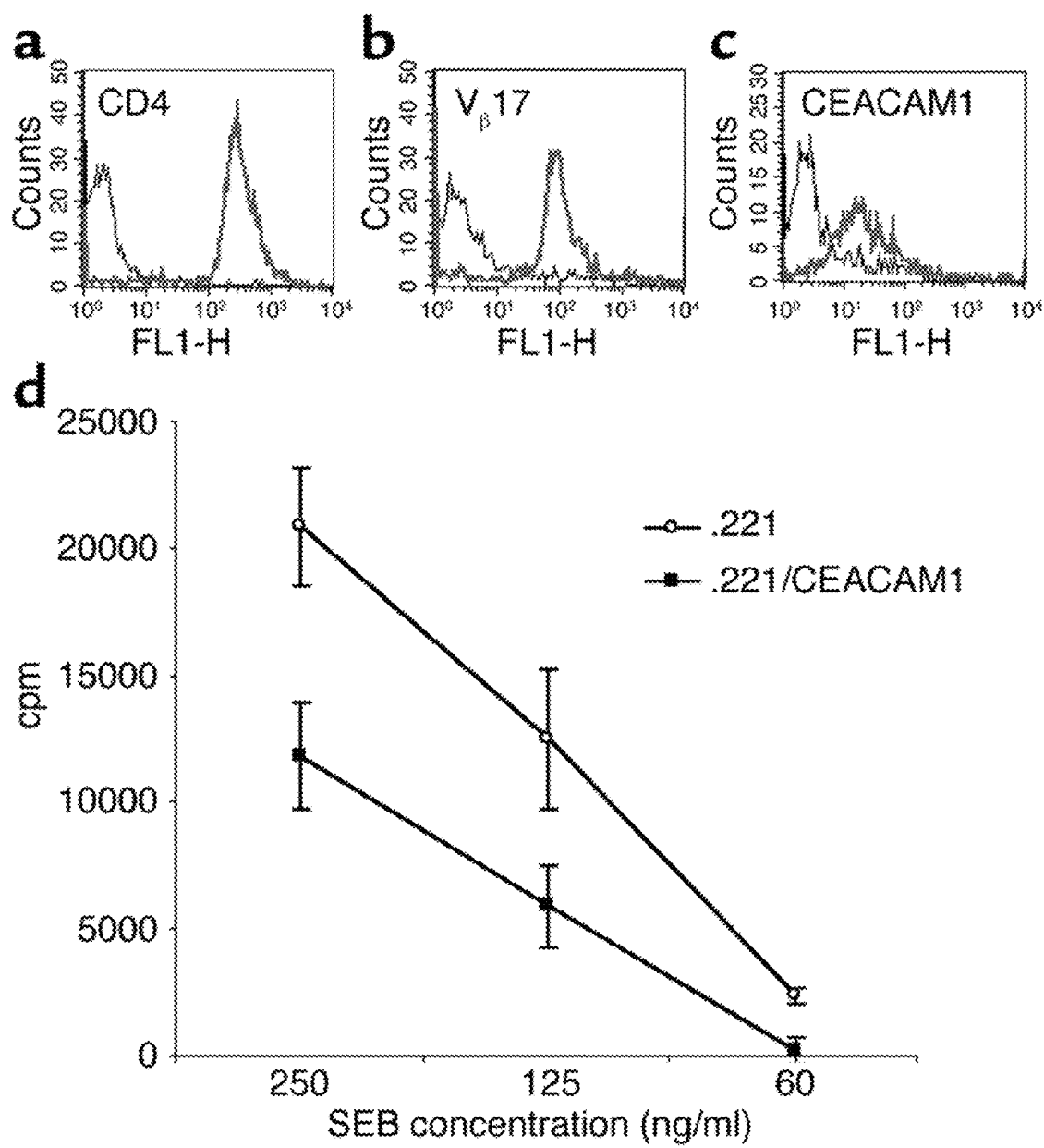
FIG. 28. CEACAM1-mediated interactions inhibit SEB-induced T cell proliferation. Decidual T cell clones were tested for expression of CD4 (a), V☐17 (b), and CEACAM1 (c) by flow cytometry. Bold lines indicate mAb staining and thin lines indicate control staining. (d) Fifty thousand cells of the presented T cell clone were incubated for 2 days with 25,000 irradiated 0.221 cells or with 0.221 cells transfected with CEACAM1 (0.221/CEACAM1), in the presence of decreasing SEB concentrations as indicated in the figure. Proliferation was measured with 3H-thymidine incorporation. The figure represents the average of ten independent experiments. Similar results were obtained when other T cell clones were used.

CEACAM1 Interactions Inhibit Staphylococcal Enterotoxin B-Induced Decidual T Cell Proliferation As the expression of CEACAM1 protein was also demonstrated on the vast majority of T lymphocytes activated by IL-2, the effect of CEACAM1 interactions on T cell proliferation was also tested. Superantigens can induce T cell proliferation by binding to class II MHC proteins and specific TCR Vβ chains. The staphylococcal enterotoxin B (SEB) superantigen interacts with various TCR. Vβ chains, including Vβ3 and Vβ17. Decidual T cell clones were obtained as described in Methods and screened by flow cytometry for the expression of CD4, Vβ3, and Vβ17 by using specific mAb's. A representative T cell clone, no. 1, stained brightly for both CD4 and Vβ17 (FIG. 28, a and b), and moderately for CEACAM1 (FIG. 28c). The SEB-induced proliferation of this T cell clone was assayed as described in Methods. A dramatic increase in the T cell proliferation was observed when cells were incubated with 0.221 cells in the presence of 250 ng/ml of SEB (50-fold above the background proliferation without SEB; data not shown). Efficient inhibition of the T cell proliferation (around 50%) was observed in all SEB concentrations tested when cloned T cells were incubated with 0.221/CEACAM1 cells (FIG. 28d). The expression levels of the class II MHC proteins were similar on both 0.221 and 0.221/CEACAM1 cells.

CEACAM1 Interactions Inhibit Secretion of Cytokines from Decidual NKT Cells

Figure 29:
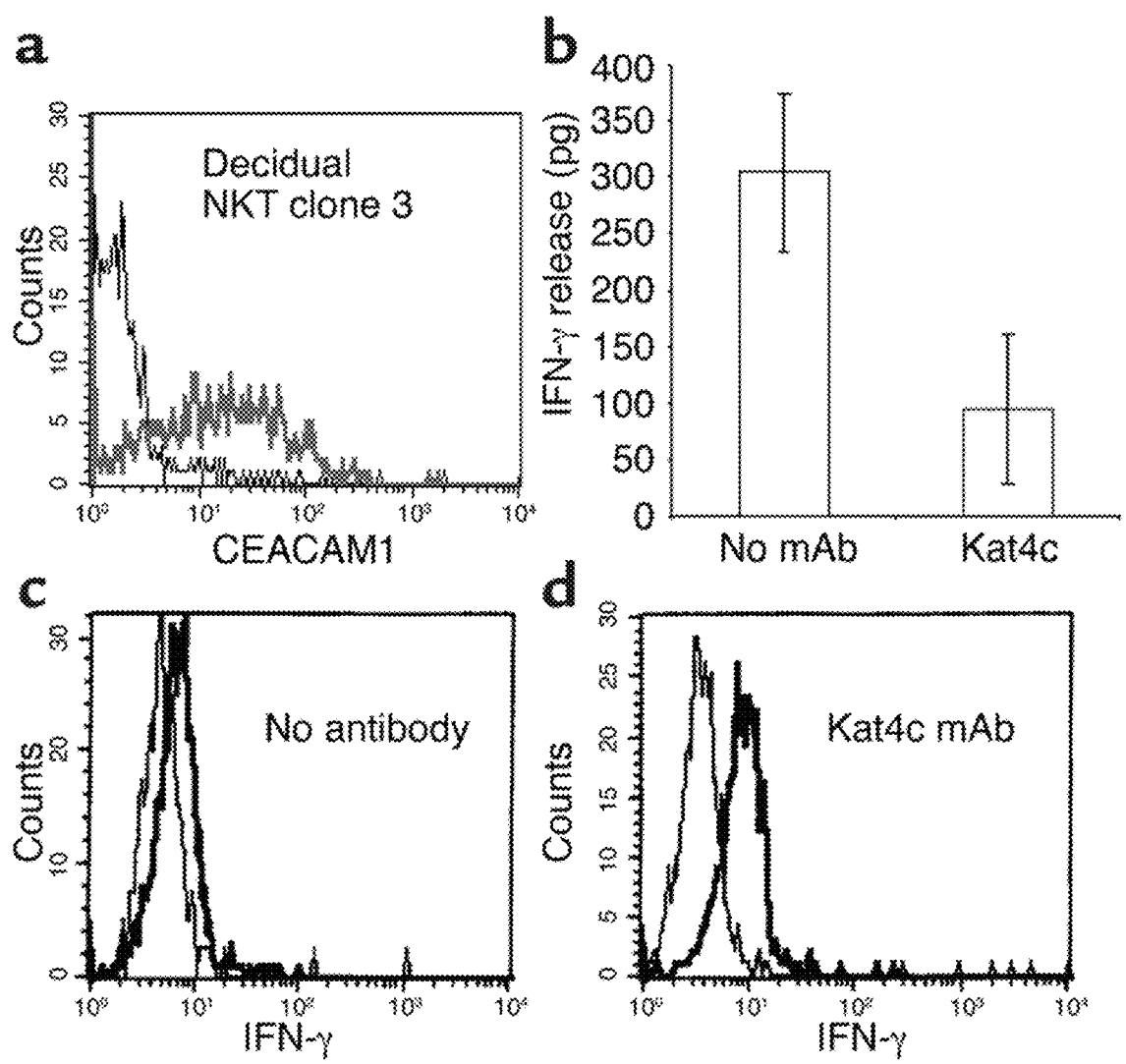
FIG. 29. CEACAM1-mediated inhibition of IFN-☐ secretion from NKT cells. (a) CEACAM1 expression on isolated activated NKT clone. The bold line shows the staining with 5F4 mAb, and the thin line shows the control staining. (b) The amount of IFN-☐ in culture supernatant of mAb-treated and untreated NKT clone cells measured by ELISA. The average of two independent experiments is shown. Cross-linking of surface CEACAM1 was performed without (c) or with (d) the Kat4c mAb, and intracellular staining for IFN-☐ was performed. One representative experiment is shown out of two performed. Similar results were obtained when other NKT cell clones were used.

Cytokines might play an important role in fetus development. NKT cells that are present among the decidual lymphocyte population (see FIG. 25) are able to produce large amount of cytokines. The functional effect of CEACAM1 interactions on cytokine secretion of decidual NKT cells has never been investigated. Decidual NKT clones were cultured as described in Methods and screened for CEACAM1 expression by flow cytometry, using the anti-CEACAM15F4 mAb (a representative NKT cell clone, no. 3, is shown in FIG. 29a). NKT clone 3 spontaneously secreted IFN-γ into the media, as measured by ELISA (FIG. 29b). Other cytokines such as IL-4, IL-5, IL-13, TNF, and macrophage inflammatory protein-1α could not be detected in culture supernatant of this clone. Cross-linking of CEACAM1 for 24 hours with the Kat4c mAb dramatically decreased the amount of IFN-γ detected in the medium of this NKT cell clone (FIG. 29b). In order to determine whether the inhibitory effect observed after cross-linking of CEACAM1 on NKT cells is the result of decreased secretion or decreased production of IFN-γ, the presence of intracellular IFN-γ, before and after cross-linking of CEACAM1, was tested by staining as described in Methods. Untreated NKT cells showed little staining for intracellular IFN-γ (median fluorescence intensity twofold above background; FIG. 29c). After cross-linking with the Kat4c mAb, the staining for intracellular IFN-γ increased significantly (median fluorescence intensity 4.5-fold above background; FIG. 29d). These findings suggest that CEACAM1 engagement on NKT cells suppresses the cytokine secretion machinery and not de novo synthesis.

In Vivo Upregulation of CEACAM1 on Decidual Lymphocytes

The above observations suggest a major role for the CEACAM1 protein in the regulation of decidual lymphocyte functions after IL-2 activation. In vivo activation of decidual lymphocytes might occur as a result of viral infection. CMV is the leading cause of congenital viral infections in Western countries. It was therefore tested whether CEACAM1 expression could be detected on the surface of lymphocytes obtained from deciduae of women who had primary CMV infection during gestation with documented intrauterine manifestations. Second and third-trimester pregnancy terminations of women diagnosed with primary CMV infection necessitate the administration of labor-promoting agents that might have some immunological effects. To control the experiment, the expression of CEACAM1 protein on the surface of lymphocytes obtained either from third-trimester caesarian sections with labor (Table 1; this section) or from the deciduae taken from caesarian sections without labor (Table 1; this section) were analyzed. Decidual lymphocytes were obtained and stained for the presence of CEACAM1 on NK, NKT, and T cells as above. Only very limited numbers of NKT cells were isolated, and therefore the expression of CEACAM1 on NKT cells could not be determined. Remarkably, a significant elevation of CEACAM1 expression was observed in NK and T cells obtained from deciduae of CMV-infected women, whereas little or no expression of CEACAM1 was observed in the two control groups (Table 1; this section). CEACAM1 expression can vary significantly between different CMV-infected deciduae. In one patient, 90% and 95% of the NK and T cells, respectively, expressed the CEACAM1 protein, whereas in the second patient the expression of the CEACAM1 protein was limited to 10% and 10.2% of NK and T cells, respectively. However, the expression of the CEACAM1 protein, even in the second patient, was still very significant compared with that of the control groups, and it was similar to the expression level of other class I MHC inhibitory receptors, which vary between 5% and 20%. There are several possible reasons for the differences in the level of CEACAM1 expression, such as subjective local immune response, course of CMV infection, and the time of pregnancy termination after the initiation of infection. The mild expression of the CEACAM1 protein on trophoblasts obtained from normal decidua (FIG. 25h) was still maintained on trophoblasts obtained from infected decidua.

CMV-Infected Fibroblasts Express a Novel Ligand for CEACAM1

The results presented above demonstrate that CEACAM1 expression is upregulated in vivo in lymphocytes obtained from CMV-infected deciduae. Expression of CEACAM1 was observed on EVT cells obtained from either normal or CMV-infected deciduae (FIG. 25). CEACAM1 homotypic interactions might occur in vivo, leading to lymphocyte inhibition.

Only two cases of CMV-infected deciduae are presented here, as studies in vivo are limited for several reasons. In addition to the fact that primary CMV infection during pregnancy is quite rare, the detection and diagnosis are quite difficult. Furthermore, deciduae from CMV-infected women were used only if they spontaneously detached, to avoid unnecessary additional procedures. However, in both presented cases, CEACAM1 upregulation was observed. To further establish the effect of CMV infection with regard to CEACAM1 inhibition and to test whether the CMV uses the CEACAM1 inhibitory mechanism to avoid attack by the immune system, CMV-infected HFFs were used. HFF cells were infected with CMV strain AD169 with moi 2-3. No staining of either infected or uninfected HFF cells with anti-CEACAM1, -5, and -6 Kat4c mAb was observed at any time point before or after the infection. Infected cells were harvested at different time points at 24-hour intervals after the infection and stained for the presence of CEACAM1 ligand using CEACAM1-Ig fusion protein, as described in Methods of this section.

The CEACAM1-Ig fusion protein specifically stained the 0.221/CEACAM1 cells and did not stain the 0.221 cells (FIG. 30a), indicating that CEACAM1 homotypic interactions are strong enough to be detected by this method. No staining of CEACAM1-Ig was observed in the first 4 days after the infection (FIG. 30b). CEACAM1-Ig staining was observed starting on day 5 and reaching maximum on day 6 after the infection. All infected cells were positively stained with anti-pp65 mAb. The CEACAM1-Ig binding observed was only to the HFF-infected cells, not to the uninfected cells. No changes in the level of the control CD99-Ig fusion protein staining were observed at any time point (FIG. 30b). As CEACAM1 can interact only with the CEACAM1, -5, and -6 variants, and as it was also reported that CEACAM variants cannot be detected on the surface of human fibroblasts, suggesting the existence of a novel ligand for CEACAM1 on the surface of CMV-infected HFF cells. This novel ligand appears late after the infection. To further test this hypothesis, similar experiments in the presence of the antiviral agent PFA, which is known to block viral DNA synthesis and early late-phase transition were performed. Progeny virus titers in culture supernatants were determined on day 4 after infection by a standard plaque titration assay on HFFs. In the absence of PFA, virus titer was 3×106 plaque-forming units/ml, whereas in the presence of PFA no virus could be detected. In agreement with the above observations demonstrating the appearance of CEACAM1 ligand on the surface of CMV-infected HFFs, the addition of PFA completely abolished the binding of CEACAM1-Ig to the infected HFF cells (FIG. 30b).

Whether the CEACAM1 interactions with the CMV-infected HFFs are functional was tested. Mouse BW cells were stably transfected with a chimeric molecule composed of the extracellular portion of CEACAM1 fused to mouse ζ chain (as described in Methods). Engagement of CEACAM1 leads to the secretion of mouse IL-2, mediated by the ζ chain. The IL-2 amounts in the cell supernatants can be measured by ELISA. Secretion of IL-2 could be detected in the culture supernatants of the BW cells transfected with CEACAM1ζ, but not in the culture supernatants of the BW cells or BW cells transfected with CD16ζ ((FIG. 31a). Moreover, IL-2 secretion was also detected in the supernatants of BW/CEACAM1 ζ cells when cells were incubated with 0.221/CEACAM1 cells, but not with they were incubated with 0.221 cells (FIG. 31b). Thus, homotypic CEACAM1 interactions are strong enough to induce IL-2 secretion in this system. In agreement with the CEACAM1-Ig staining data, efficient secretion of IL-2 was observed (on days 5 and 6 after the infection) in the supernatants of BW/CEACAM1ζ cells cultured with infected HFFs. This IL-2 secretion was blocked by the addition of PFA (FIG. 31c). No IL-2 secretion was observed in the culture supernatants of BW/CD16ζ cells incubated with uninfected or infected HFF cells.

Figure 32:
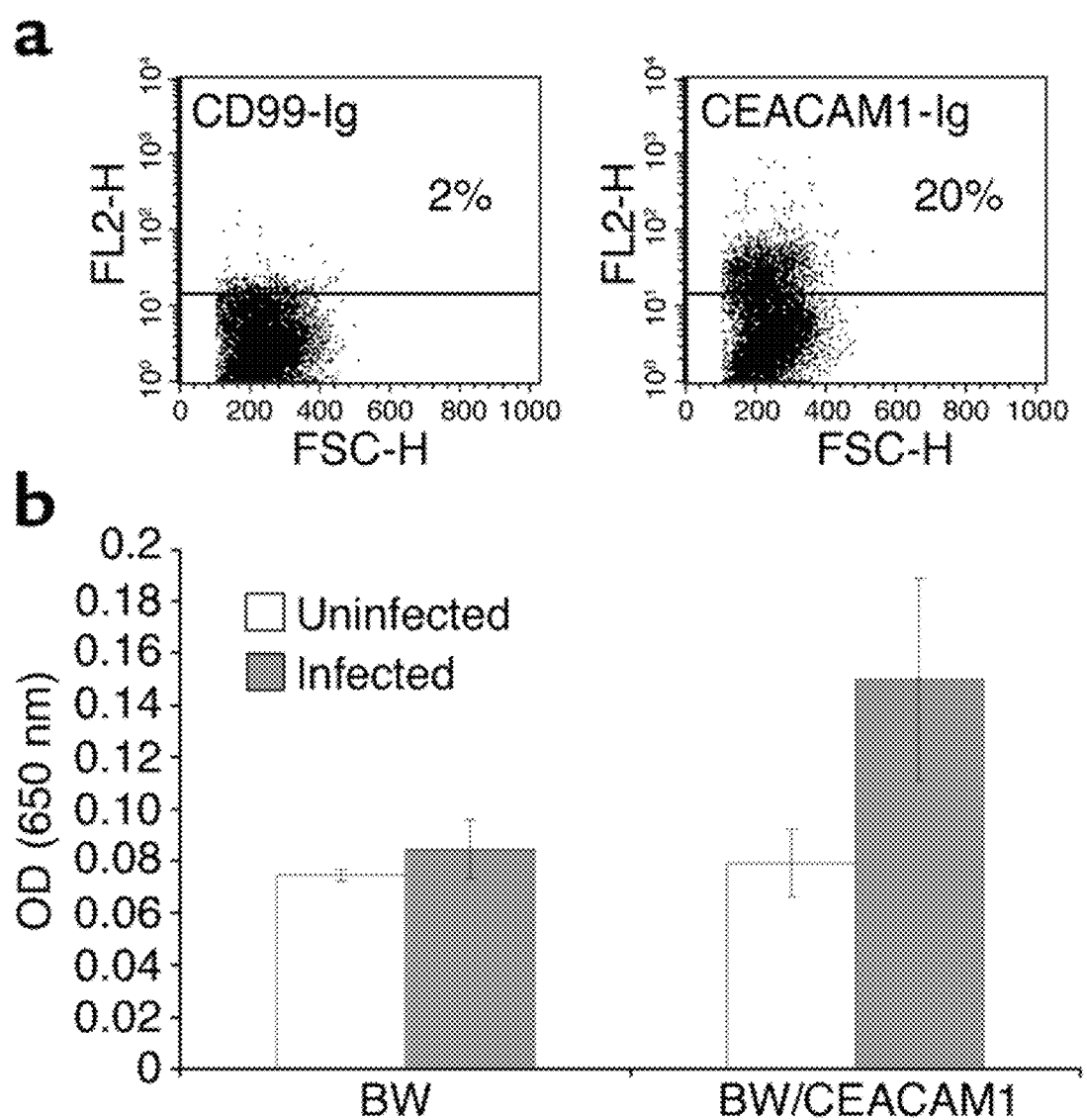
FIG. 32. CMV isolated from infected decidual induces a ligand for the CEACAM1 on infected HFF cells. (a) Staining of HFF cells infected with clinical CMV strain with CD99-Ig or with CEACAM1-Ig. No staining was observed when proteins were omitted, indicated by the horizontal line. FSC, forward scatter. (b) IL-2 secretion from BW or BW/CEACAM1☐ cells coincubated with HFF-infected cells for 48 hours. The average of two experiments is shown.

To further substantiate the above results, the clinical CMV strain isolated from the infected decidua was cultured (patient 6; Table 1 of this section) with infected HFF cells. The propagation of the virus was much slower than that of the laboratory AD169 strain. Consistent microscopic monitoring of infected HFF cells revealed that even after prolonged propagation time, only partial infection could be achieved. One month after initiation of infection, infected HFF cells were analyzed for recognition by CEACAM1. HFF cells were stained with Ig-fused proteins, including CEACAM1-Ig and the control CD99-Ig. No staining of uninfected HFF cells was observed. Specific staining of the infected HFF cells could be observed with the CEACAM1-Ig but not with the CD99-Ig (20% and 2% staining, respectively; FIG. 32a). No staining was observed when anti-CEACAM antibodies were used, suggesting that CEACAM1-Ig recognizes a novel CMV-induced ligand on infected HFFs. Whether this recognition is capable of eliciting IL-2 secretion from BW/CEACAM1⟨ cells was tested. IL-2 levels were measured in the supernatants of BW or BW/CEACAM1⟨ cells cocultured with HFF cells infected with the clinical CMV strain isolated from patient 6. In agreement with the CEACAM1-Ig staining, increased IL-2 secretion could be detected only in the supernatants of the BW/CEACAM1⟨ cells coincubated with infected HFF cells (FIG. 32b). The moderate elevation of IL-2 secretion and the partial staining of CEACAM1-Ig (FIG. 32, a and b) are correlated with the low infection levels of this clinical CMV strain observed in vitro, and with the moderate percentages of CEACAM1+ lymphocytes isolated from infected decidua no. 2 (patient 6; Table 1 of this section). Similar results were obtained with another clinical CMV strain, isolated from a neonate's urine.

TABLE 1

CEACAM1 expression is upregulated on decidual lymphocytes from women with primary CMV infection

| Patient no. | Decidua source | NK cells | T cells | NKT cells |
|---|---|---|---|---|
| 1 | With labor | 0.5% | 1.9% | Not detected |
| 2 | With labor | 1% | 0% | Not detected |

TABLE 1-continued

CEACAM1 expression is upregulated on decidual lymphocytes from women with primary CMV infection

| Patient no. | Decidua source | NK cells | T cells | NKT cells |
|---|---|---|---|---|
| 3 | Without labor | 1.7% | 2.5% | Not detected |
| 4 | Without labor | 0% | 0.4% | Not detected |
| 5 | With CMV | 95% | 90% | Not detected |
| 6 | With CMV | 10% | 10.2% | Not detected |

Cells were isolated from deciduae from different groups and quadruple stained for CD3, CD16, CD56, and CEACAM1 as described in Methods. The percentage of CEACAM1+ cells of each indicated lymphocyte subset is shown.

What is claimed is:

1. A method for enhancing natural killer-cell mediated killing activity, wherein said method comprises contacting a natural killer-cell expressing CEACAM1 with a CEACAM1 binding element that is a multimer agent comprising at least SEQ ID No. 1.

2. The method of claim 1, wherein said method is performed in situ, in vivo, or in vitro.

3. The method of claim 1, wherein said method is performed in a cell culture comprising a population of Tumor Infiltrating Lymphocytes.

* * * * *

SEQUENCE LISTING

<160> NUMBER OF SEQ ID NOS: 32

<210> SEQ ID NO 1
<211> LENGTH: 108
<212> TYPE: PRT
<213> ORGANISM: Homo Sapiens
<220> FEATURE:
<221> NAME/KEY: MISC_FEATURE
<223> OTHER INFORMATION: CEACAM1 N-terminal domain

<400> SEQUENCE: 1

Gln Leu Thr Thr Glu Ser Met Pro Phe Asn Val Ala Gly Lys Glu
1               5                   10                  15

Val Leu Leu Leu Val His Asn Leu Pro Gln Gln Leu Phe Gly Tyr Ser
                20                  25                  30

Trp Tyr Lys Gly Glu Arg Val Asp Gly Asn Arg Gln Ile Val Gly Tyr
            35                  40                  45

Ala Ile Gly Thr Gln Gln Ala Thr Pro Gly Pro Ala Asn Ser Gly Arg
        50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro
            100                 105

<210> SEQ ID NO 2
<211> LENGTH: 108
<212> TYPE: PRT
<213> ORGANISM: Homo Sapiens
<220> FEATURE:
<221> NAME/KEY: MISC_FEATURE
<223> OTHER INFORMATION: CEACAM3 N-terminal domain

<400> SEQUENCE: 2

Lys Leu Thr Ile Glu Ser Met Pro Leu Ser Val Ala Glu Gly Lys Glu
1               5                   10                  15

Val Leu Leu Leu Val His Asn Leu Pro Gln His Leu Phe Gly Tyr Ser

```
                    20                  25                  30

Trp Tyr Lys Gly Glu Arg Val Asp Gly Asn Ser Leu Ile Val Gly Tyr
            35                  40                  45

Val Ile Gly Thr Gln Gln Ala Thr Pro Gly Ala Ala Tyr Ser Gly Arg
    50                  55                  60

Glu Thr Ile Tyr Thr Asn Ala Ser Leu Leu Ile Gln Asn Val Thr Gln
65                  70                  75                  80

Asn Asp Ile Gly Phe Tyr Thr Leu Gln Val Ile Lys Ser Asp Leu Val
                85                  90                  95

Asn Glu Glu Ala Thr Gly Gln Phe His Val Tyr Gln
            100                 105

<210> SEQ ID NO 3
<211> LENGTH: 108
<212> TYPE: PRT
<213> ORGANISM: Homo Sapiens
<220> FEATURE:
<221> NAME/KEY: MISC_FEATURE
<223> OTHER INFORMATION: CEACAM5 N-terminal domain

<400> SEQUENCE: 3

Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
                20                  25                  30

Trp Tyr Lys Gly Glu Arg Val Asp Gly Asn Arg Gln Ile Ile Gly Tyr
            35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro
            100                 105

<210> SEQ ID NO 4
<211> LENGTH: 108
<212> TYPE: PRT
<213> ORGANISM: Homo Sapiens
<220> FEATURE:
<221> NAME/KEY: MISC_FEATURE
<223> OTHER INFORMATION: CEACAM6 N-terminal domain

<400> SEQUENCE: 4

Lys Leu Thr Ile Glu Ser Thr Pro Phe Asn Val Ala Glu Gly Lys Glu
1               5                   10                  15

Val Leu Leu Leu Ala His Asn Leu Pro Gln Asn Arg Ile Gly Tyr Ser
                20                  25                  30

Trp Tyr Lys Gly Glu Arg Val Asp Gly Asn Ser Leu Ile Val Gly Tyr
            35                  40                  45

Val Ile Gly Thr Gln Gln Ala Thr Pro Gly Pro Ala Tyr Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro
```

```
<210> SEQ ID NO 5
<211> LENGTH: 39
<212> TYPE: DNA
<213> ORGANISM: Artificial
<220> FEATURE:
<223> OTHER INFORMATION: 5' PCR primer employed to amplify the
      extracellular portion of the CEACAM1 protein, and incorporating
      a HindIII restriction site.

<400> SEQUENCE: 5
cccaagcttg gggccgccac catggggcac ctctcagcc                              39

<210> SEQ ID NO 6
<211> LENGTH: 36
<212> TYPE: DNA
<213> ORGANISM: Artificial
<220> FEATURE:
<223> OTHER INFORMATION: 5' PCR primer employed to amplify the
      extracellular portion of the CEACAM6 without the GPI-ancoring
      sequence, and incorporating a HindIII restriction site.

<400> SEQUENCE: 6
cccaagcttg ccgccaccat gggaccccccc tcagcc                                36

<210> SEQ ID NO 7
<211> LENGTH: 30
<212> TYPE: DNA
<213> ORGANISM: Artificial
<220> FEATURE:
<223> OTHER INFORMATION: 3' PCR primer employed to amplify the
      extracellular portion of the CEACAM6 without the GPI-anchoring
      sequence, and incorporating the first nine nucleotides of the
      CEACAM1 transmembrane portion.

<400> SEQUENCE: 7
aatggcccct ccagagactg tgatcatcgt                                        30

<210> SEQ ID NO 8
<211> LENGTH: 28
<212> TYPE: DNA
<213> ORGANISM: Artificial
<220> FEATURE:
<223> OTHER INFORMATION: 5' PCR primer employed to amplify the
      transmembrane and tail of CEACAM1, including the last nine
      nucleotides of the CEACAM6 extracellular portion before the GPI
      anchor motif.

<400> SEQUENCE: 8
gtctctggag gggccattgc tggcattg                                          28

<210> SEQ ID NO 9
<211> LENGTH: 32
<212> TYPE: DNA
<213> ORGANISM: Artificial
<220> FEATURE:
<223> OTHER INFORMATION: 3' PCR primer employed to amplify the
      transmembrane and tail of CEACAM1, and incorporating the EcoRI
      restriction site.

<400> SEQUENCE: 9
ggaattcctt actgcttttt tacttctgaa ta                                     32

<210> SEQ ID NO 10
<211> LENGTH: 39
<212> TYPE: DNA
<213> ORGANISM: Artificial
```

```
<220> FEATURE:
<223> OTHER INFORMATION: 5' PCR primer employed to amplify the
      extracellular portion of the human CEACAM1 protein, and
      incorporating a HindIII restriction site.

<400> SEQUENCE: 10
cccaagcttg gggccgccac catggggcac ctctcagcc                           39

<210> SEQ ID NO 11
<211> LENGTH: 30
<212> TYPE: DNA
<213> ORGANISM: Artificial
<220> FEATURE:
<223> OTHER INFORMATION: 3' PCR primer used to amplify the
      extracellular portion of the human CEACAM1 protein, including
      the the first nine nucleotides of the mouse chain transmembrane
      portion.

<400> SEQUENCE: 11
gtagcagaga ggtgagaggc cattttcttg                                     30

<210> SEQ ID NO 12
<211> LENGTH: 30
<212> TYPE: DNA
<213> ORGANISM: Artificial
<220> FEATURE:
<223> OTHER INFORMATION: 5' PCR primer used to amplify the mouse chain,
      including the last nine nucleotides of the human CEACAM1
      extracellular portion.

<400> SEQUENCE: 12
ctctcacctc tctgctactt gctagatgga                                     30

<210> SEQ ID NO 13
<211> LENGTH: 29
<212> TYPE: DNA
<213> ORGANISM: Artificial
<220> FEATURE:
<223> OTHER INFORMATION: 3' PCR primer used to amplify the mouse chain,
      including an EcoRI restriction site.

<400> SEQUENCE: 13
ggaattcctt agcgaggggc cagggtctg                                      29

<210> SEQ ID NO 14
<211> LENGTH: 21
<212> TYPE: DNA
<213> ORGANISM: Artificial
<220> FEATURE:
<223> OTHER INFORMATION: 5' internal primer for the generation of
      CEACAM1-RQ43,44SL mutant.

<400> SEQUENCE: 14
gccaacagtc taattgtagg a                                              21

<210> SEQ ID NO 15
<211> LENGTH: 21
<212> TYPE: DNA
<213> ORGANISM: Artificial
<220> FEATURE:
<223> OTHER INFORMATION: 3' internal primer for the generation of
      CEACAM1-RQ43,44SL mutant.

<400> SEQUENCE: 15
tcctacaatt agactgttgc c                                              21

<210> SEQ ID NO 16
```

```
<211> LENGTH: 21
<212> TYPE: DNA
<213> ORGANISM: Artificial
<220> FEATURE:
<223> OTHER INFORMATION: 5' internal primer for the generation of
      CEACAM1-R43A mutant

<400> SEQUENCE: 16
gatggcaacg ctcaaattgt a                                              21

<210> SEQ ID NO 17
<211> LENGTH: 21
<212> TYPE: DNA
<213> ORGANISM: Artificial
<220> FEATURE:
<223> OTHER INFORMATION: 3' internal primer for the generation of
      CEACAM1-R43A mutant.

<400> SEQUENCE: 17
tacaatttga gcgttgccat c                                              21

<210> SEQ ID NO 18
<211> LENGTH: 21
<212> TYPE: DNA
<213> ORGANISM: Artificial
<220> FEATURE:
<223> OTHER INFORMATION: 5' internal primer for the generation of
      CEACAM1-Q44L mutant.

<400> SEQUENCE: 18
atggcaaccg tctaattgta g                                              21

<210> SEQ ID NO 19
<211> LENGTH: 21
<212> TYPE: DNA
<213> ORGANISM: Artificial
<220> FEATURE:
<223> OTHER INFORMATION: 3' internal primer for the generation of
      CEACAM1-Q44L mutant.

<400> SEQUENCE: 19
ctacaattag acggttgcca t                                              21

<210> SEQ ID NO 20
<211> LENGTH: 28
<212> TYPE: DNA
<213> ORGANISM: Artificial
<220> FEATURE:
<223> OTHER INFORMATION: 3' edge primer for the generation of
      CEACAM6-SL43,44RQ mutant

<400> SEQUENCE: 20
ggaattccct atatcagagc caccctgg                                       28

<210> SEQ ID NO 21
<211> LENGTH: 21
<212> TYPE: DNA
<213> ORGANISM: Artificial
<220> FEATURE:
<223> OTHER INFORMATION: 5' internal primer for the generation of
      CEACAM6-SL43,44RQ mutant

<400> SEQUENCE: 21
ggcaaccgtc aaattgtagg a                                              21

<210> SEQ ID NO 22
<211> LENGTH: 21
```

```
<212> TYPE: DNA
<213> ORGANISM: Artificial
<220> FEATURE:
<223> OTHER INFORMATION: 3' internal primer for the generation of
      CEACAM6-SL43,44RQ mutant

<400> SEQUENCE: 22
tcctacaatt tgacggttgc c                                          21

<210> SEQ ID NO 23
<211> LENGTH: 21
<212> TYPE: DNA
<213> ORGANISM: Artificial
<220> FEATURE:
<223> OTHER INFORMATION: 5' internal primer for the generation of For
      CEACAM6-S43R mutant.

<400> SEQUENCE: 23
gatggcaacc gtctaattgt a                                          21

<210> SEQ ID NO 24
<211> LENGTH: 21
<212> TYPE: DNA
<213> ORGANISM: Artificial
<220> FEATURE:
<223> OTHER INFORMATION: 3' internal primer for the generation of For
      CEACAM6-S43R mutant.

<400> SEQUENCE: 24
tacaattaga cggttgccat c                                          21

<210> SEQ ID NO 25
<211> LENGTH: 21
<212> TYPE: DNA
<213> ORGANISM: Artificial
<220> FEATURE:
<223> OTHER INFORMATION: 5' internal primer for the generation
      CEACAM6-L44Q mutant.

<400> SEQUENCE: 25
gatggcaaca gtcaaattgt a                                          21

<210> SEQ ID NO 26
<211> LENGTH: 21
<212> TYPE: DNA
<213> ORGANISM: Artificial
<220> FEATURE:
<223> OTHER INFORMATION: 3' internal primer for the generation
      CEACAM6-L44Q mutant.

<400> SEQUENCE: 26
tacaatttga ctgttgccat c                                          21

<210> SEQ ID NO 27
<211> LENGTH: 35
<212> TYPE: DNA
<213> ORGANISM: Artificial
<220> FEATURE:
<223> OTHER INFORMATION: 5' PCR primer for the amplification of
      CD66a cDNA needed for the
      transfection of 721.221 cells, incorporating a HindIII
      restriction site.

<400> SEQUENCE: 27
ggaattccgc cgccaccatg gggcacctct cagcc                           35

<210> SEQ ID NO 28
```

<210> SEQ ID NO 28
<211> LENGTH: 32
<212> TYPE: DNA
<213> ORGANISM: Artificial
<220> FEATURE:
<223> OTHER INFORMATION: 3' PCR primer for the amplification of CD66a cDNA needed for the transfection of 721.221 cells, incorporating an EcoRI restriction site.

<400> SEQUENCE: 28
gcgtcgactt actgcttttt tacttctgaa ta          32

<210> SEQ ID NO 29
<211> LENGTH: 28
<212> TYPE: DNA
<213> ORGANISM: Artificial
<220> FEATURE:
<223> OTHER INFORMATION: 3' PCR primer for the amplification CD66a truncated cDNA.

<400> SEQUENCE: 29
gcgtcgacat cttgttaggt gggtcatt              28

<210> SEQ ID NO 30
<211> LENGTH: 21
<212> TYPE: DNA
<213> ORGANISM: Artificial
<220> FEATURE:
<223> OTHER INFORMATION: 3' PCR primer employed to amplify the extracellular portion of the CEACAM1 protein, and incorporating a BamH1 restriction site.

<400> SEQUENCE: 30
cggagagtgg acccctaggc g                      21

<210> SEQ ID NO 31
<211> LENGTH: 30
<212> TYPE: DNA
<213> ORGANISM: Artificial
<220> FEATURE:
<223> OTHER INFORMATION: 5' PCR primer for the amplification of the mouse chain, including the last nine nucleotides of the human CEACAM1 extracellular portion.

<400> SEQUENCE: 31
ctctcacctc tctgctactt gctagatgga             30

<210> SEQ ID NO 32
<211> LENGTH: 29
<212> TYPE: DNA
<213> ORGANISM: Artificial
<220> FEATURE:
<223> OTHER INFORMATION: 3' PCR primer used to amplify a mouse chain, including an EcoRI restriction site.

<400> SEQUENCE: 32
ggaattcctt agcgaggggc cagggtctg              29